(12) United States Patent
Martin et al.

(10) Patent No.: US 9,814,457 B2
(45) Date of Patent: Nov. 14, 2017

(54) CONTROL INTERFACE FOR LAPAROSCOPIC SUTURING INSTRUMENT

(75) Inventors: David T. Martin, Milford, OH (US); James A. Woodard, Jr., Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 364 days.

(21) Appl. No.: 13/443,101

(22) Filed: Apr. 10, 2012

(65) Prior Publication Data

US 2013/0267969 A1 Oct. 10, 2013

(51) Int. Cl.
| | | |
|---|---|---|
| A61B 17/04 | (2006.01) | |
| A61B 17/062 | (2006.01) | |
| A61B 34/35 | (2016.01) | |
| A61B 17/00 | (2006.01) | |
| A61B 34/30 | (2016.01) | |

(52) U.S. Cl.
CPC ...... *A61B 17/0469* (2013.01); *A61B 17/0491* (2013.01); *A61B 17/0625* (2013.01); *A61B 34/35* (2016.02); *A61B 2017/00477* (2013.01); *A61B 2034/302* (2016.02)

(58) Field of Classification Search
CPC ........ A61B 17/0469; A61B 2017/0472; A61B 18/1445
USPC ......................................... 606/139, 138, 144
See application file for complete search history.

(56) References Cited

U.S. PATENT DOCUMENTS

| | | | |
|---|---|---|---|
| 5,674,230 A | 10/1997 | Tovey et al. | |
| 5,993,466 A * | 11/1999 | Yoon .................... | A61B 17/062 606/144 |
| 6,056,771 A | 5/2000 | Proto | |
| 6,071,289 A | 6/2000 | Stefanchik et al. | |
| 6,783,524 B2 * | 8/2004 | Anderson et al. .............. | 606/28 |
| 6,866,671 B2 * | 3/2005 | Tierney et al. ............... | 606/130 |
| 7,628,796 B2 | 12/2009 | Shelton, IV et al. | |
| 7,775,972 B2 * | 8/2010 | Brock et al. .................. | 600/114 |
| 8,137,339 B2 | 3/2012 | Jinno et al. | |
| 2007/0060931 A1 * | 3/2007 | Hamilton et al. ............ | 606/144 |

(Continued)

FOREIGN PATENT DOCUMENTS

| | | |
|---|---|---|
| EP | 2133028 | 12/2009 |
| WO | WO 98/48705 | 11/1998 |
| WO | WO 2012/068002 | 5/2012 |

OTHER PUBLICATIONS

International Search Report and Written Opinion dated Oct. 4, 2013 for Application No. PCT/US2013/035927.

*Primary Examiner* — Gregory Anderson
*Assistant Examiner* — Sarah Simpson
(74) *Attorney, Agent, or Firm* — Frost Brown Todd LLC

(57) ABSTRACT

An apparatus comprises an end effector, a shaft assembly, and a drive assembly. The end effector comprises needle receiving arms operable to grasp a needle. The drive assembly comprises drive members that are rotatable about respective drive axes that are perpendicular to the axis of the shaft assembly. The drive assembly is operable to drive the needle receiving arms to selectively engage and disengage the needle; and to selectively pass the needle from one needle receiving arm to the other needle receiving arm. The drive assembly provides an interface to a controller that is operable via a remote user interface. The drive assembly may include helical gears, clutch assemblies, a rack and pinion, or other components to convert motion of the drive members into motion at the end effector.

8 Claims, 37 Drawing Sheets

(56) References Cited

U.S. PATENT DOCUMENTS

| | | | |
|---|---|---|---|
| 2008/0228204 A1* | 9/2008 | Hamilton et al. | 606/148 |
| 2010/0030238 A1* | 2/2010 | Viola et al. | 606/144 |
| 2010/0100125 A1 | 4/2010 | Mahadevan | |
| 2011/0290854 A1* | 12/2011 | Timm | A61B 17/072 227/178.1 |
| 2011/0313433 A1 | 12/2011 | Woodard, Jr. et al. | |
| 2012/0123471 A1 | 5/2012 | Woodard, Jr. et al. | |
| 2012/0143223 A1 | 6/2012 | Woodard, Jr. et al. | |
| 2012/0150199 A1* | 6/2012 | Woodard et al. | 606/147 |

* cited by examiner

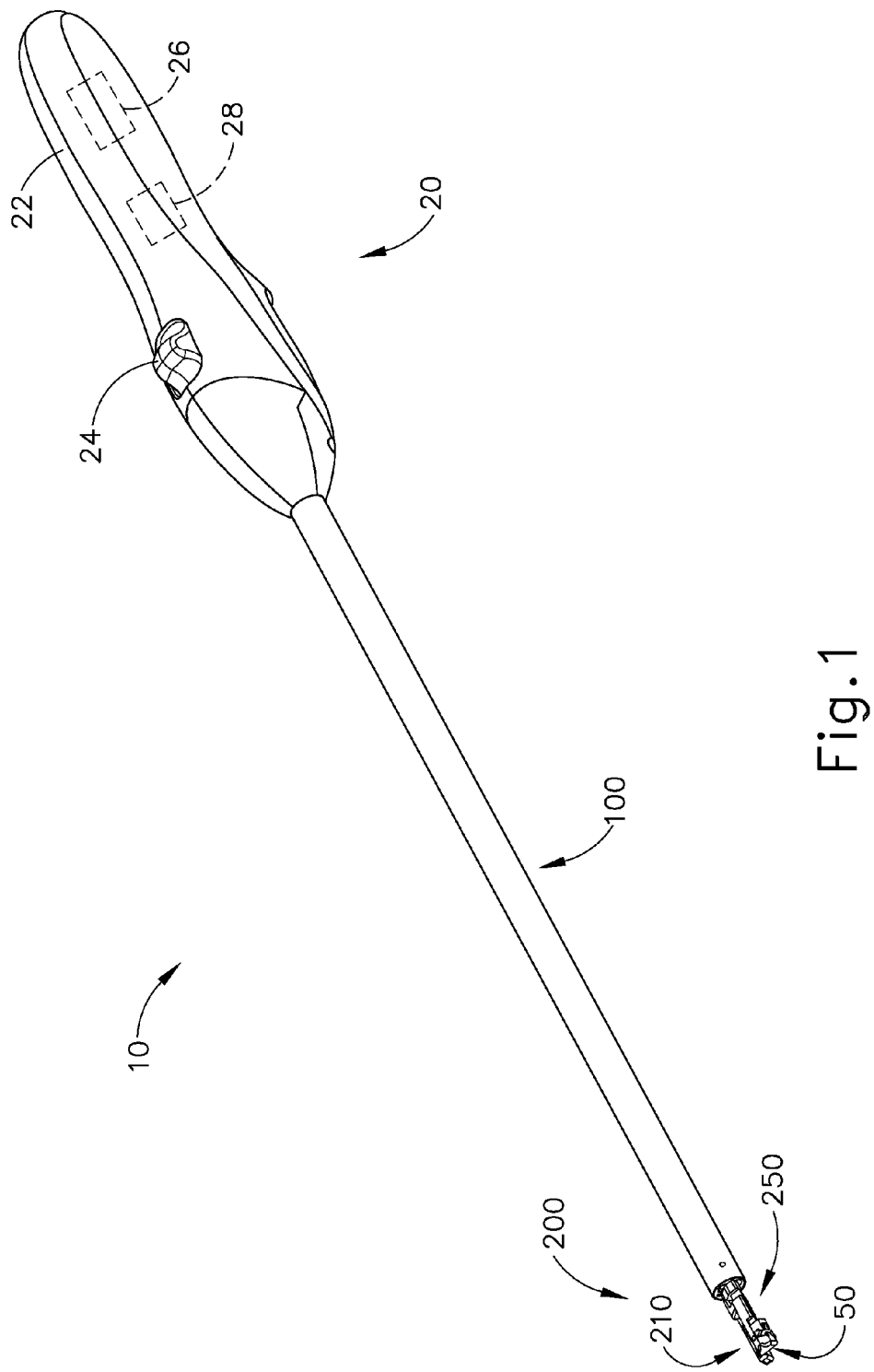

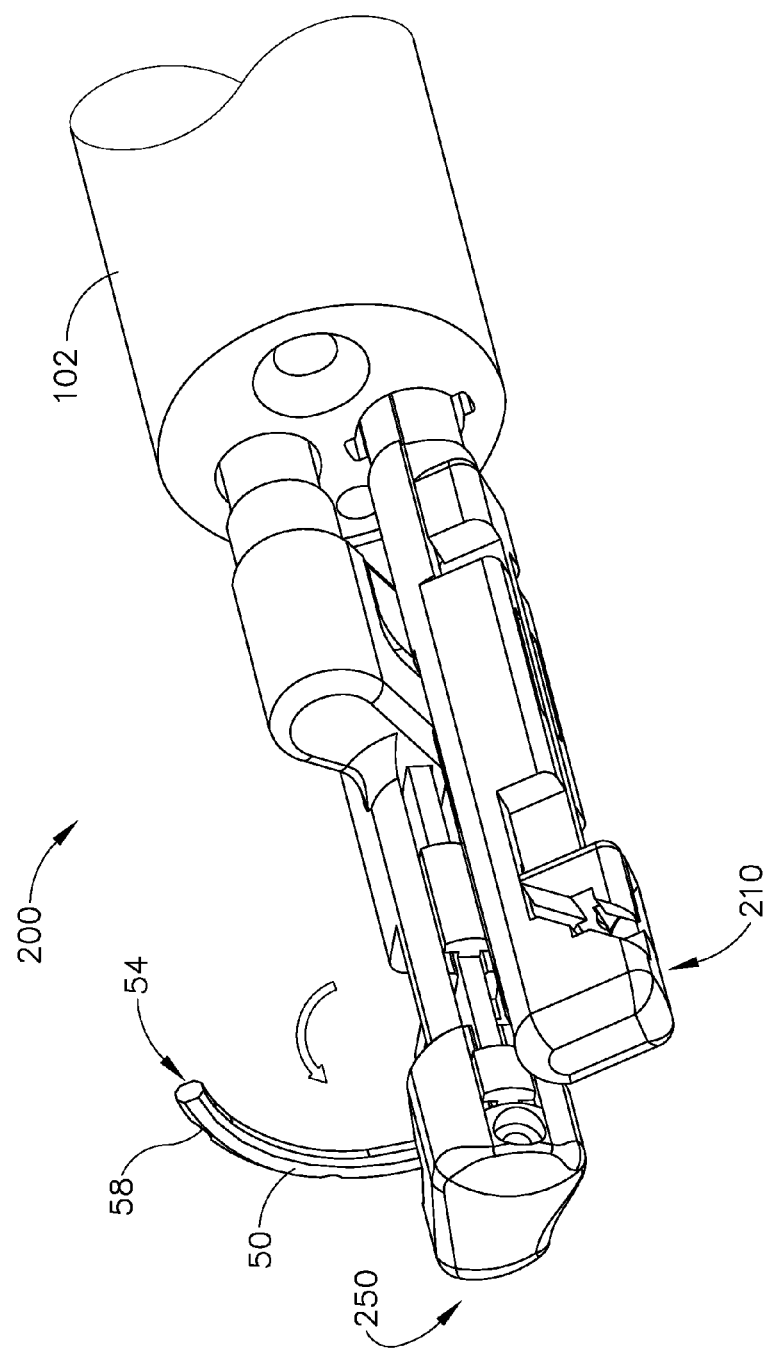

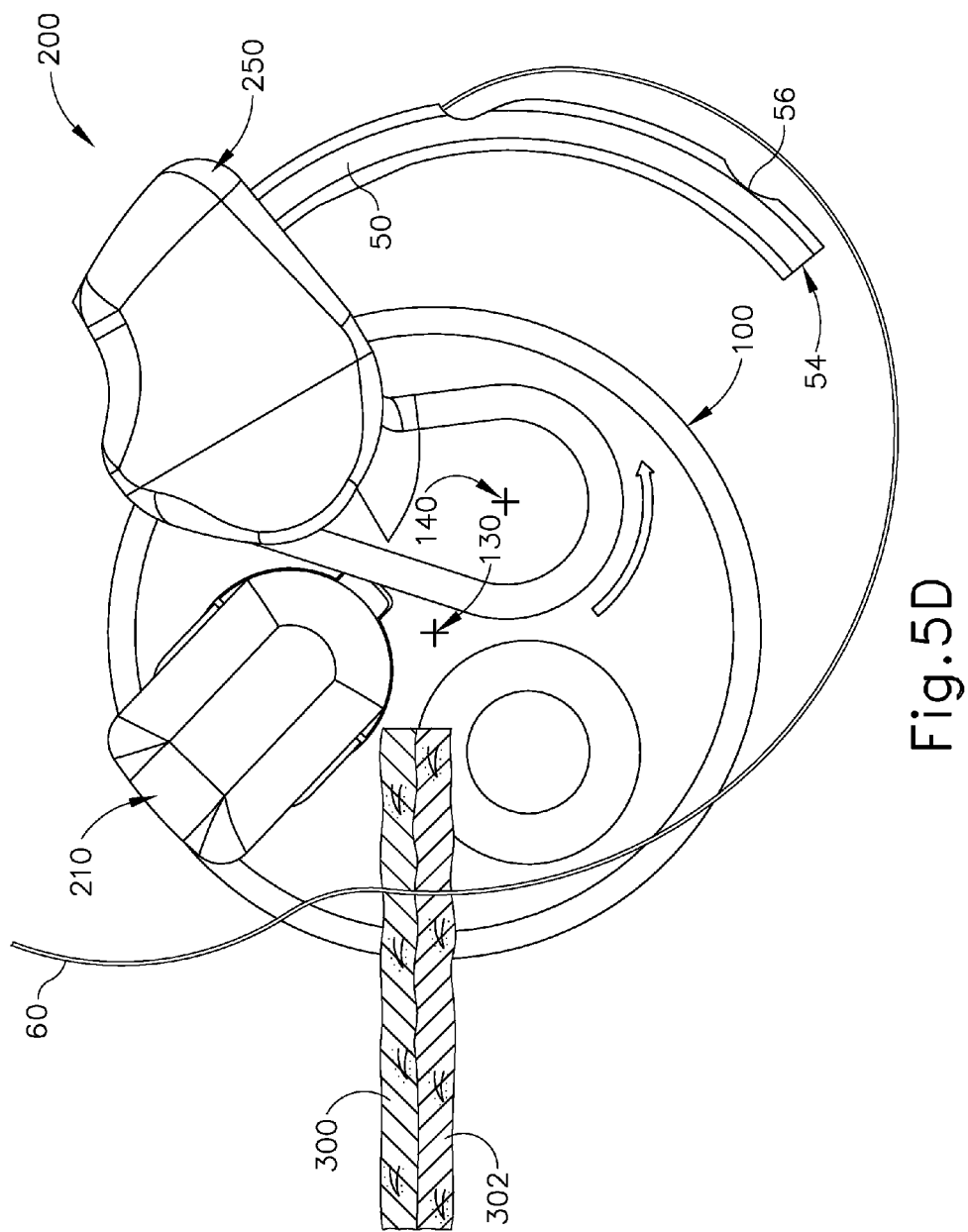

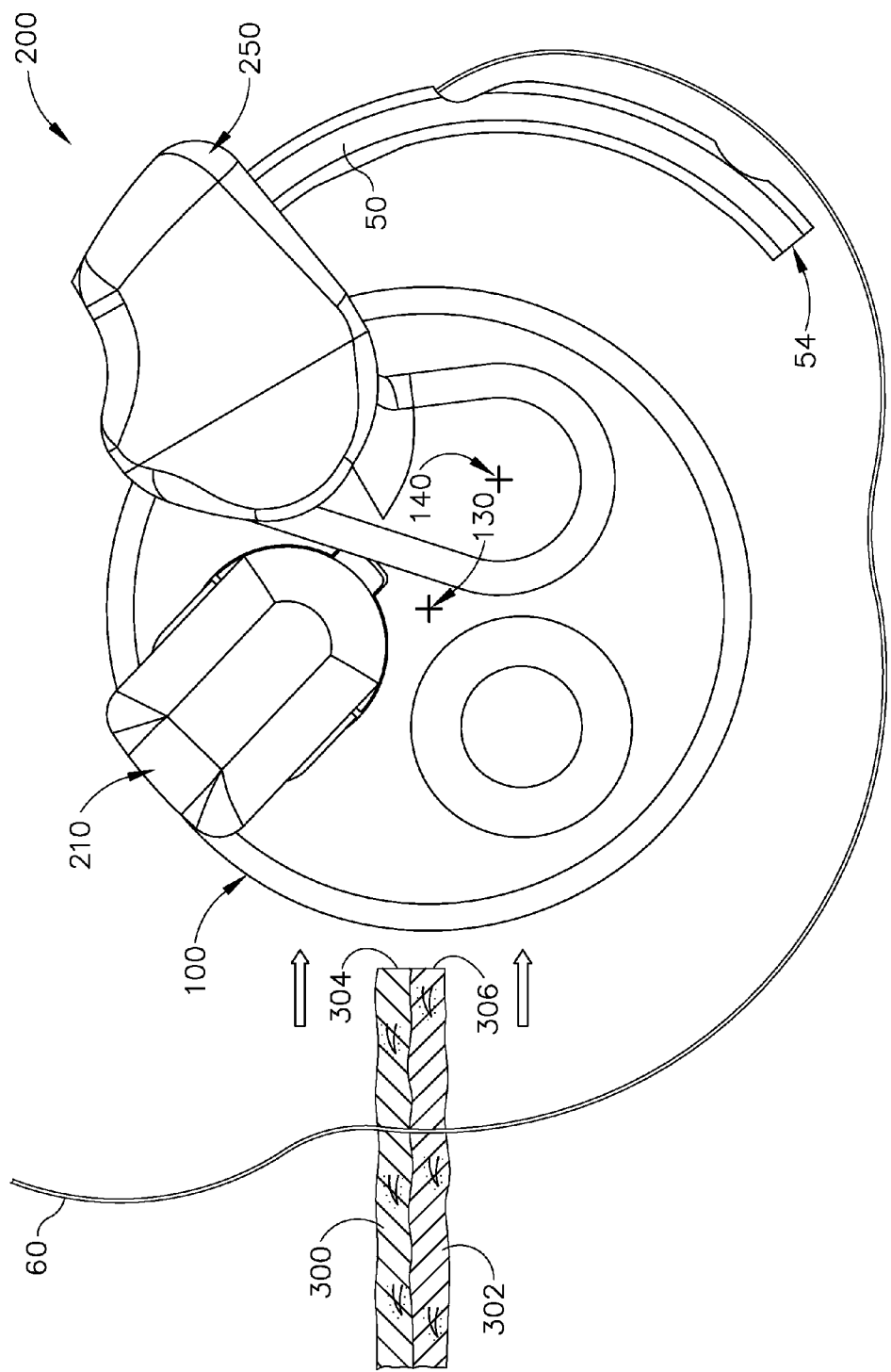

CONTROL INTERFACE FOR LAPAROSCOPIC SUTURING INSTRUMENT

BACKGROUND

In some settings it may be desirable to perform a surgical procedure in a minimally invasive manner, such as through a trocar or other type of access cannula. Examples of trocars include the various ENDOPATH® EXCEL™ products by Ethicon Endo-Surgery, Inc. of Cincinnati, Ohio. Such trocars may present different inner diameters, such as those ranging from approximately 4.7 mm to approximately 12.9 mm, allowing a surgeon to choose a particular trocar based on a balance of considerations such as access needs and incision size. In some minimally invasive surgical procedures, at least two trocars may be inserted through the abdominal wall of the patient. An imaging device such as an endoscope may be inserted through one of the trocars to provide visualization of the surgical site. A surgical instrument may be inserted through another one of the trocars to perform surgery at the site. In procedures performed within the abdominal cavity, the cavity may be insufflated with pressurized carbon dioxide to provide more room for visualization and manipulation of instruments. In some settings, additional trocars may be used to provide access for additional surgical instruments. Minimally invasive surgery may also be performed through access portals such as the Single Site Laparoscopy Access System by Ethicon Endo-Surgery, Inc. of Cincinnati, Ohio, which provides ports for more than one surgical instrument through a single incision in a patient.

It may also be desirable to use sutures during some minimally invasive surgical procedures, such as to close an opening, to secure two layers of tissue together, to provide an anastomosis, etc. Such use of sutures may be in addition to or in lieu of using other devices and techniques such as clips, staples, electrosurgical sealing, etc. Performing suturing through trocars or other minimally invasive access ports may be more difficult than suturing in an open surgical procedure. For instance, manipulating a needle and suture with conventional tissue graspers through trocars may be relatively difficult for many surgeons. Thus, improved laparoscopic surgical instruments may make suturing procedures performed through trocars relatively easier. Examples of surgical instruments configured to facilitate suturing through trocars include the LAPRA-TY® Suture Clip Applier, the Suture Assistant, and the ENDOPATH® Needle Holder, all of which are by Ethicon Endo-Surgery, Inc. of Cincinnati, Ohio. Additional suturing instruments are disclosed in U.S. Pat. No. 7,628,796, entitled "Surgical Suturing Apparatus with Anti-Backup System," issued Dec. 8, 2009, the disclosure of which is incorporated by reference herein; U.S. Pat. No. 6,071,289, entitled "Surgical Device for Suturing Tissue," issued Jun. 6, 2000, the disclosure of which is incorporated by reference herein; U.S. Patent Pub. No. 2011/0313433, entitled "Laparoscopic Suture Device with Asynchronous In-Line Needle Movement," published Dec. 22, 2011, now U.S. Pat. No. 9,168,037, issued on Oct. 27, 2015, the disclosure of which is incorporated by reference herein; U.S. patent application Ser. No. 13/295,203, entitled "Laparoscopic Suturing Instrument with Dual-Action Needle Graspers," filed Nov. 11, 2011, now U.S. Pat. No. 8,702,732, issued Apr. 22, 2014, the disclosure of which is incorporated by reference herein; U.S. patent application Ser. No. 13/295,210, entitled "Laparoscopic Suturing Instrument with Perpendicular Eccentric Needle Motion," filed Nov. 11, 2011, now U.S. Pat. No. 8,906,043, issued on Dec. 9, 2014, the disclosure of which is incorporated by reference herein; and U.S. Provisional Patent Application No. 61/355,832, entitled "Laparoscopic Suture Device," filed Jun. 17, 2010, the disclosure of which is incorporated by reference herein.

Exemplary suturing needles are disclosed in U.S. Pat. No. 6,056,771, entitled "Radiused Tip Surgical Needles and Surgical Incision Members," issued May 2, 2000, the disclosure of which is incorporated by reference herein; U.S. Pub. No. 2010/0100125, entitled "Suture Needle and Suture Assembly," published Apr. 22, 2010, the disclosure of which is incorporated by reference herein; U.S. Provisional Application Ser. No. 61/413,680, filed Nov. 15, 2010, entitled "Custom Needle for Suture Instrument," the disclosure of which is incorporated by reference herein; and U.S. patent application Ser. No. 13/295,186, entitled "Needle for Laparoscopic Suturing Instrument," filed on Nov. 14, 2011, now U.S. Pat. No. 9,125,646, issued on Sep. 8, 2015, the disclosure of which is incorporated by reference herein.

While a variety of devices and methods have been made and used for suturing tissue, it is believed that no one prior to the inventor(s) has made or used the technology described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 1 depicts a perspective view of an exemplary laparoscopic suturing instrument;

FIG. 2C depicts a perspective view of the end effector and needle of FIG. 2A, in a third operational configuration;

FIG. 5D depicts an end elevation view of the end effector and needle of FIG. 2A, during an exemplary fourth stage of operation;

FIG. 5E depicts an end elevation view of the end effector and needle of FIG. 2A, during an exemplary fifth stage of operation;

Figure 2A:
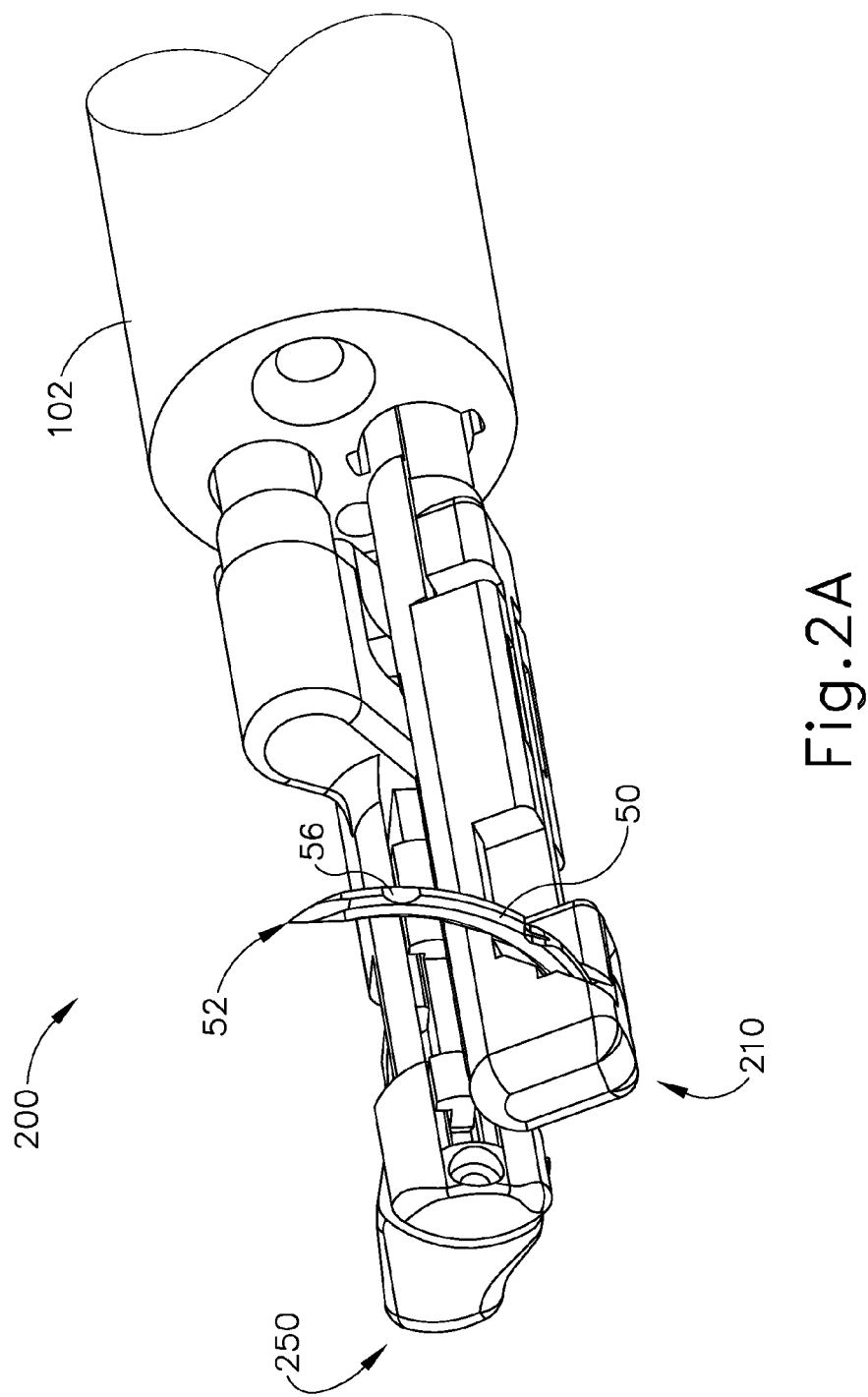
FIG. 2A depicts a perspective view of the end effector of the suturing instrument of FIG. 1 with a needle in a first operational configuration.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should therefore be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview

FIG. 1 shows an exemplary laparoscopic suturing instrument (10). Instrument (10) of this example includes a handle portion (20), a shaft (100) extending distally from handle portion (20), and an end effector (200) at the distal end of shaft (100). Handle portion (20) includes a grip (22), a rocker (24), an integral power source (26), and a motor (28) in communication with the integral power source (26). Rocker (24) is resiliently biased to a generally vertical position (e.g., generally perpendicular to grip (22)), though rocker (24) may be rocked forwardly or rearwardly. In addition or in the alternative, rocker (24) may be rocked to the left or to the right. Rocker (24) is operable to actuate features of end effector (200) as will be described in greater detail below. Of course, rocker (24) is merely one example of a user input feature, and any other suitable type of user input feature may be used.

Integral power source (26) comprises a rechargeable battery in the present example, though it should be understood that any other suitable power source may be used. By way of example only, instrument (10) may use a power source that is external to instrument (10) (e.g., coupled with instrument (10) via a cable, etc.). Similarly, while end effector (200) is powered by motor (28) in the present example, it should be understood that any other suitable source may be used, including but not limited to a manually operable mechanism. Various other suitable components, features, and configurations for handle portion (20) will be apparent to those of ordinary skill in the art in view of the teachings herein. By way of example only, handle portion (20) may be constructed in accordance with at least some of the teachings of U.S. Provisional Patent Application No. 61/355,832, the disclosure of which is incorporated by reference herein; and/or in accordance with at least some of the teachings of U.S. Pub. No. 2011/0313433, now U.S. Pat. No. 9,168,037, issued on Oct. 27, 2015, the disclosure of which is incorporated by reference herein. In some versions, handle portion (20) is substituted with an assembly configured to interface with a robotic surgical system, such as the DAVINCI™ system by Intuitive Surgical, Inc., of Sunnyvale, Calif. Various examples of such assemblies will be described in greater detail below, while still other suitable examples will be apparent to those of ordinary skill in the art in view of the teachings herein.

Shaft (100) of the present example has an outer diameter sized to permit shaft (100) to be inserted through a conventional trocar (not shown). Shaft (100) also has a length sized to permit end effector (200) to be positioned at a surgical site within a patient while also allowing handle portion (400) to be manipulated by a user (e.g., a surgeon) from a location outside the patient when shaft (100) is disposed in a trocar. Of course, shaft (100) need not necessarily be dimensioned for use through a trocar. For instance, instrument (10) may be used and/or configured for use in open surgical procedures.

In some versions, shaft (100) includes one or more articulating features, allowing end effector (200) to be articulated to various angles and positions relative to a longitudinal axis (130) (shown in FIGS. 5A-5H) defined by shaft (100). Merely illustrative examples of such articulation are taught in U.S. Provisional Application Ser. No. 61/355,832, the disclosure of which is incorporated by reference herein. Various other suitable ways in which articulation may be provided will be apparent to those of ordinary skill in the art in view of the teachings herein. In addition or in the alternative, shaft (100) may be rotatable about longitudinal axis (130), relative to handle portion (400), to selectively position end effector (200) at various angular orientations about longitudinal axis (130). Of course, a user may rotate the entire instrument (10) about longitudinal axis (130) to selectively position end effector (200) at various angular orientations about longitudinal axis (130).

End effector (200) of the present example includes a first grasping arm (210) and a second grasping arm (250). As will be described in greater detail below, arms (210, 250) are configured to alternatingly throw and catch a curved suturing needle (50) along a path/plane that is substantially perpendicular to longitudinal axis (130) defined by shaft (100). Alternatively, arms (210, 250) may be configured to alternatingly throw and catch needle (50) along a path that is substantially parallel to longitudinal axis (130) defined by shaft (100); or along some other path.

In some versions, arms (210, 250) pass needle (50) back and forth from arm (210) to arm (250) and from arm (250) to arm (210) in an oscillating motion (i.e., back and forth in opposite directions), such that needle (50) does not traverse a circular path as needle (50) is being passed between arms (210, 250). Such action of needle (50) may be referred to as a "reverse reset." In some other versions, needle (50) may be passed between arms (210, 250) along a circular path in a single direction. Such action of needle (50) may be referred to as a "forward reset." By way of example only, arms (210, 250) may move in accordance with at least some of the teachings of U.S. Provisional Patent Application No. 61/355,832, the disclosure of which is incorporated by reference herein; and/or in accordance with at least some of the teachings of U.S. Pat. Pub. No. 2011/0313433, entitled "Laparoscopic Suture Device with Asynchronous In-Line Needle Movement," published Dec. 22, 2011, now U.S. Pat. No. 9,168,037, issued on Oct. 27, 2015, the disclosure of which is incorporated by reference herein. Regardless of whether arms (210, 250) move synchronously or asynchronously, arms (210, 250) may be configured to grip and/or compress tissue that is positioned between arms (210, 250) when arms are in approximated positions, which may facilitate passage of needle (50) through the tissue.

Needle (50) of the present example includes a sharp tip (52) (shown in FIG. 2A), a blunt end (54) (shown in FIG. 2C), and a pair of grasping regions (56, 58) (shown in FIGS. 2A, 2C) configured for grasping by arms (210, 250). In particular, grasping regions (56, 58) comprise scallops in the present example, though it should be understood that grasping regions (56, 58) may have various other configurations.

A suture (60) (shown in FIGS. 5A-5H) is secured to a mid-region of needle (50). The configuration and relationship of suture (60) and needle (50) provides an exit of suture (60) from needle (50) at an angle that is generally tangent to or oblique relative to the curvature of needle (50). Such an angle may provide reduced drag forces and/or reduced tissue trauma as compared to drag forces and/or tissue trauma that might otherwise be encountered using a needle with a suture that exits at a generally perpendicular angle.

While the example described below includes just a single strand of suture (60) extending from needle (50), it should be understood that two or more strands (60) may extend from needle (50) (e.g., double leg suture, etc.). As yet another merely illustrative example, suture (60) may be secured to blunt end (54) of needle (50) instead of being secured to a mid-region of needle (50). In still other versions, end (54) includes a sharp tip instead of being blunt. It should also be understood that needle (50) may be straight instead of curved in some versions. By way of example only, needle (50) may be constructed in accordance with at least some of the teachings of U.S. Provisional Application Ser. No. 61/413,680; U.S. patent application Ser. No. 13/295,186, entitled "Needle for Laparoscopic Suturing Instrument," filed Nov. 14, 2011, now U.S. Pat. No. 9,125,646, issued on Sep. 8, 2015; U.S. Pat. No. 6,056,771, entitled "Radiused Tip Surgical Needles and Surgical Incision Members," issued May 2, 2000; and/or U.S. Pat. Pub. No. 2010/0100125, entitled "Suture Needle and Suture Assembly," published Apr. 22, 2010, the disclosures of which are incorporated by reference herein. Still other suitable configurations for needle (50) will be apparent to those of ordinary skill in the art in view of the teachings herein.

It should also be understood that needle (50) may be constructed using various techniques. By way of example only, needle (50) may be constructed using metal-injection-molding (MIM) processes. Needle (50) may also be formed from a sheet, wire, tube, extrusion, or other components that are bent, stamped, coined, milled, otherwise machined, and/or otherwise formed. Other suitable ways in which needle (50) may be constructed will be apparent to those of ordinary skill in the art in view of the teachings herein.

II. Exemplary End Effector

As noted above, end effector (200) comprises a pair of grasping arms (210, 250) that are operable to selectively grasp needle (50) during a suturing procedure. Grasping arms (210, 250) are exposed relative to an endcap (102) of shaft (100), shown in FIGS. 2A-2C. Each grasping arm (210, 250) extends along a respective axis that is parallel to yet offset from longitudinal axis (130) of shaft (100), shown in FIGS. 5A-5H. First grasping arm (210) maintains a fixed rotational position relative to shaft (100) during operation of instrument (10) in the present example. In some other versions, first grasping arm (210) is rotatable about its own longitudinal axis, relative to shaft (100). Second grasping arm (250) of the present example is rotatable about its longitudinal axis (140). Such motion can be seen in the series shown by FIGS. 2A-2C.

Figure 2B:
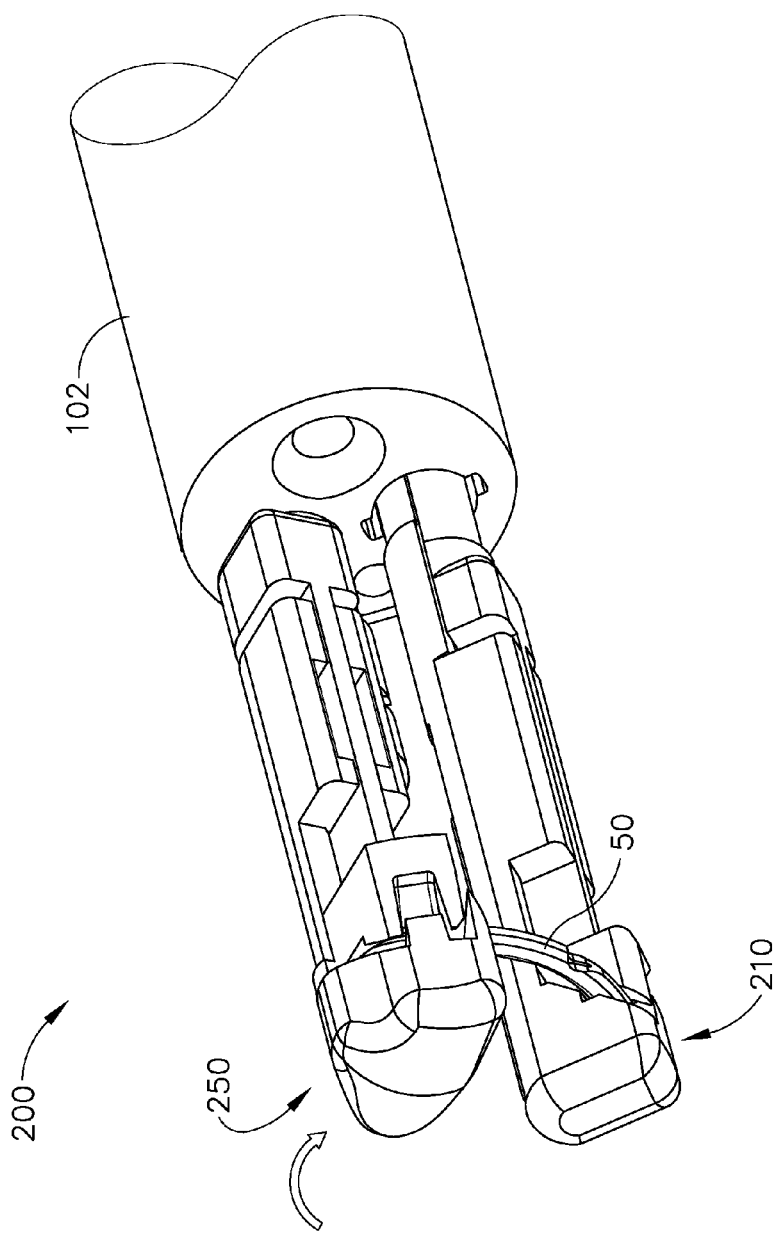
FIG. 2B depicts a perspective view of the end effector and needle of FIG. 2A, in a second operational configuration.

FIG. 2A shows first grasping arm (210) grasping needle (50), with second grasping arm (250) rotated away from needle (50), exposing sharp tip (52) of needle (50). FIG. 2B shows second grasping arm (250) rotated toward needle (50) to a position enabling second grasping arm (250) to grasp needle (50) and first grasping arm (210) to release needle (50). FIG. 2C shows second grasping arm (250) rotated away from first grasping arm (210), pulling needle (50) away from second grasping arm (250). After reaching this position, second grasping arm (250) may be rotated back to the position shown in FIG. 2B, to thereby pass needle (50) back to first grasping arm (210); then rotated back to the position shown in FIG. 2A to start the cycle over again.

In the examples described herein, needle (50) is driven along a plane that is substantially perpendicular to longitudinal axis (130) of shaft (100). In some other examples, needle (50) is driven along a plane that is oblique relative to longitudinal axis (130) of shaft (100) or substantially parallel to longitudinal axis (130) of shaft (100). During some uses of instrument (10), needle (50) may deviate from the desired perpendicular plane. Such deviation may be due to manufacturing tolerances, deflections caused by tissue or other structures, and/or for other reasons. Such deviation may be accentuated by using a needle (50) having a relatively great length. As will be described below, end effector (200) of the present example is configured to readily accommodate and correct such off-plane deviations. In other words, arms (210, 250) are operable to grasp needle (50) even in instances where needle (50) has deviated away from the expected perpendicular plane of motion; and arms (210, 250) are further operable to redirect a deviated needle (50) back onto the expected perpendicular plane of motion.

It should be noted that suture (60) is omitted from FIGS. 2A-2C for clarity. Various components of grasping arms (210, 250) will be described in greater detail below. Various ways in which grasping arms (210, 250) may be used will also be described in greater detail below. Other suitable components of and uses for grasping arms (210, 250) will be apparent to those of ordinary skill in the art in view of the teachings herein.

A. Exemplary First Grasping Arm

Figure 3A:
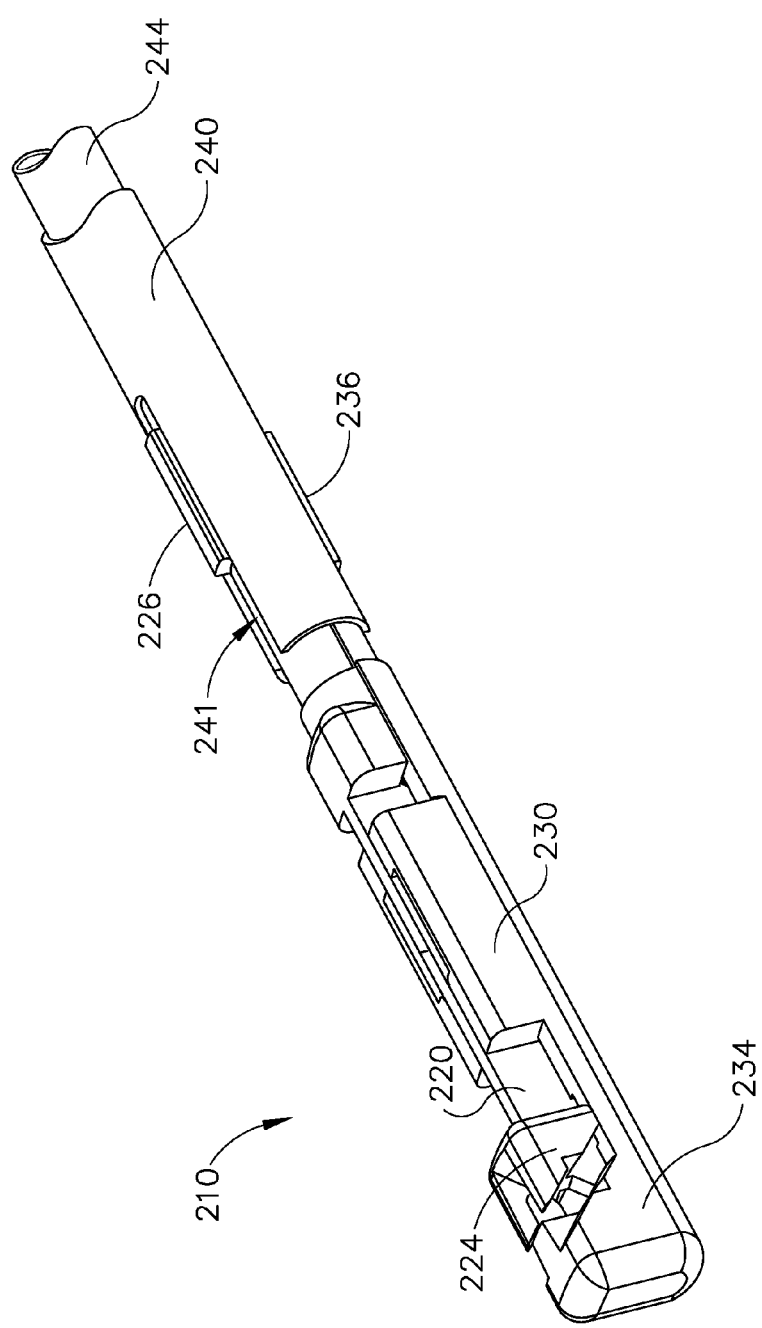
FIG. 3A depicts a first partial perspective view of a first needle grasping arm of the end effector of FIG. 2A
Figure 3B:
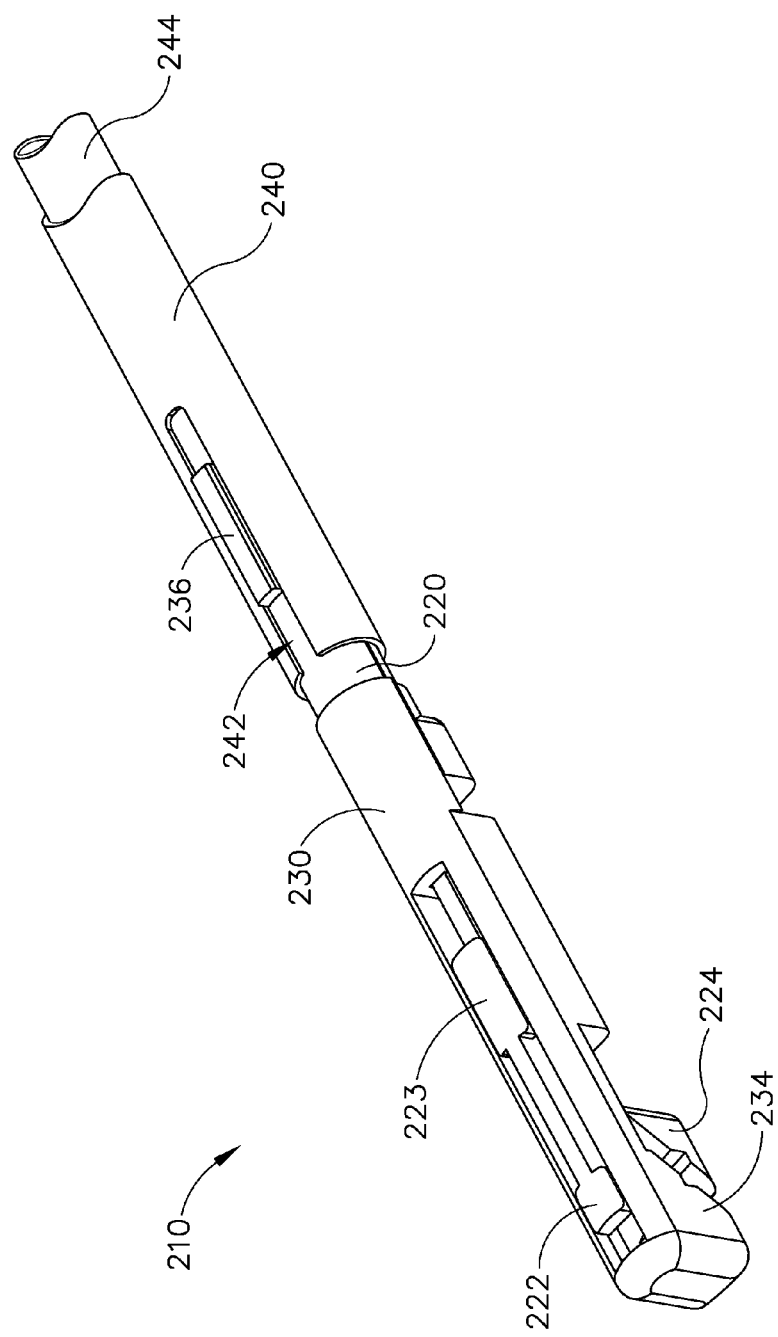
FIG. 3B depicts a second partial perspective view of the first needle grasping arm of FIG. 3A.
Figure 3C:
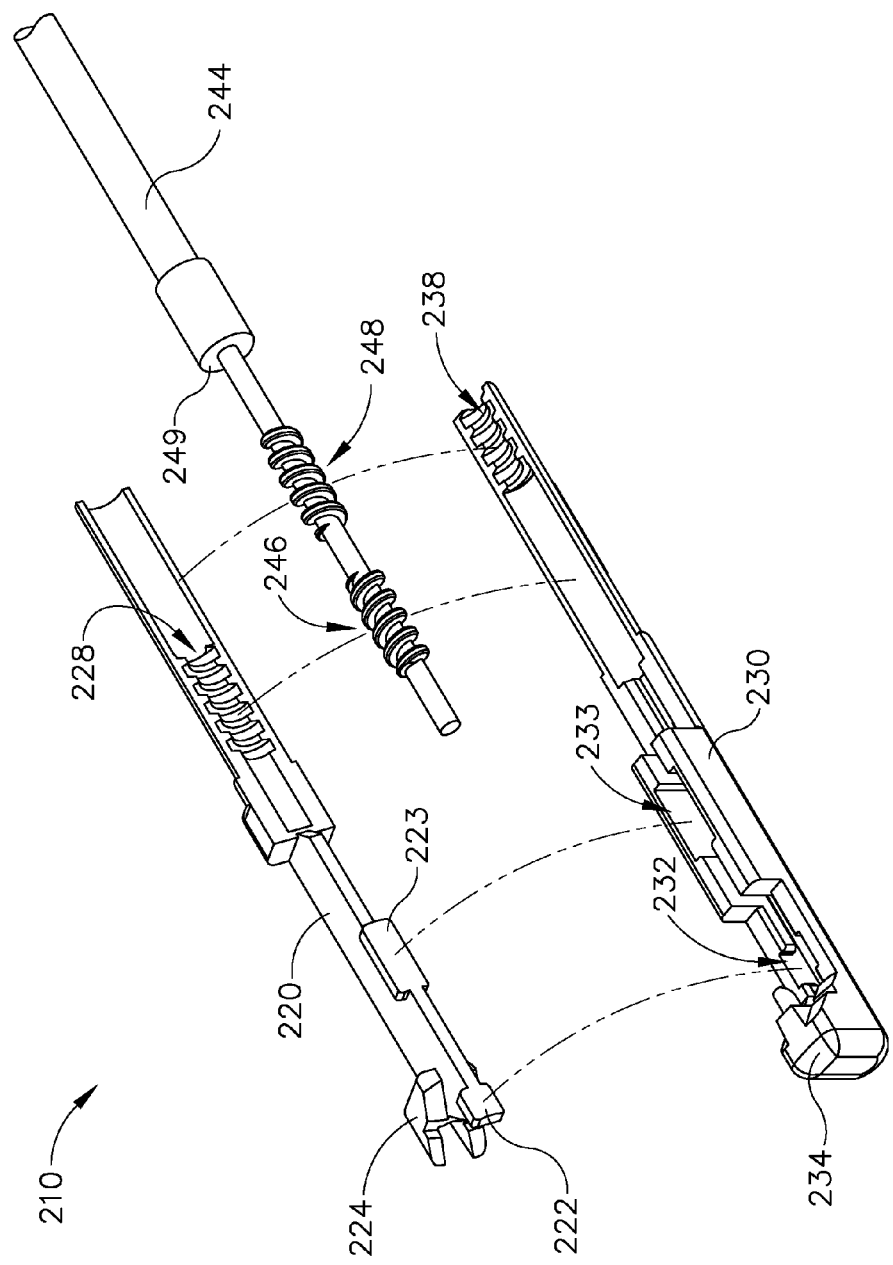
FIG. 3C depicts a partial exploded view of the first needle grasping arm of FIG. 3A.

FIGS. 3A-3C show an exploded view of a first grasping arm (210) in greater detail. First grasping arm (210) comprises a first jaw (220) and a second jaw (230). Referring to FIGS. 3A-3B, jaws (220, 230) substantially align with each other and are slidable longitudinally relative to each other. As shown in FIG. 3B, jaw (220) includes a pair of flanges (222, 223) that are received through corresponding openings (232, 233) of second jaw (230) during assembly of arm (210). Thereafter, flanges (222, 223) substantially prevent jaws (220, 230) from deflecting transversely away from each other. Jaws (220, 230) also include complementary needle grasping features (224, 234) that are configured to selectively grasp needle (50) as will be described in greater detail below. The proximal portion of jaws (220, 230) each includes a transversely extending fin (226, 236). Fins (226, 236) are slidably disposed in corresponding distal slots (241, 242) of a sheath (240) (shown in FIG. 6). Sheath (240) extends along the length of shaft (100) and is substantially fixed within shaft (100). In particular, sheath (240) does not rotate or translate relative to shaft (100) in this example. Sheath (240) thus provides a mechanical ground in the angular direction. It should therefore be understood that the relationship between fins (226, 236) and slots (241, 242) prevent first grasping arm (210) from rotating relative to shaft (100). In some other versions, however, first grasping arm (210) is rotatable relative to shaft (100) (e.g., by rotating sheath (240) within shaft (100), etc.). It should also be understood that, in the present example, the relationship between fins (226, 236) and slots (241, 242) still permits jaws (220, 230) to translate relative to sheath (240) and shaft (100).

Jaws (220, 230) of the present example are simultaneously movable in opposite directions to selectively expand or reduce an opening formed by grasping features (224, 234) to receive needle (50). To open and receive needle (50), first jaw (220) moves proximally toward shaft (100) and second jaw (230) simultaneously moves distally away from shaft (100) to enlarge the opening defined by grasping features (224, 234) to receive needle (50). To close and grip needle (50), first jaw (220) has moved distally away from shaft (100) and second jaw (230) has simultaneously moved proximally toward shaft (100) to reduce the opening defined by grasping features (224, 234) to securely grasp needle (50). In some versions, one jaw (220, 230) remains longitudinally stationary while the other jaw translates longitudinally to grasp or release needle (50) between grasping features (224, 234). However, it should be understood that in versions such as the present example where jaws (220, 230) both move simultaneously in opposite directions, such motion may further promote alignment of needle (50) within grasping features (224, 234) as compared to versions where one jaw (220, 230) always stays longitudinally fixed relative to shaft (100). In other words, having both grasping features (224, 234) always spaced equidistantly away from the intended path of needle (50) (regardless of whether jaws (220, 230) are open or closed) may better accommodate incidental deflections of needle (50) away from that intended path in either direction during use of instrument (10). Arm (210) may thus be particularly suited to accommodate instances where needle (50) has deviated away from the expected perpendicular plane of motion as described above.

As shown in FIG. 3C, to provide the simultaneous opposing motion of jaws (220, 230), a first drive shaft (244) includes a first threaded section (246) and a second threaded section (248). First drive shaft (244) is coaxially positioned within sheath (240), shown in FIG. 6, and is rotatable within sheath (240). First drive shaft (244) of the present example is rotatably driven from within handle portion (400), as will be discussed in greater detail below. The threading of first threaded section (246) is oriented opposite to the threading of second threaded section (248), such that threaded sections (246, 248) have opposite pitches. The proximal portions of jaws (220, 230) together encompass the distal portion of first drive shaft (244). In particular, the proximal portion of first jaw (220) includes threading (228) that meshes with first threaded section (246); while the proximal portion of second jaw (230) includes threading (238) that meshes with second threaded section (248). It should therefore be understood that threading (228) has a pitch that is opposite to the pitch of threading (238). It should also be understood that, due to the relationships and orientations of threaded sections (246, 248) and threading (228, 238), first drive shaft (244) will cause jaws (220, 230) to simultaneously translate away from each other when first drive shaft (244) is rotated in one direction; while first drive shaft (244) will cause jaws (220, 230) to simultaneously translate toward each other when first drive shaft (244) is rotated in the other direction.

It should be understood that the opposing-thread configuration described above may require relatively low torsional force to rotate first drive shaft (244) to drive jaws (220, 230) toward and away from each other. It should also be understood that the opposing-thread configuration described above may provide a relatively high holding force. For instance, when needle grasping features (224, 234) are driven toward each other to secure needle (50) and needle (50) is off-plane for whatever reason (e.g., incidentally oriented slightly obliquely relative to longitudinal axis (130) of shaft (100), etc.), the needle holding forces at grasping features (224, 234) may be self-reinforcing due to opposing forces provided through the opposing thread configuration described above, providing a mechanical advantage to urge needle (50) back into the desired planar orientation, even if tissue or some other structure is resisting such movement of needle (50) into the desired planar orientation. Similarly, the opposing thread configuration described above may provide friction that acts as an anti-backup feature, substantially resisting inadvertent separation of grasping features (224, 234), thereby providing a very secure hold of needle (50). Other suitable components that may be used to provide opposing motion of grasping features (224, 234) (e.g., a pinion with opposing racks, etc.) will be apparent to those of ordinary skill in the art in view of the teachings herein.

It should also be understood that, while first drive shaft (244) rotates about an axis that is parallel to longitudinal axis (130) of shaft (100), alternative drive systems that include a rotary member may provide rotation of such a rotary member about an axis that is not parallel to longitudinal axis (130) of shaft (100). For instance, a pinion based drive system may provide rotation of a drive pinion about an axis that is perpendicular to longitudinal axis (130) of shaft (100). Other suitable ways in which jaws (220, 230) may be actuated will be apparent to those of ordinary skill in the art in view of the teachings herein. First grasping arm (210) may be further constructed in accordance with the teachings of U.S. patent application Ser. No. 13/295,203, entitled "Laparoscopic Suturing Instrument with Dual-Action Needle Graspers," filed Nov. 11, 2011, now U.S. Pat. No. 8,702,732, issued Apr. 22, 2014, and/or U.S. patent application Ser. No. 13/295,210, entitled "Laparoscopic Suturing Instrument with Perpendicular Eccentric Needle Motion," filed Nov. 11, 2011, now U.S. Pat. No. 8,906,043, issued on Dec. 9, 2014, the disclosures of which are incorporated by reference herein.

B. Exemplary Second Grasping Arm

Figure 4A:
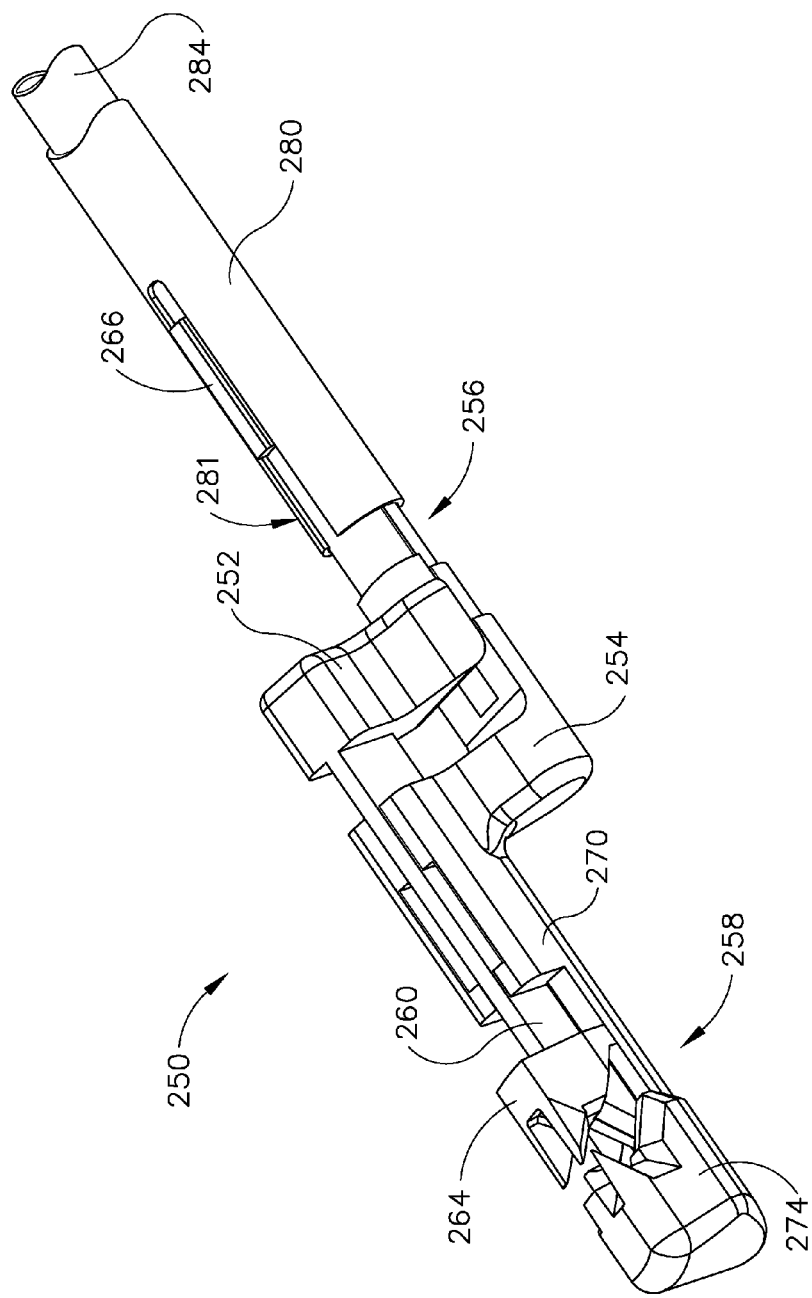
FIG. 4A depicts a first partial perspective view of a second needle grasping arm of the end effector of FIG. 2A
Figure 4B:
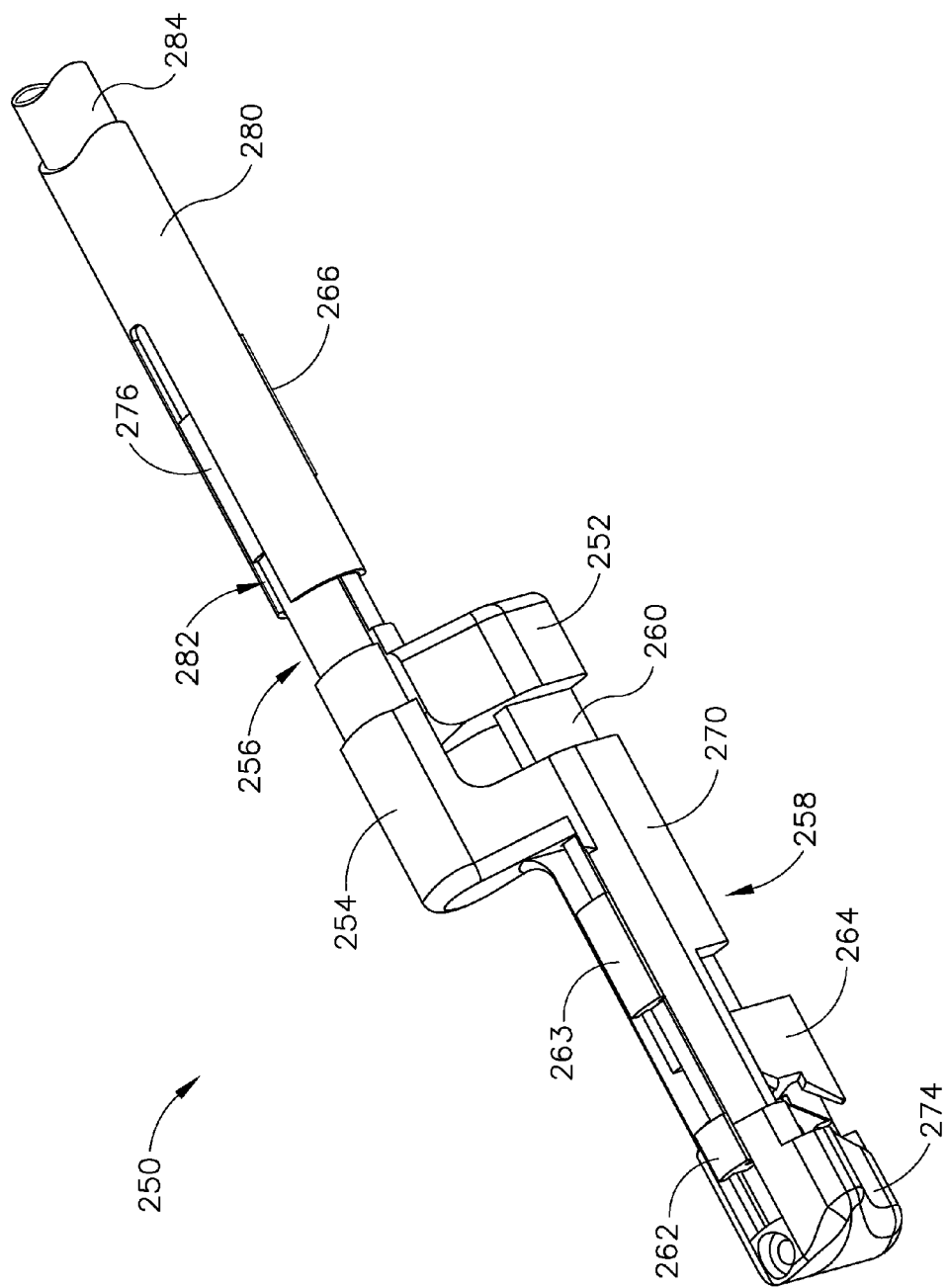
FIG. 4B depicts a second partial perspective view of the second needle grasping arm of FIG. 4A.
Figure 4C:
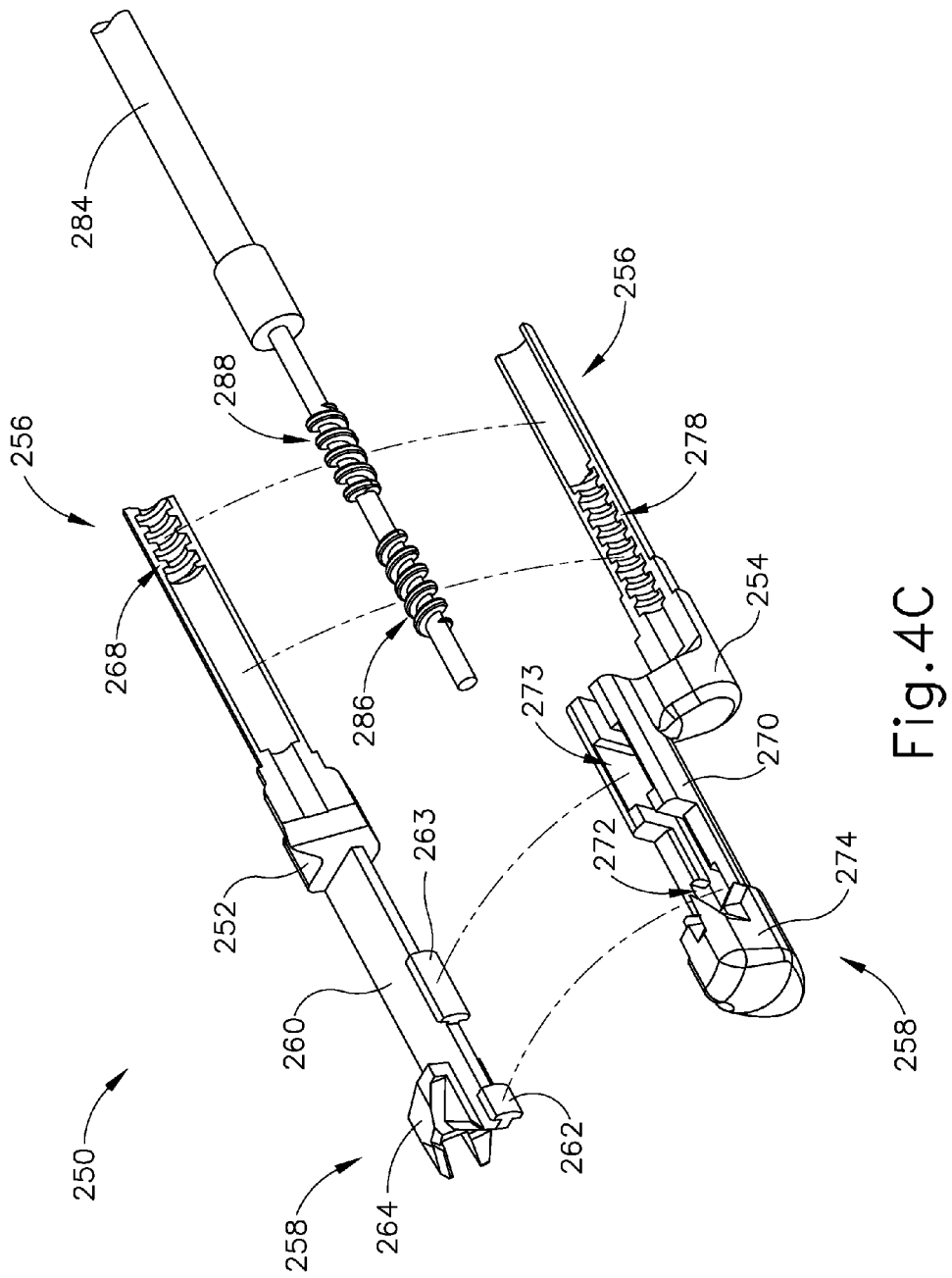
FIG. 4C depicts a partial exploded view of the second needle grasping arm of FIG. 4A.

FIGS. 4A-4C show second grasping arm (250) in greater detail having a first jaw (260) and a second jaw (270). Referring initially to FIGS. 4A-4B, jaws (260, 270) substantially align with each other and are slidable longitudinally relative to each other. As shown in FIG. 4B, first jaw (260) includes a pair of flanges (262, 263) that are received through corresponding openings (272, 273) of second jaw (270) during assembly of arm (250). Thereafter, flanges (262, 263) prevent jaws (260, 270) from deflecting transversely away from each other. Jaws (260, 270) also include complementary needle grasping features (264, 274) that are configured to selectively grasp needle (50) as will be described in greater detail below. The proximal portion of each jaw (260) includes a transversely extending fin (266, 276). Fins (266, 276) are slidably disposed in corresponding distal slots (281, 282) of a sheath (280), shown in FIG. 6. Each jaw (260, 270) of second grasping arm (250) includes a dogleg section (252, 254). Each dogleg section (252, 254) forms a pair of right angles between a proximal portion (256) of grasping arm (250) and a distal portion (258) of grasping arm (250). The configuration of dogleg sections (252, 254) provides distal portion (258) in a parallel yet offset position relative to proximal portion (256). Thus, when grasping arm (250) is rotated about a longitudinal axis (140) extending along the length of the proximal portion (256) of grasping arm (250), the distal portion (258) of grasping arm (250) rotates in an orbital motion about that longitudinal axis (140). Such motion will be described in greater detail below.

Figure 6:
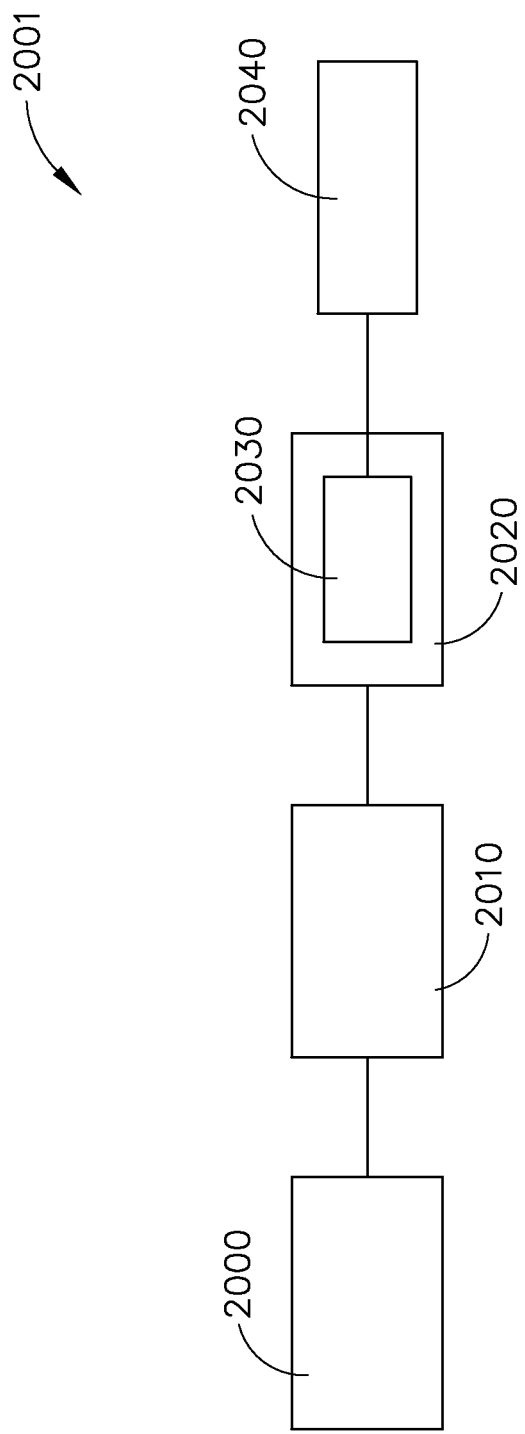
FIG. 6 depicts a block schematic of an exemplary surgical instrument control system.

Sheath (280), shown in FIG. 6, extends along the length of shaft (100) and is partially fixed within shaft (100). In particular, sheath (280) does not translate relative to shaft (100) in this example, though sheath (280) is rotatable relative to shaft (100). For instance, sheath (280) may be selectively rotated in either direction by a motor, trigger, actuator, and/or any other element as will be described in greater detail below. It should therefore be understood that rotation of sheath (280) relative to shaft (100) will provide rotation of second grasping arm (250) relative to shaft (100), due to the relationship between fins (266, 276) and slots (281, 282). As noted above, when second grasping arm (250) is rotated by sheath (280), the distal portion (258) of grasping arm (250) rotates in an orbital motion about longitudinal axis (140) that is defined by both sheath (280) and the proximal portion (256) of grasping arm (250). In some other versions, second grasping arm (250) is non-rotatable relative to shaft (100). It should also be understood that, in the present example, the relationship between fins (266, 276) and slots (281, 282) permits jaws (260, 270) to translate relative to sheath (280) and shaft (100).

In the present example, jaws (260, 270) are simultaneously movable in opposite directions to selectively expand or reduce an opening formed by grasping features (264, 274) to receive needle (50). To open and receive needle (50), first jaw (260) moves proximally toward shaft (100) and second jaw (270) simultaneously moves distally away from shaft (100) to enlarge the opening defined by grasping features (264, 274) to receive needle (50). To close and grip needle (50), first jaw (260) moves distally away from shaft (100) and second jaw (270) simultaneously moves proximally toward shaft (100) to reduce the opening defined by grasping features (264, 274) to securely grasp needle (50). In some versions, one jaw (260, 270) remains longitudinally stationary while the other jaw translates longitudinally to grasp or release needle (50) between grasping features (264, 274). However, it should be understood that in versions such as the present example where jaws (260, 270) both move simultaneously in opposite directions, such motion may further promote alignment of needle (50) within grasping features (264, 274) as compared to versions where one jaw (260, 270) always stays longitudinally fixed relative to shaft (100). In other words, having both grasping features (264, 274) always spaced equidistantly away from the intended path of needle (50) (regardless of whether jaws (260, 270) are open or closed) may better accommodate incidental deflections of needle (50) away from that intended path in either direction during use of instrument (10). Arm (250) may thus be particularly suited to accommodate instances where needle (50) has deviated away from the expected perpendicular plane of motion as described above.

As shown in FIG. 4C, to provide the simultaneous opposing motion of jaws (260, 270), a second drive shaft (284) that includes a first threaded section (286) and a second threaded section (288). Second drive shaft (284) is coaxially positioned within sheath (280) and is rotatable within sheath (280). Second drive shaft (284) of the present example is rotatably driven from within handle portion (400), as will be discussed in greater detail below. The threading of first threaded section (286) is oriented opposite to the threading of second threaded section (288), such that threaded sections (286, 288) have opposite pitches. The proximal portions of jaws (260, 270) together encompass the distal portion of drive shaft (284). In particular, the proximal portion of first jaw (260) includes threading (268) that meshes with first threaded section (286); while the proximal portion of second jaw (270) includes threading (278) that meshes with second threaded section (288). It should therefore be understood that threading (268) has a pitch that is opposite to the pitch of threading (278). It should also be understood that, due to the relationships and orientations of threaded sections (286, 288) and threading (268, 278), second drive shaft (284) will cause jaws (260, 270) to simultaneously translate away from each other when second drive shaft (284) is rotated in one direction; while second drive shaft (284) will cause jaws (260, 270) to simultaneously translate toward each other when second drive shaft (284) is rotated in the other direction.

In some settings, the rotational position of sheath (280) is fixed relative to shaft (100) when second drive shaft (284) is rotated relative to shaft (100). Thus, sheath (280) substantially holds the rotational position of jaws (260, 270) when second drive shaft (284) is rotated. In some other settings, sheath (280) and second drive shaft (284) are rotated simultaneously relative to shaft (100). In some such instances, sheath (280) and second drive shaft (284) are rotated in the same direction and at the same speed, such that second drive shaft (284) and jaws (260, 270) are rotated in the same direction and at the same speed. Thus, the longitudinal positioning of jaws (260, 270) remains fixed during such rotation. As another merely illustrative variation, sheath (280) and second drive shaft (284) may be rotated simultaneously relative to shaft (100), but at different speeds and/or in different directions. Such a scheme provides a rotation differential between jaws (260, 270) and second drive shaft (284), such that jaws (260, 270) may open or close while second grasping arm (250) is simultaneously being rotated relative to shaft (100).

It should be understood that the opposing thread configuration described above may require relatively low torsional force to rotate second drive shaft (284) to drive jaws (260, 270) toward and away from each other. It should also be understood that the opposing thread configuration described above may provide a relatively high holding force. For instance, when needle grasping features (264, 274) are driven toward each other to secure needle (50) and needle (50) is off-plane for whatever reason (e.g., incidentally oriented slightly obliquely relative to longitudinal axis (130) of shaft (100), etc.), the needle holding forces at grasping features (264, 274) may be self-reinforcing due to opposing forces provided through the opposing thread configuration described above, providing a mechanical advantage to urge needle (50) back into the desired planar orientation, even if tissue or some other structure is resisting such movement of needle (50) into the desired planar orientation. Similarly, the opposing thread configuration described above may provide friction that acts as an anti-backup feature, substantially resisting inadvertent separation of grasping features (264, 274), thereby providing a very secure hold of needle (50). Other suitable components that may be used to provide opposing motion of grasping features (264, 274) (e.g., a pinion with opposing racks, etc.) will be apparent to those of ordinary skill in the art in view of the teachings herein.

It should also be understood that, while second drive shaft (284) rotates about a longitudinal axis (140) that is parallel to longitudinal axis (130) of shaft (100), alternative drive systems that include a rotary member may provide rotation of such a rotary member about an axis that is not parallel to longitudinal axis (130) of shaft (100). For instance, a pinion based drive system may provide rotation of a drive pinion about an axis that is perpendicular to longitudinal axis (130) of shaft (100). Other suitable ways in which one or more components of second grasping arm (250) may be actuated will be apparent to those of ordinary skill in the art in view of the teachings herein. Second grasping arm (250) may be further constructed in accordance with the teachings of U.S. patent application Ser. No. 13/295,203, entitled "Laparoscopic Suturing Instrument with Dual-Action Needle Graspers," filed Nov. 11, 2011, now U.S. Pat. No. 8,702,732, issued Apr. 22, 2014, and/or U.S. patent application Ser. No. 13/295,210, entitled "Laparoscopic Suturing Instrument with Perpendicular Eccentric Needle Motion," filed Nov. 11, 2011, now U.S. Pat. No. 8,906,043, issued on Dec. 9, 2014, the disclosures of which are incorporated by reference herein.

III. Exemplary Operation of End Effector

Figure 5A:
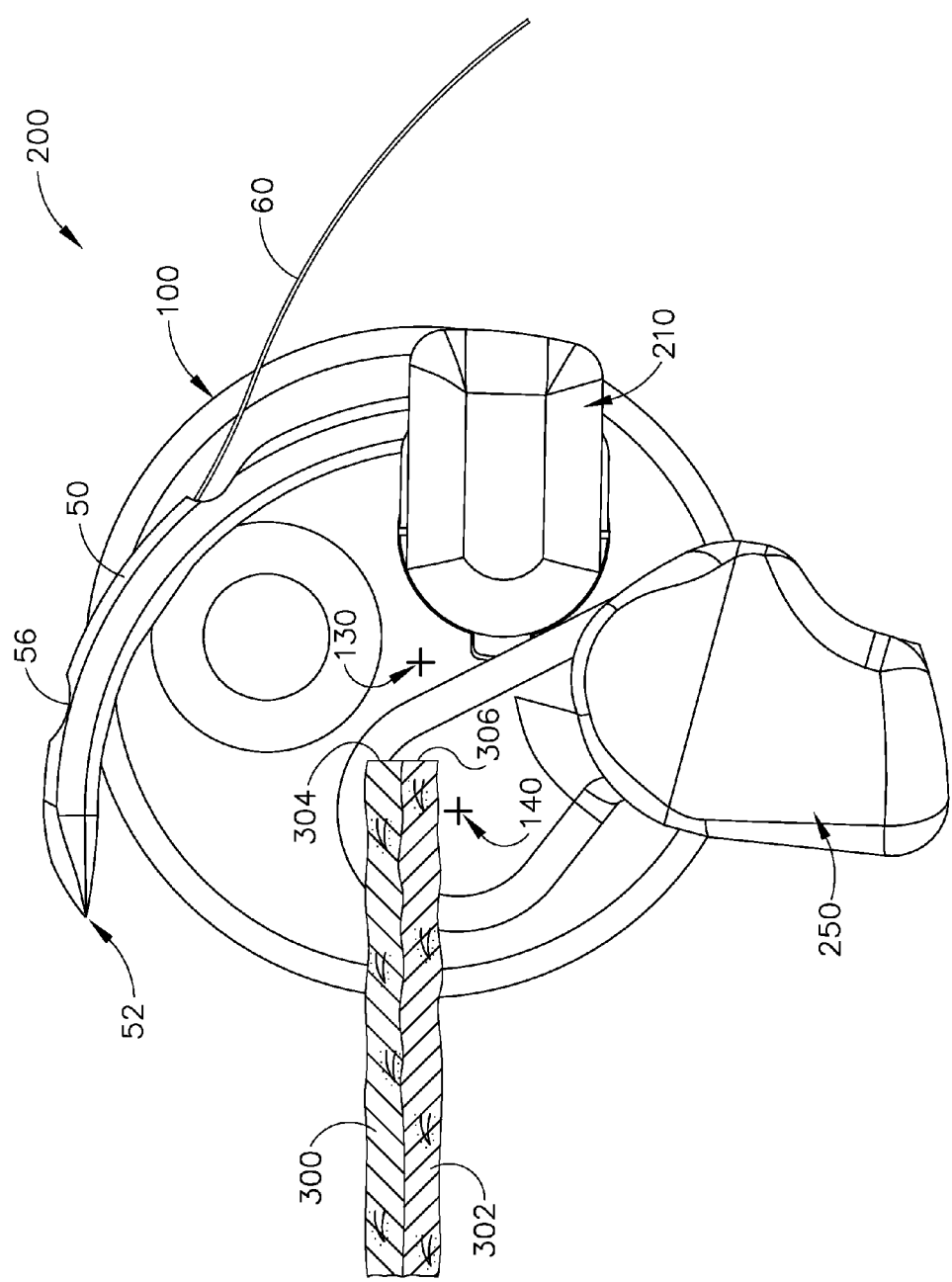
FIG. 5A depicts an end elevation view of the end effector and needle of FIG. 2A, during an exemplary first stage of operation.

FIGS. 5A-5H depict a merely exemplary method for using surgical instrument (10). In particular, FIG. 5A shows end effector (200) positioned adjacent to apposed layers (300, 302) of tissue. End effector (200) is positioned such that longitudinal axis (130) of shaft (100) is substantially parallel to the outer edges (304, 306) of tissue layers (300, 302). In this sense, "substantially parallel" simply means that end effector (200) is oriented in relation to tissue layers (300, 302) in a manner sufficient to enable needle (50) to be passed through tissue layers (300, 302). It should therefore be understood that longitudinal axis (130) need not necessarily be truly parallel with outer edges (304, 306), though longitudinal axis (130) may in fact be truly parallel with outer edges (304, 306) in some instances. It should also be understood that instrument (10) and needle (50) may be used to secure tissue together in an edge-to-edge arrangement rather than securing apposed layers (300, 302) as shown. Other suitable settings in which instrument (10) and needle (50) may be used will be apparent to those of ordinary skill in the art in view of the teachings herein. It should also be understood that the curved configuration of needle (50) may provide a more intuitive operation for the surgeon than a straight needle would, such as by providing better predictability for where sharp tip (52) will come through tissue.

Figure 5B:
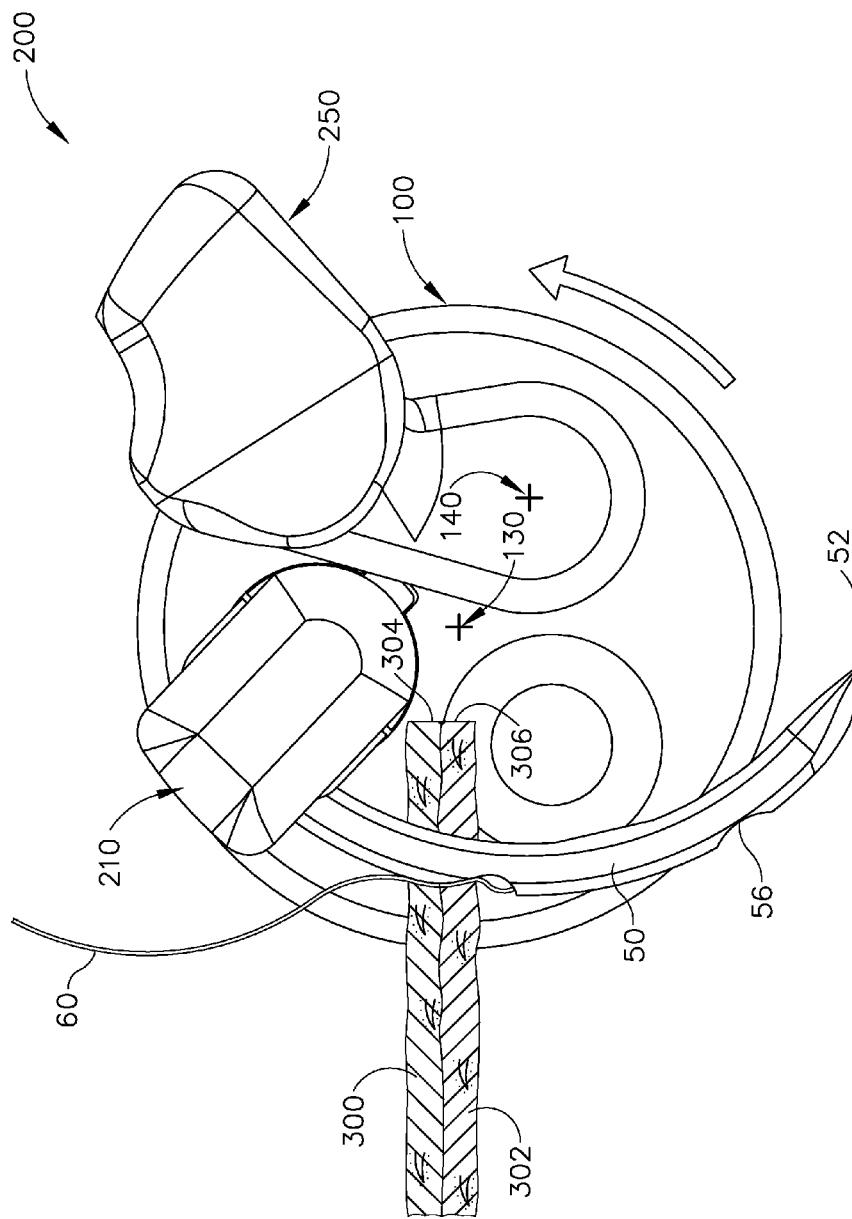
FIG. 5B depicts an end elevation view of the end effector and needle of FIG. 2A, during an exemplary second stage of operation.

As shown in FIG. 5A, first grasping arm (210) is securely holding needle (50), with sharp tip (52) exposed. In particular, grasping portions (224, 234) of jaws (220, 230) hold needle (50) at grasping region (56). Needle (50) is oriented along a plane that is substantially transverse to longitudinal axis (130). Once end effector (200) has been positioned as shown in FIG. 5A, the entire instrument (10) is rotated about longitudinal axis (130) to drive sharp tip (52) through tissue layers (300, 302), as shown in FIG. 5B. In the example shown, the rotational direction for instrument (10) is counterclockwise viewed from the distal end toward the proximal end, though it should be understood that instrument (10) may be rotated clockwise instead (e.g., depending on the orientation of sharp tip (52)). During the transition from the position of FIG. 5A to the position of FIG. 5B, the rotational position of grasping arms (210, 250) relative to shaft (100) remains fixed, such that grasping arms (210, 250) rotate unitarily with shaft (100) about longitudinal axis (130). The longitudinal position of jaws (220, 230, 260, 270) also remains fixed during this transition. As can also be seen in FIG. 5B, needle (50) has started to pull suture (60) through tissue layers (300, 302) at this stage. It should be understood that, in the stages shown in FIGS. 5A-5B, grasping arms (210, 250) and needle (50) are in the same rotational positions relative to shaft (100) as shown in FIG. 2A. It should also be noted that the configuration of end effector (200) and needle (50) may provide the surgeon with enhanced visibility of sharp tip (52) exiting tissue layers (300, 302) during the transition from FIG. 5A to FIG. 5B, particularly with second grasping arm (250) being rotated out of the way at this stage.

Figure 5C:
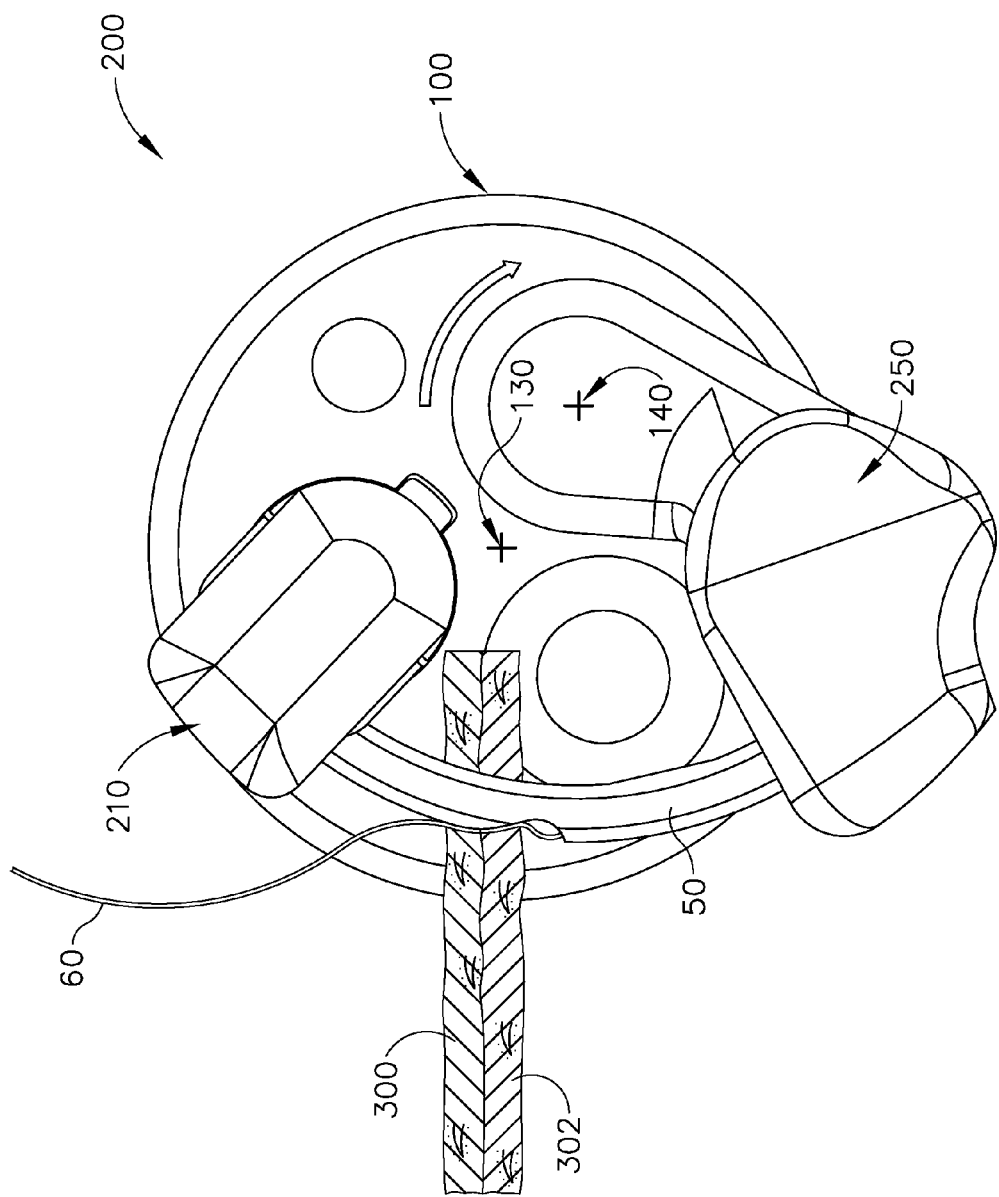
FIG. 5C depicts an end elevation view of the end effector and needle of FIG. 2A, during an exemplary third stage of operation.

After needle (50) has been driven at least partially through tissue layers (300, 302), second grasping arm (250) is rotated about its own axis (140) toward needle (50) as shown in FIG. 5C. Such rotation is provided by rotating sheath (280) relative to shaft (100). The rotational position of shaft (100) relative to longitudinal axis (130) remains fixed during the transition from the configuration shown in FIG. 5B to the configuration shown in FIG. 5C. It should be understood that, in the stage shown in FIG. 5C, grasping arms (210, 250) and needle (50) are in the same rotational positions relative to shaft (100) as shown in FIG. 2B.

In some versions, jaws (260, 270) are already opened by the time second grasping arm (250) starts rotating from the position shown in FIG. 5B to the position shown in FIG. 5C. In other versions, jaws (260, 270) are actively opened during the transition from the position shown in FIG. 5B to the position shown in FIG. 5C, such that jaws (260, 270) are fully open by the time second grasping arm (250) reaches the position shown in FIG. 5C. Once second grasping arm (250) reaches the position shown in FIG. 5C, jaws (260, 270) of second grasping arm (250) close to grasp needle (50) at grasping region (58) with grasping features (264, 274). In addition, jaws (220, 230) of first grasping arm (210) open to release needle (50) from grasping features (224, 234) at grasping region (56). In some versions, jaws (260, 270) of second grasping arm (250) close to grasp needle (50) at substantially the same time as jaws (220, 230) of first grasping needle (210) open to release needle (50). In some other versions, jaws (220, 230) of first grasping arm (210) do not open to release needle (50) until jaws (260, 270) of second grasping arm (250) have closed to grasp needle (50). Various suitable timing schemes and ways in which such schemes may be carried out will be apparent to those of ordinary skill in the art in view of the teachings herein.

Once control of needle (50) has been effectively passed from first grasping arm (210) to second grasping arm (250), second grasping arm (250) is rotated about longitudinal axis (140) to the position shown in FIG. 5D. Such rotation is provided by once again rotating sheath (280) relative to shaft (100), as will be described in greater detail below. The rotational position of shaft (100) relative to longitudinal axis (130) continues to be fixed during the transition from the configuration shown in FIG. 5C to the configuration shown in FIG. 5D. It should be understood that, in the stage shown in FIG. 5D, grasping arms (210, 250) and needle (50) are in the same rotational positions relative to shaft (100) as shown in FIG. 2C. As can also be seen in FIG. 5D, grasping arm (250) pulls suture (60) through tissue layers (300, 302) during the transition from FIG. 5C to FIG. 5D.

After reaching the configuration shown in FIG. 5D, the surgeon pulls the entire end effector (200) away from tissue layers (300, 302), along a path that is substantially transverse to longitudinal axis (130), as shown in FIG. 5E. It should be understood that this path may be oblique relative to longitudinal axis (130) and/or edges (304, 306), helical, and/or of any other suitable orientation. It should also be understood that neither arm (210, 250) is rotated relative to shaft (100) in the present example during the transition from the position shown in FIG. 5D to the position shown in FIG. 5E. Thus, in the stage shown in FIG. 5E, grasping arms (210, 250) and needle (50) are still in the same rotational positions relative to shaft (100) as shown in FIG. 2C. In moving instrument (10) away from tissue layers (300, 302) during the transition to the position shown in FIG. 5E, suture (60) is pulled further through tissue layers (300, 302).

Figure 5F:
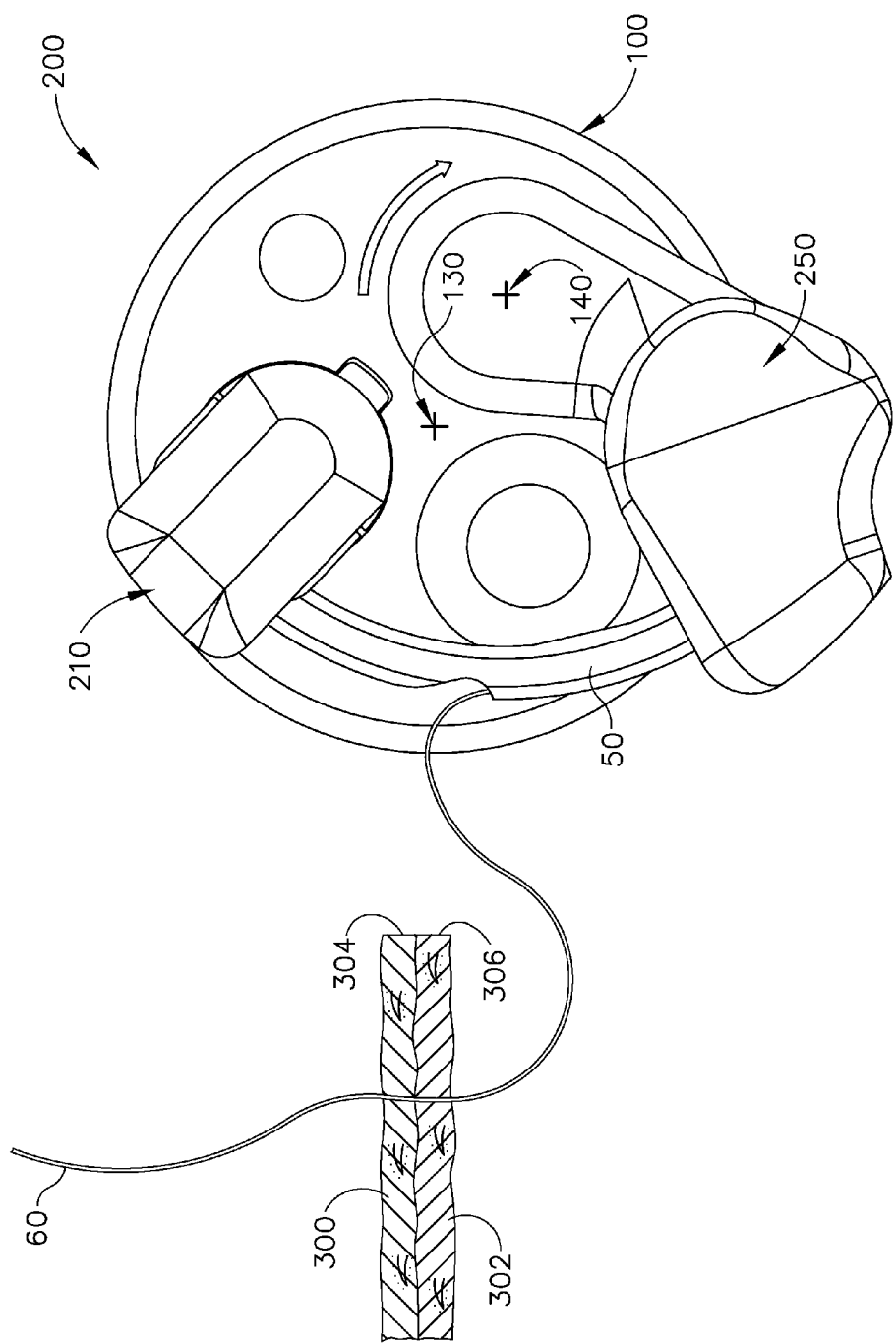
FIG. 5F depicts an end elevation view of the end effector and needle of FIG. 2A, during an exemplary sixth stage of operation.

With end effector (200) positioned sufficiently away from tissue layers (300, 302), second grasping arm (250) is rotated about longitudinal axis (140) to the position shown in FIG. 5F. The rotational position of shaft (100) relative to longitudinal axis (130) remains fixed during the transition from the configuration shown in FIG. 5E to the configuration shown in FIG. 5F. It should be understood that, in the stage shown in FIG. 5F, grasping arms (210, 250) and needle (50) are in the same rotational positions relative to shaft (100) as shown in FIG. 2B. End effector (200) is positioned far enough away from tissue layers (300, 302) during the transition from the position shown in FIG. 5E to the position shown in FIG. 5F such that blunt end (54) of needle (50) does not touch tissue layers (300, 302). The rotation of second grasping arm (250) to the position shown in FIG. 5F places grasping region (58) of needle (50) back between grasping portions (224, 234) of jaws (220, 230) of first grasping arm (210).

In some versions, jaws (220, 230) of first grasping arm (210) are already opened by the time second grasping arm (250) starts rotating from the position shown in FIG. 5E to the position shown in FIG. 5F. In other versions, jaws (220, 230) of first grasping arm (210) are actively opened during the transition from the position shown in FIG. 5E to the position shown in FIG. 5F, such that jaws (220, 230) are fully open by the time second grasping arm (250) reaches the position shown in FIG. 5F. Once second grasping arm (250) reaches the position shown in FIG. 5F, jaws (220, 230) of first grasping arm (210) close to grasp needle (50) at grasping region (56) with grasping portions (224, 234). In addition, jaws (260, 270) of second grasping arm (250) open to release needle (50) from grasping portions (264, 274) at grasping region (58). In some versions, jaws (220, 230) of first grasping arm (210) close to grasp needle (50) at substantially the same time as jaws (260, 270) of second grasping arm (250) open to release needle (50). In some other versions, jaws (260, 270) of second grasping arm (250) do not open to release needle (50) until jaws (220, 230) of first grasping arm (210) have closed to grasp needle (50). Various suitable timing schemes and ways in which such schemes may be carried out will be described in greater detail below while others will be apparent to those of ordinary skill in the art in view of the teachings herein.

Figure 5G:
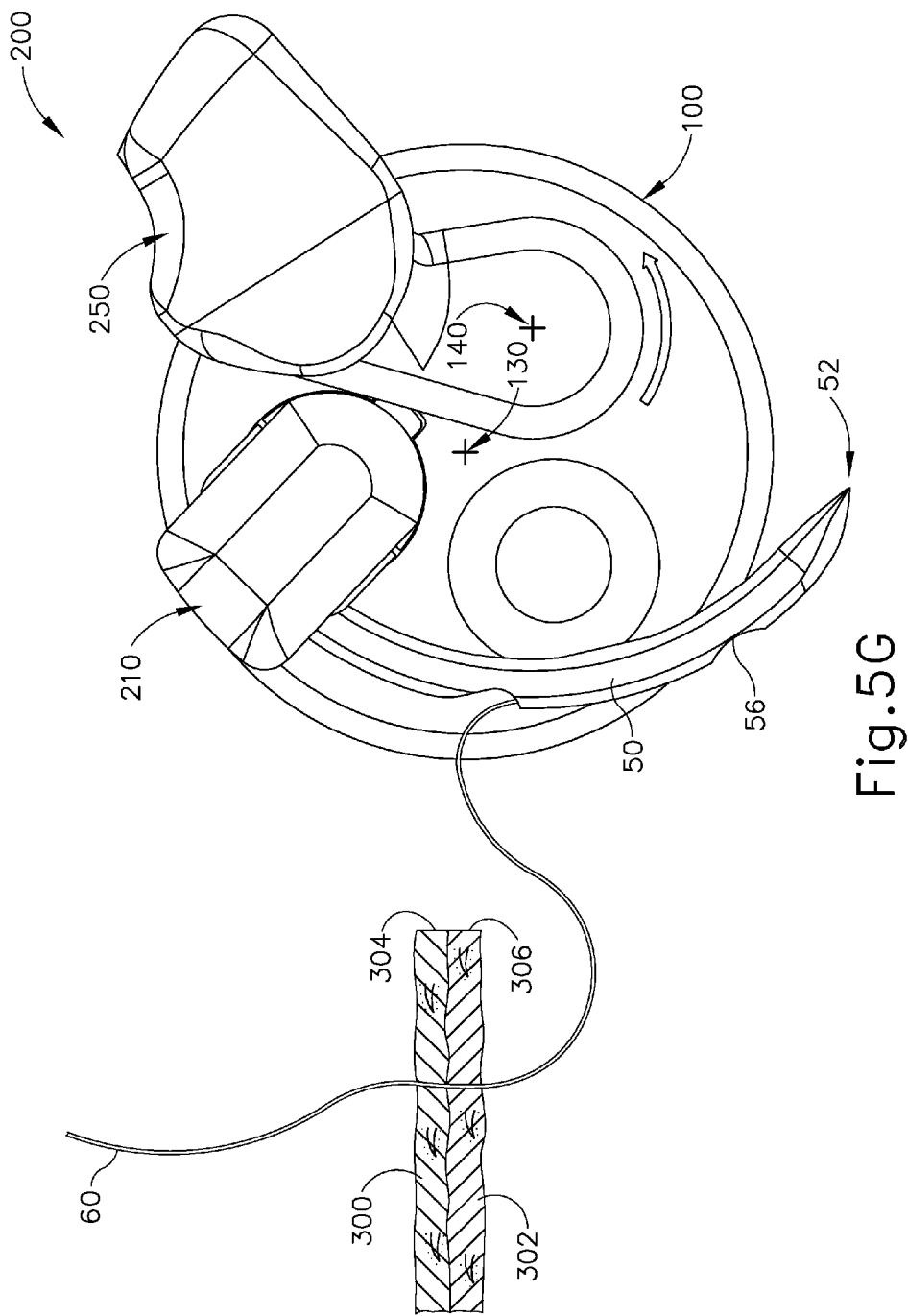
FIG. 5G depicts an end elevation view of the end effector and needle of FIG. 2A, during an exemplary seventh stage of operation.

Once control of needle (50) has been effectively passed from second grasping arm (250) back to first grasping arm (210), second grasping arm (250) is rotated about longitudinal axis (140) to the position shown in FIG. 5G. Such rotation is provided by once again rotating sheath (280) relative to shaft (100). The rotational position of shaft (100) relative to longitudinal axis (130) continues to be fixed during the transition from the position shown in FIG. 5F to the position shown in FIG. 5G. It should be understood that, in the stage shown in FIG. 5G, grasping arms (210, 250) and needle (50) are in the same rotational positions relative to shaft (100) as shown in FIG. 2A.

Figure 5H:
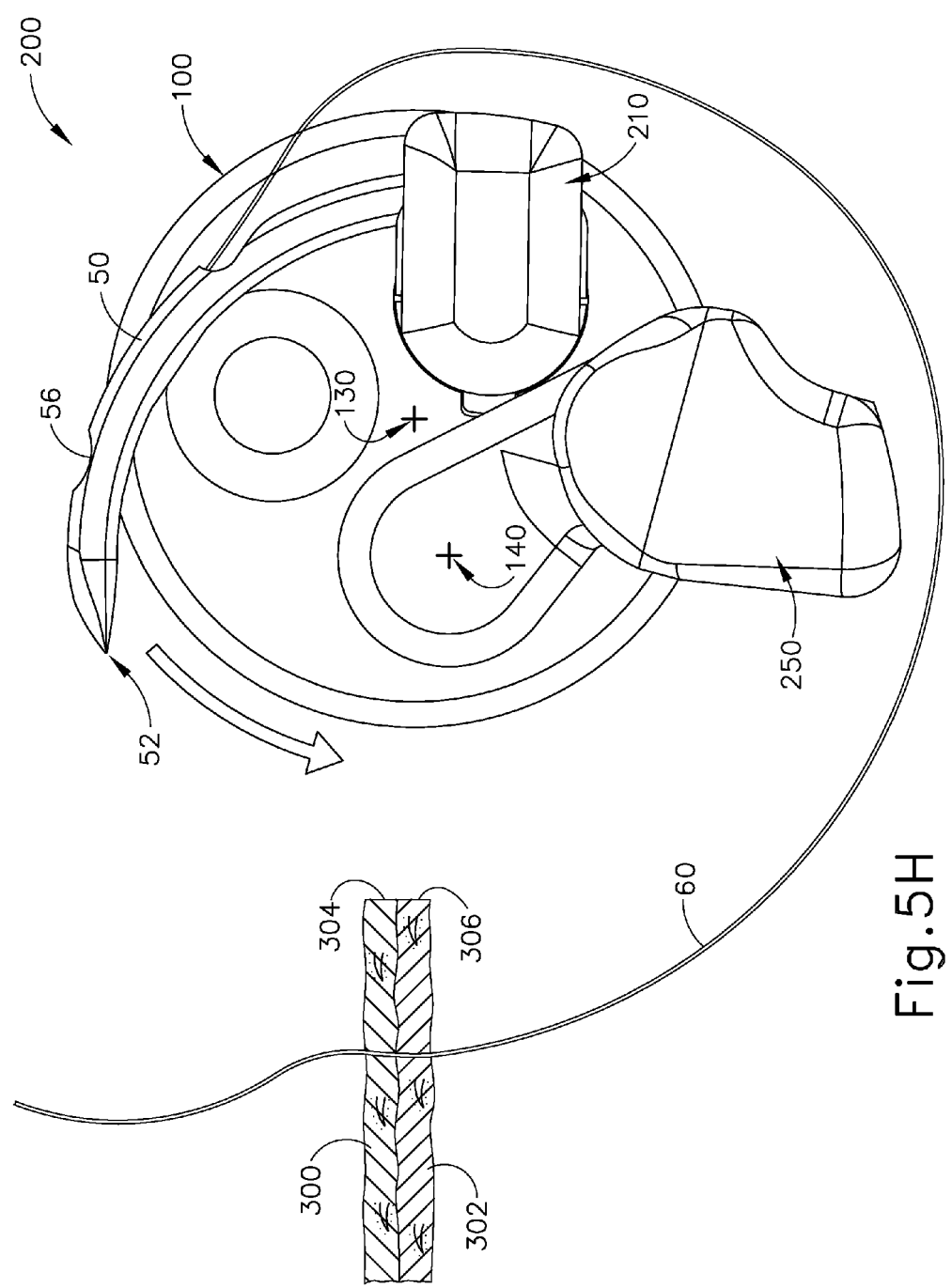
FIG. 5H depicts an end elevation view of the end effector and needle of FIG. 2A, during an exemplary eighth stage of operation.

Once second grasping arm (250) has been rotated away from needle (50) as shown in FIG. 5G, the entire instrument (10) is once again rotated about longitudinal axis (130) to position sharp tip (52) above tissue layers (300, 302), as shown in FIG. 5H. In the example shown, the rotational direction for instrument (10) is again counterclockwise viewed from the distal end toward the proximal end, though it should be understood that instrument (10) may be rotated clockwise instead (e.g., depending on the orientation of sharp tip (52)). During this transition, the rotational position of grasping arms (210, 250) relative to shaft (100) remains fixed, such that grasping arms (210, 250) rotate unitarily with shaft (100) about longitudinal axis (130). The longitudinal position of jaws (220, 230, 260, 270) also remains fixed during this transition. In the stage shown in FIG. 5H, grasping arms (210, 250) and needle (50) remain in the same rotational positions relative to shaft (100) as shown in FIG. 2A.

Having reached the configuration shown in FIG. 5H, end effector (200) may be moved back toward tissue layers (300, 302), such as along a path transverse to longitudinal axis (130), to again reach the position shown in FIG. 5A. The above described cycle may then be repeated as many times as desired until an appropriate number of stitches have been made through tissue layers (300, 302). The free end of suture (50) may then be knotted, clipped, or otherwise secured.

It should be understood that instrument (10) may be advanced distally or proximally along longitudinal axis (130) in each stitching cycle, each stitching cycle being represented by the succession of stages depicted in FIGS. 5A-5H. For instance, instrument (10) may be advanced distally or proximally along axis (130) during the transition from the position shown in FIG. 5E to the position shown in FIG. 5F. As another merely illustrative example, instrument (10) may be advanced distally or proximally along longitudinal axis (130) during the transition from the position shown in FIG. 5G to the position shown in FIG. 5H. Other suitable stages at which instrument (10) may be advanced distally or proximally will be apparent to those of ordinary skill in the art in view of the teachings herein. It should be understood that the distance of each incremental distal or proximal movement of instrument (10) during successive stitching cycles may be selected based on a desired stitch density along the length of the tissue being sutured. It should also be understood that, once stitching is complete, suture (60) may define a generally helical path through tissue layers (300, 302). Other suitable ways in which instrument (10) may be used will be apparent to those of ordinary skill in the art in view of the teachings herein.

As should be apparent to those of ordinary skill in the art, needle (50) of the present example orbits about longitudinal axis (140), which is offset from longitudinal axis (130) of shaft (100) in the present example. This may enable needle (50) to travel about an arc having a radius that is greater than the radius of a trocar through which shaft (100) is inserted. In other words, the circumferential path of needle (50) need not be limited to the circumference of the trocar through which shaft (100) is inserted when the orbital axis of needle (50) is offset from longitudinal axis (130) of shaft (100). Thus, the configuration of end effector (200) in the present example may permit a larger radius needle to be used, and larger stitches to be made, than what would be permitted if the orbital motion of needle (50) were centered about longitudinal axis (130) of shaft (100). In some other versions, needle (50) does move in an orbital fashion about longitudinal axis (130) of shaft (100). Surgical instrument (10) may be further operated in accordance with the teachings of U.S. patent application Ser. No. 13/295,203, entitled "Laparoscopic Suturing Instrument with Dual-Action Needle Graspers," filed Nov. 11, 2011, now U.S. Pat. No. 8,702,732, issued Apr. 22, 2014, and/or U.S. patent application Ser. No. 13/295,210, entitled "Laparoscopic Suturing Instrument with Perpendicular Eccentric Needle Motion," filed Nov. 11, 2011, now U.S. Pat. No. 8,906,043, issued on Dec. 9, 2014, the disclosures of which are incorporated by reference herein.

IV. Exemplary Shaft

As noted above, surgical instrument (10) comprises a shaft (100) extending between handle assembly (400) and end effector (100). As shown in FIG. 6, shaft (100) comprises an outer tubular member encasing a pair of sheaths (240, 280) and drive shafts (244, 284). In the present example, a first sheath (240) and first drive shaft (244) extend from handle assembly (400) to first grasping arm (210). First drive shaft (244) is coaxial to and nested within first sheath (240). As noted above, sheath (240) is mechanically ground in the angular direction relative to shaft (100) and first grasping arm (210) via fins (226, 236) and slots (241, 242) described above. Accordingly, sheath (240) remains in a first position while first drive shaft (244) is rotatable therein. When first drive shaft (244) is rotated a first direction, jaws (220, 230) of first grasping arm (210) simultaneously translate away from each other, thereby allowing first grasping arm (210) to receive or catch needle (50). When first drive shaft (244) is rotated in the other direction, jaws (220, 230) of first grasping arm (210) simultaneously translate toward each other, thereby grasping needle (50) with first grasping arm (210).

A second sheath (280) and second drive shaft (284) extend from handle assembly (400) to second grasping arm (250). Second drive shaft (284) is coaxial to and nested within second sheath (280). In the present example, second sheath (280) is mechanically ground in the angular direction relative second grasping arm (250) via fins (266, 276) and slots (281, 282) described above; however, in the present example, second sheath (280) is rotatable relative to shaft (100). Accordingly, second sheath (280) is operable to rotate second grasping arm (250) relative to shaft (100) when second sheath (280) is rotated. In the present example, second drive shaft (284) is rotatable within and relative to second sheath (280). Thus, when second drive shaft (284) is rotated a first direction, jaws (260, 270) of second grasping arm (250) simultaneously translate away from each other, thereby allowing second grasping arm (250) to receive or catch needle (50). When second drive shaft (284) is rotated in the other direction, jaws (260, 270) of second grasping arm (250) simultaneously translate toward each other, thereby grasping needle (50) with second grasping arm (250). In some instances, second drive shaft (284) and second sheath (280) may be simultaneously rotated together relative to shaft (100) to maintain jaws (260, 270) in a substantially fixed longitudinal position while second grasping arm (250) is rotated about longitudinal axis (140).

In some versions, shaft (100), first sheath (240), and/or second sheath (280) may include one or more bushings along a corresponding longitudinal axis (130, 140) to support first sheath (240) and/or second sheath (280) while still permitting rotation of first sheath (240) and/or second sheath (280) relative to shaft (100). By way of example only, such bushings may comprise a plurality of thermoplastic parts disposed about first sheath (240) and/or second sheath (280) at predetermined longitudinal positions. In addition, or in the alternative, shaft (100) may include interiorly mounted bushings. Of course other features and/or components may be used instead of bushings, such as bearings, pillow blocks, etc.

It should be understood that the foregoing description of the mechanical linkage of handle assembly (20) to end effector (200) is merely exemplary and other components and/or assemblies will be apparent to one of ordinary skill in the art in view of the teachings herein. For example, drive shafts (244, 284) may comprise resilient or bendable drive shafts. In some versions, one or more motors or actuators may be situated proximal to end effector (200) and coupled to one or more of sheaths (240, 280) and/or drive shafts (244, 284) to effect rotation. In such a version, a rotational sensor (not shown) may be disposed within handle assembly (20) to transmit instructions to the one or more motors or actuators. Still other configurations will be apparent to one of ordinary skill in the art in view of the teachings herein.

V. Exemplary Surgical Instrument Control System

While the above examples are described in the context of drive components being located in handle assembly (20), in some instances it may be desirable to control end effector (200) (seen for example, in FIG. 1) through a means other than controls located on handle portion (20). For example, a different device having a different form factor may be desirable for use while keeping the functionality of end effector (200). For instance, in some situations, it may be desirable to have a machine operate end effector (200) rather than operate end effector (200) manually.

FIG. 6 shows a schematic block diagram of an exemplary system (2001) that is configured and operable in accordance with at least some of the teachings of U.S. Pat. No. 6,866,671, entitled "Surgical Robotic Tools, Data Architecture, and Use," issued on Mar. 15, 2005, which is incorporated by reference herein; and/or U.S. Pat. No. 6,783,524, entitled "Robotic Surgical Tool with Ultrasound Cauterizing and Cutting Instrument," issued on Aug. 31, 2004, which is incorporated by reference herein. System (2001) of this example comprises a remote user interface (2000), a control system (2010), a carriage (2020) for holding a tool assembly (2030), and an end effector (2040) coupled with tool assembly (2030). Remote user interface (2000) is in communication with control system (2010) via a network (e.g., a private network). Thus, a surgeon may provide commands to control system (2010) via remote user interface (2000); and control system (2010) may provide images and other information to the user via remote user interface (2000). It will be appreciated that remote user interface (2000) may be located many miles away from control system (2010) while remaining in communication with control system (2010). Alternatively, remote user interface (2000) may be located in the same room as control system (2010). A user may use controls and a stereoscopic display (not shown) associated with remote user interface (2000) to convey instructions to control system (2010), which are ultimately communicated to end effector (2040) for interacting with human tissue as described in greater detail below. In some versions, several user interfaces (2000) may be provided, enabling more than one surgeon and/or other persons to interact with control system (2010). In such versions, two or more user interfaces (2000) may be substantially co-located or geographically dispersed.

Carriage (2020) is in communication with control system (2010) such that control system (2010) is operable to control carriage (2020) and receive data from carriage (2020), etc. Carriage (2020) comprises a plurality of motors and a variety of mechanical and electrical interfaces for receiving tool assembly (2030). For example, a lip or keyed chassis for tool assembly (2030) may be used to snap tool assembly (2030) into carriage (2020). Tool assembly (2030) is removably coupled to carriage (2020) such that carriage (2020) may drive tool assembly (2030) in response to commands received from control system (2010). In some versions, tool assembly (2030) comprises four spaced apart drive shafts that are driven by motors in carriage (2020) and are operable to couple with other components. Thus, once carriage (2020) and tool assembly (2030) mate, then motors within carriage (2020) communicate rotational motion to such drive shafts, which serve as rotating accessory interfaces. Furthermore, since carriage (2020) is in electrical communication with tool assembly (2030), electrical signals, commands, etc. may be sent to tool assembly (2030) and ultimately to end effector (2040) through carriage (2030). Thus, instructions given from a user through remote user interface (2000) ultimately cause actions at end effector (2040), which may be many miles away. Similarly, in versions where end effector (2040) is operable to provide electrical feedback, such feedback may be ultimately communicated back to remote user interface (2000).

End effector (2040) is removably coupled to tool assembly (2030), such that tool assembly (2030) is operable to drive end effector (2040). In some versions, tool assembly (2030) is operable to accept various kinds of end effectors (2040) that are operable to perform various kinds of surgical tasks. For instance, as will be described in greater detail below, variations of system (2001) may be operable to drive the kind of end effector (200) described above, in the manner described above, among other types of end effectors. In addition to or as an alternative to tool assembly (2030) being operable to accept various kinds of end effectors (2040), each end effector (2040) may have its own kind of dedicated integral tool assembly (2030), with carriage (2020) being operable to couple with and accommodate various kinds of tool assemblies (2030) to drive the various kinds of end effectors (2040). In some such versions, end effector (2040) is integral with its dedicated tool assembly (2030) and is thus unable to readily decouple from tool assembly (2030). Other suitable configurations and relationships will be apparent to those of ordinary skill in the art in view of the teachings herein. It should also be understood that several carriages (2020), tool assemblies (2030), and end effectors (2040) may be coupled with control system (2010) at the same time. System (2001) may thus provide significant modularity and flexibility for remote control of end effectors (2040) via remote user interface (2000).

Figure 7:
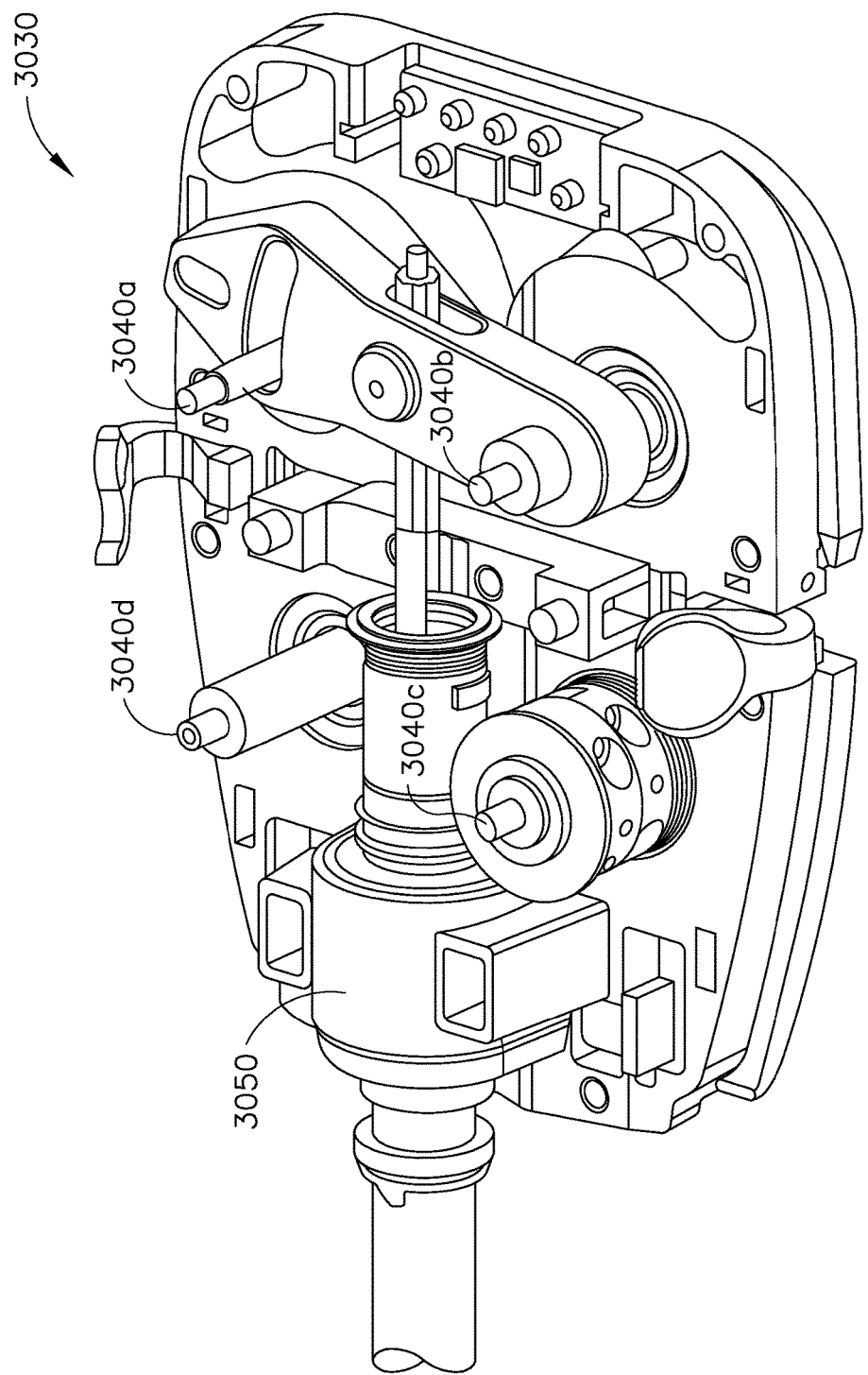
FIG. 7 depicts a perspective view of an exemplary tool assembly associated with the surgical instrument control system of FIG. 6.

FIG. 7 shows an exemplary tool assembly (3030) in greater detail. Tool assembly (3030) of this example comprises four spindles (3040a, 3040b, 3040c, 3040d). Spindles (3040a, 3040b, 3040c, 3040d) are operable to mate with connections seated within carriage (2020) (shown in FIG. 6). Thus, separate motors in carriage (2020) are operable to independently drive spindles (3040a, 3040b, 3040c, 3040d). Furthermore, electrical connections also couple to spindles (3040a, 3040b, 3040c, 3040d) and/or other features of tool assembly (3030) such that tool assembly (3030) could in some cases could provide electrical instructions to end effector (2040). In the illustrated version, end effector (2040) is attached at port (3050) of tool assembly (3030).

A. Exemplary Drive Assembly Base

Figure 8:
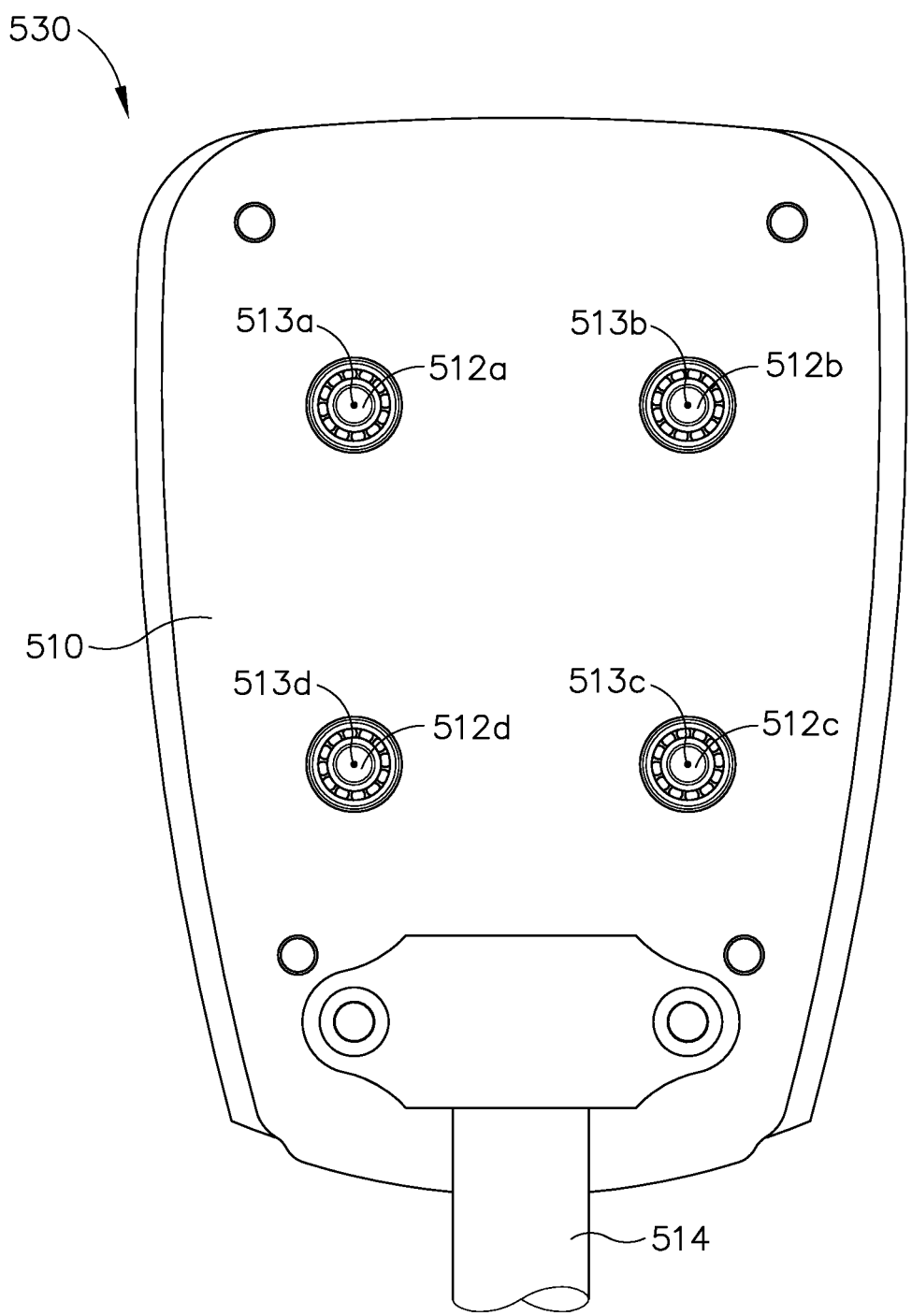
FIG. 8 depicts a top plan view of an exemplary base for the surgical instrument control system of FIG. 6.

FIG. 8 shows an exemplary base (510) for a drive assembly (530) having four drive shafts (512a, 512b, 512c, 512d). It will be appreciated that drive assembly (530) may be operable for use with tool assembly (3030) shown in FIG. 7; or may be viewed as forming at least part of a tool assembly (2030) as shown in FIG. 6. In one exemplary version, drive assembly (530) may be placed onto tool assembly (3030) such that spindles (3040a, 3040b, 3040c, 3040d) are operable to rotationally couple with drive shafts (512a, 512b, 512c, 512d), such that drive shafts (512a, 512b, 512c, 512d) provide connecting interfaces with tool assembly (3030). To facilitate the rotational communication, drive shafts (512a, 512b, 512c, 512d) are substantially aligned with spindles (3040a, 3040b, 3040c, 3040d), but other suitable configurations may be used as would be apparent to one of ordinary skill in the art. For instance, in versions where drive assembly (530) serves as a functional equivalent of a tool assembly (2030), drive shafts (512a, 512b, 512c, 512d) may each be directly rotated by respective motors in carriage (2020). While the following examples contemplate drive assembly (530) being incorporated into system (2001) described above, it should be understood that drive assembly (530) may be incorporated into various other kinds of drive systems. In the present example, as spindles (3040a, 3040b, 3040c, 3040d) turn, drive shafts (512a, 512b, 512c, 512d) also turn about rotational axes (513a, 513b, 513c, 513d). As will be described in greater detail below, rotation of drive shafts (512a, 512b, 512c, 512d) is operable to control actions at end effector (200).

In the present example, each drive shaft (512a, 512b, 512c, 512d) is operable to independently rotate either clockwise or counter clockwise or in both directions about axes (513a, 513b, 513c, 513d). In some instances, less than all four drive shafts (512a, 512b, 512c, 512d) are used or driven. Drive shafts (512a, 512b, 512c, 512d) are coupled with driven components that are added to base (510), with those driven components being configured to further drive components contained in shaft (514) as will be described in greater detail below. These driven components in shaft (514) ultimately drive end effector (200). For example, the operation of grasping arms (210, 250) depends at least in part on the control and manipulation of grasping arms (210, 250) through shaft (514). As a result, drive assembly (530) may be used to communicate rotational energy from drive shafts (512a, 512b, 512c, 512d) into motion operable to control the movement of grasping arms (210, 250). To that end, the variations of drive assembly (530) described below may be used to control components to enact various movements in grasping arms (210, 250). It will also be appreciated that in addition to grasping arms (210, 250) as shown in FIGS. 1-5H, the variations of drive assembly (530) described below may be used to interact with other devices, components, etc., as would be apparent to one of ordinary skill in the art in view of the teachings herein. Furthermore, it will be appreciated that the variations of drive assembly (530) described below need not necessarily be constructed to work necessarily with just one type of end effector. It is contemplated that the variations of drive assembly (530) described below may be used to operate various kinds of end effectors and devices as will be apparent to one of ordinary skill in the art in view of the teachings herein.

B. Exemplary Drive Assembly with Helical Gears

Figure 9:
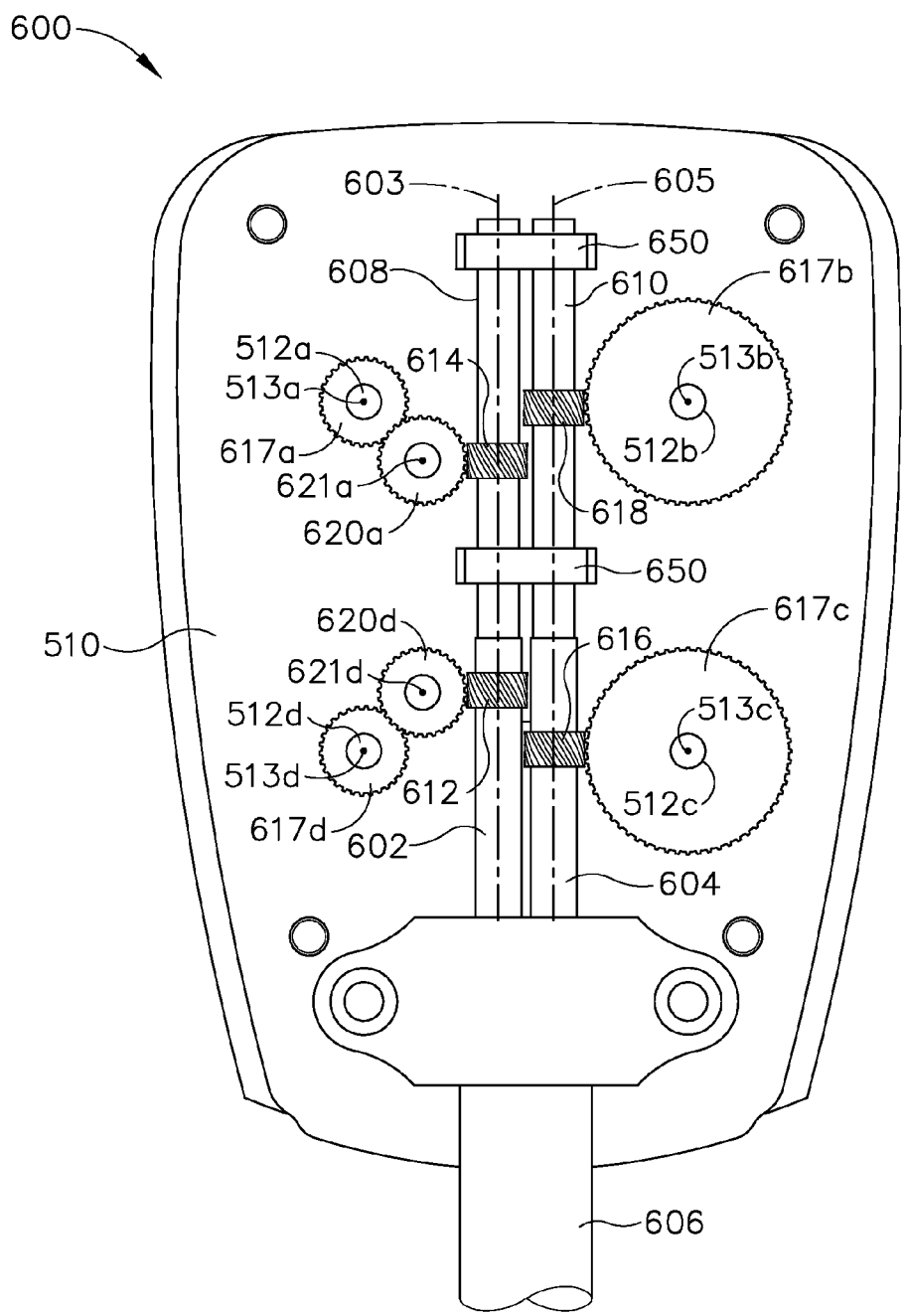
FIG. 9 depicts a top plan view of an exemplary drive assembly incorporating the base of FIG. 8.
Figure 10:
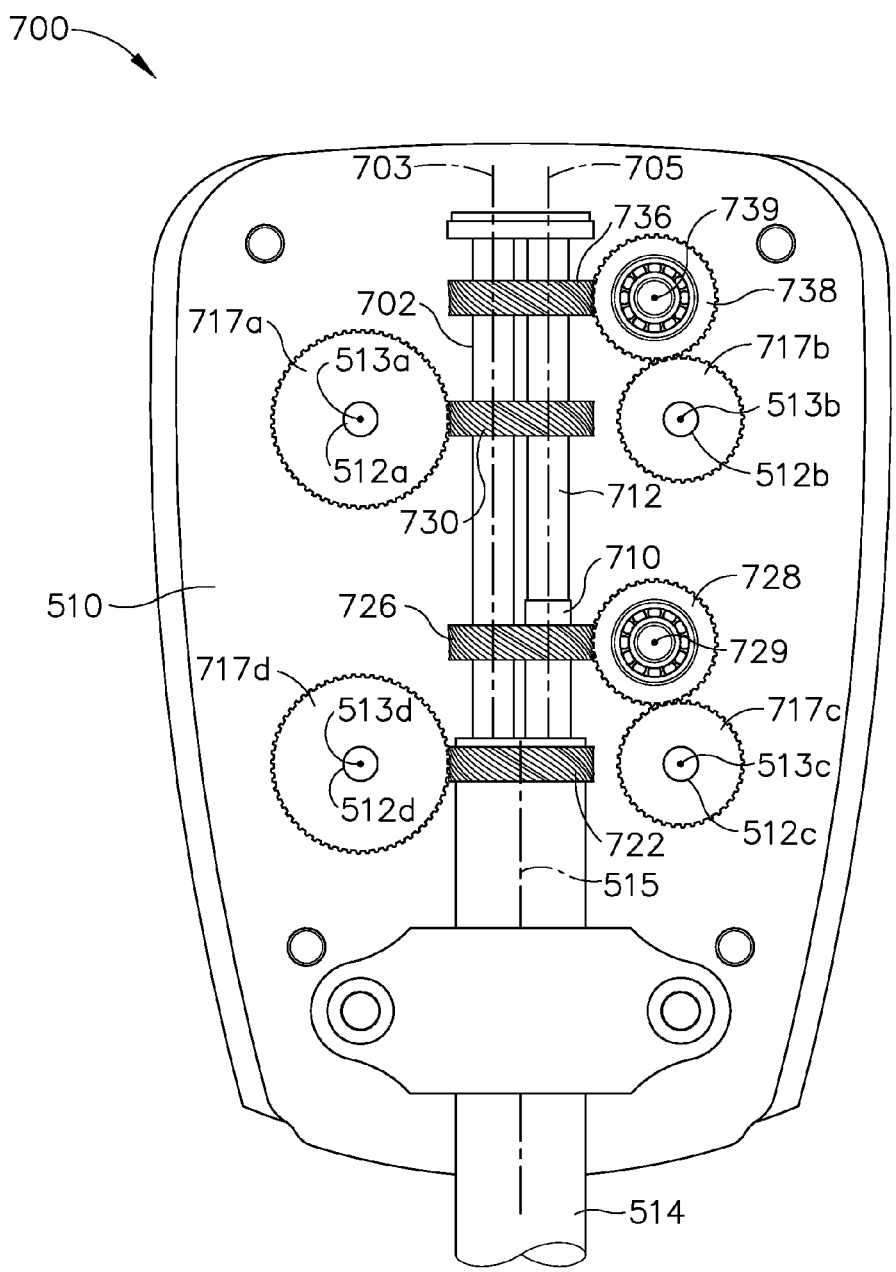
FIG. 10 depicts a top plan view of an exemplary alternative version of a drive assembly incorporating the base of FIG. 8.

FIG. 9 shows one version of a drive assembly (600) in communication with drive shafts (512a, 512b, 512c, 512d). Drive assembly (600) of this example comprises a left shaft (602), a left inner shaft (608), a right shaft (604), and a right inner shaft (610). Left inner shaft (608) extends concentrically through left shaft (602) along axis (603); and right inner shaft (610) extends concentrically through right shaft (604). Shafts (604, 610) are concentrically aligned with an axis (605), which is further aligned with axis (140) described above. Shafts (602, 604, 608, 610) extend through an outer large shaft (606), which essentially serves as an equivalent to shaft (100) described above. Shafts (608, 610) are rotatably supported in part by blocks (650), which are integral with base (510) and which permit shafts (608, 610) to rotate freely relative to base (510) (e.g., by incorporating bushings, etc.).

Left shaft (602) is unitarily secured to sheath (240) and is rotatably secured by drive shaft (512d) as will be described in greater detail below, such that sheath (240) is also rotatably secured relative to base (510) in the present example. Right shaft (604) is unitarily secured to sheath (280), such that sheath (280) rotates unitarily with right shaft (604). Left inner shaft (608) is unitarily secured to drive shaft (284), such that drive shaft (284) rotates unitarily with left inner shaft (608). Right inner shaft (610) is unitarily secured to drive shaft (244), such that drive shaft (244) rotates unitarily with right inner shaft (610). In the present example, right shaft (604), left inner shaft (608), and right inner shaft (610) are operable to rotate independently in relation to each other to drive end effector (200). An exemplary sequence of operation for rotatably driving sheath (280) and drive shafts (244, 284) via shafts (604, 608, 610) will be described in further detail below.

In the present example, a first helical gear (612) is unitarily secured to left shaft (602). First helical gear (612) meshes with a helical gear (620d), which is centered on axis (621d). Axis (621d) is parallel to axis (513d) and perpendicular to axis (603). Helical gear (620d) also meshes with a helical gear (617d) that is unitarily secured to drive shaft (512d). In the present example, the rotational position of drive shaft (512d) is fixed. It should therefore be understood that the rotational position of sheath (240) about axis (603) is fixed due to engagement between gears (612, 617d, 620d) and drive shaft (512d). In some other versions, drive shaft (512d) is rotatable about axis (513d), such that sheath (240) may be rotated by drive shaft (512b).

A second helical gear (614) is unitarily secured to left inner shaft (608). Second helical gear (614) meshes with a helical gear (620a), which is rotatable about axis (621a). Axis (621a) is parallel to axis (513a) and perpendicular to axis (603). Helical gear (620a) also meshes with a helical gear (617a) that is unitarily secured to drive shaft (512a). Thus, rotation of drive shaft (512a) causes rotation of helical gear (620a) about axis (621a), which in turn causes rotation of helical gear (614) and left inner shaft (608) about axis (603). It should therefore be understood that drive shaft (512a) may be driven to selectively rotate drive shaft (244) via gears (614, 617a, 620a) and left inner shaft (608).

A third helical gear (616) is unitarily secured to right shaft (604). Third helical gear (616) meshes with a helical gear (617c) that is unitarily secured to drive shaft (512c). Thus, rotation of drive shaft (512c) causes rotation of helical gear (617c) about axis (513c), which in turn causes rotation of helical gear (616) and right shaft (604) about axis (605). It should therefore be understood that drive shaft (512c) may be driven to selectively rotate sheath (280) via gears (616, 617c) and right shaft (604).

A fourth helical gear (618) is unitarily secured to right inner shaft (610). Fourth helical gear (618) meshes with a helical gear (617b), which is unitarily secured to drive shaft (512b). Thus, rotation of drive shaft (512b) causes rotation of helical gear (617b) about axis (513b), which in turn causes rotation of right shaft (604) about axis (605). It should therefore be understood that drive shaft (512b) may be driven to selectively rotate drive shaft (284) via gears (616, 617c) and right shaft (604).

An exemplary sequence of use will be described as it relates to FIGS. 5A-5H. Regarding FIGS. 5A-5B, the entire drive assembly (600) is rotated about an axis running along the center of shaft (606) in order to rotate end effector (200) as shown in FIGS. 5A-5B. During this transition, the rotational positions of drive shafts (512a, 512d) relative to each other are substantially fixed, ensuring a continuous grip on needle (50) by first grasping arm (210). During the transition shown in FIG. 5B-5C, drive shafts (512b, 512c) are simultaneously driven to rotate shafts (604, 610) together to rotate grasping arm (250) about axis (140). The rotational positions of drive shafts (512a, 512d) remain fixed relative to each other during this transition. After reaching the configuration shown in FIG. 5C, drive shaft (512b) is driven to rotate shaft (610) while drive shaft (512c) holds shaft (604) stationary, causing jaws (260, 270) of grasping arm (250) to grasp needle (50). Drive shaft (512a) is then driven to rotate shaft (608), causing jaws (220, 230) of grasping arm (210) to release needle (50).

To then transition to the configuration shown in FIG. 5D, drive shafts (512b, 512c) are simultaneously driven to rotate shafts (604, 610) together to rotate grasping arm (250) about axis (140) while maintaining a grip on needle (50). Once end effector (200) has been repositioned as shown in FIG. 5E, drive shafts (512b, 512c) are again simultaneously driven to rotate shafts (604, 610) together to rotate grasping arm (250) about axis (140) to the position shown in FIG. 5F, while maintaining a grip on needle (50). At this stage, drive shaft (512a) is driven to rotate shaft (608), causing jaws (220, 230) of grasping arm (210) to grasp needle (50). Drive shaft (512b) is then driven to rotate shaft (610) while drive shaft (512c) holds the rotational position of shaft (604), causing jaws (260, 270) of grasping arm (250) to release needle (50). Drive shafts (512b, 512c) are then simultaneously driven to rotate shafts (604, 610) together to rotate grasping arm (250) about axis (140) to the position shown in FIG. 5G. The entire drive assembly (600) may then be moved to rotate end effector (200) to the position shown in FIG. 5H; then again moved to locate end effector (200) at a position similar the position shown in FIG. 5A to make another stitch in tissue (300, 302). The above process may be repeated until the desired number of stitches are placed in tissue (300, 302). Other suitable ways in which drive assembly (600) may be operated will be apparent to those of ordinary skill in the art in view of the teachings herein.

C. Exemplary Drive Assembly with Ring Gears

FIGS. 10-13 show another exemplary version of a drive assembly (700) in communication with drive shafts (512a, 512b, 512c, 512d). Drive assembly (700) of this example comprises a left shaft (704), left inner shaft (702), right shaft (710), right inner shaft (712), and outer shaft (514). Left inner shaft (702) extends concentrically through left shaft (704) along axis (703); and right inner shaft (712) extends concentrically through right shaft (710). Shafts (710, 712) are concentrically aligned with an axis (705), which is further aligned with axis (140) described above. Shafts (702, 704, 710, 712) extend through outer shaft (514), which essentially serves as an equivalent to shaft (100) described above. A plurality of bushings (not shown) are spaced along the length of the interior of shaft (514). These bushings are configured to provide support and/or guidance for shafts (704, 710) along the length of shaft (514). Shaft (704) is fixedly secured to one or more of these bushings, such that shaft (704) is incapable of rotating relative to shaft (504) in the present example. In some other versions, shaft (704) is rotatable relative to shaft (504). Shaft (710) is able to freely rotate relative to shaft (514). Nevertheless, the bushings are configured to provide orbital motion of all shafts (702, 704, 710, 712) about axis (515) when shaft (514) is rotated about axis (515) as will be described in greater detail below. Axis (515) is aligned with axis (130) in this example.

Left shaft (704) is unitarily secured to sheath (240). Left inner shaft (702) is unitarily secured to drive shaft (244). Right shaft (710) is unitarily secured to sheath (280). Right inner shaft (712) is unitarily secured to drive shaft (284). In the present example, right shaft (710), left inner shaft (702), and right inner shaft (712) are operable to rotate independently in relation to each other to drive end effector (200). Outer shaft (514) is also operable to rotate about axis (515), which is aligned with axis (130) described above. An exemplary sequence of operation for rotatably driving sheath (280) and drive shafts (244, 284) via shafts (702, 710, 712) will be described in further detail below.

Figure 11:
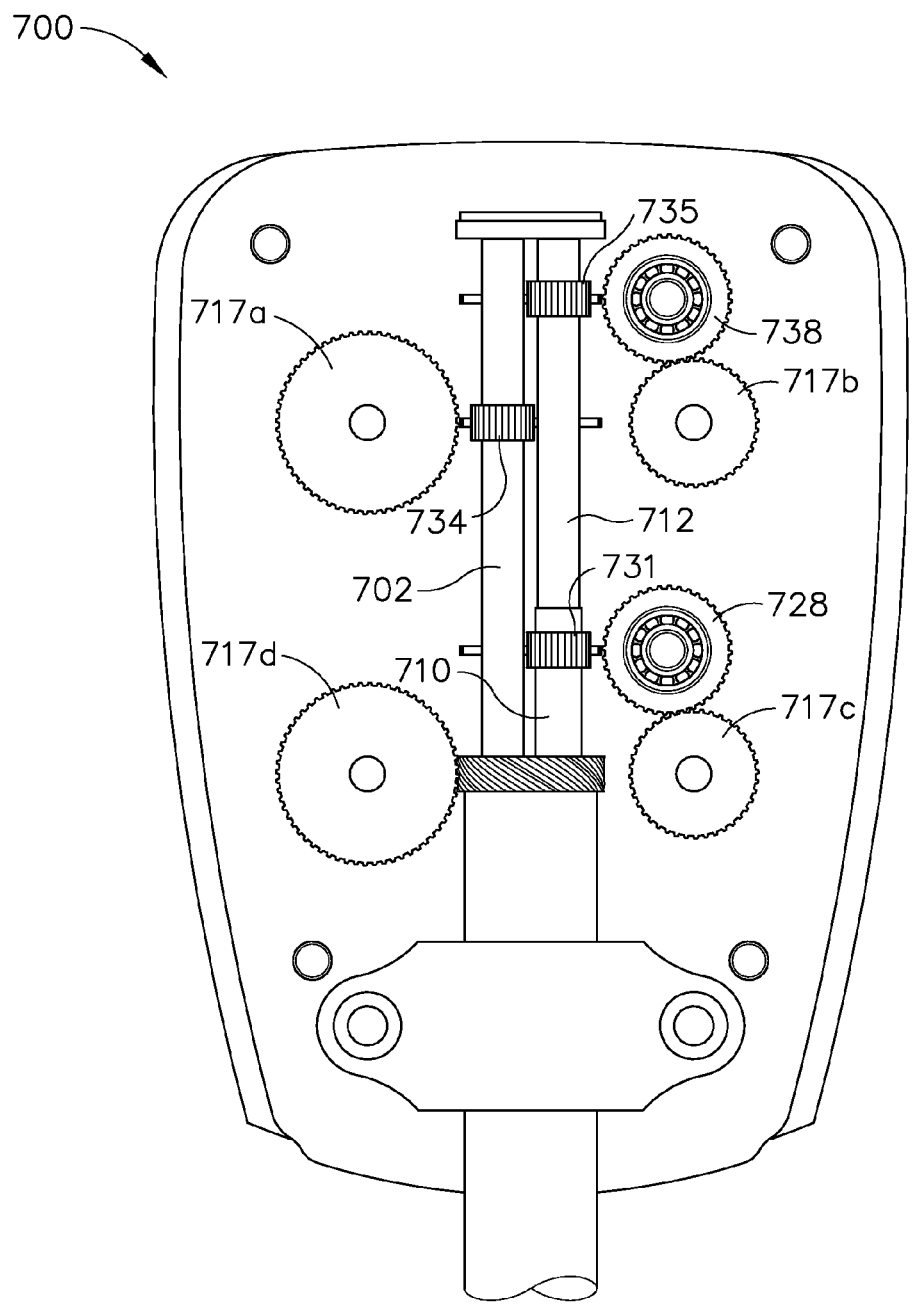
FIG. 11 depicts a top plan view of the drive assembly of FIG. 10, with ring gears omitted to reveal helical gears.
Figure 12:
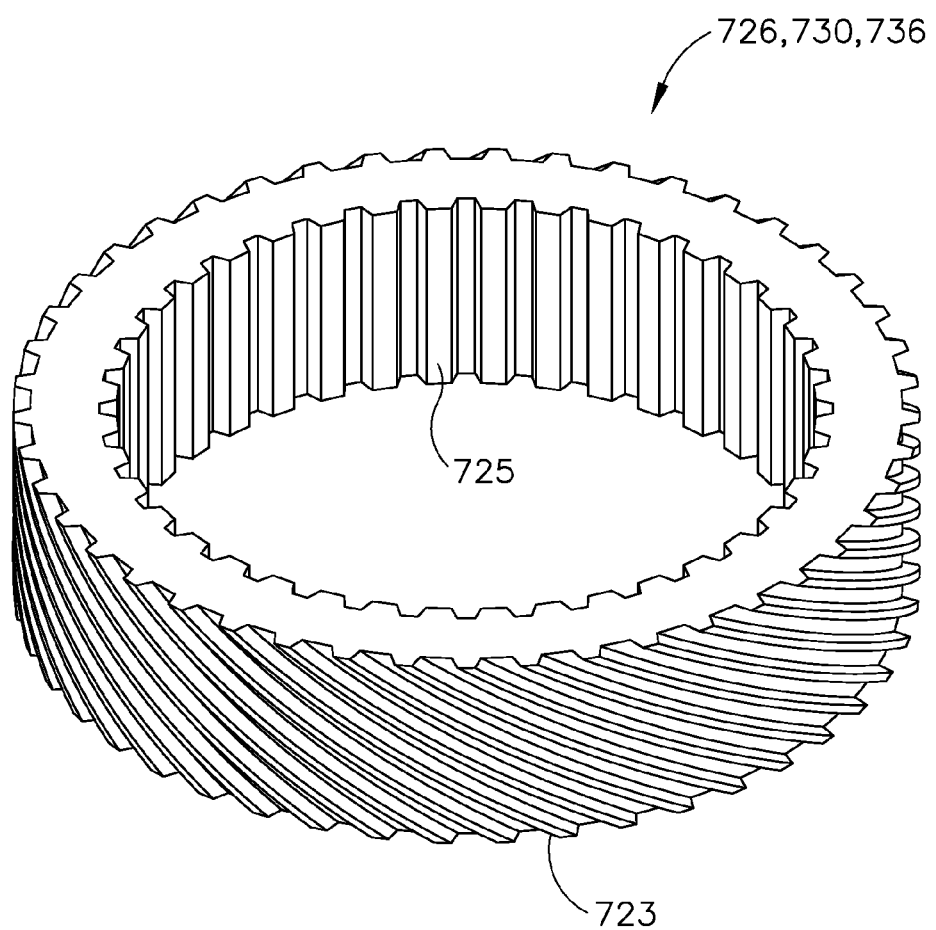
FIG. 12 depicts a perspective view of a ring gear of the drive assembly of FIG. 10.
Figure 13:
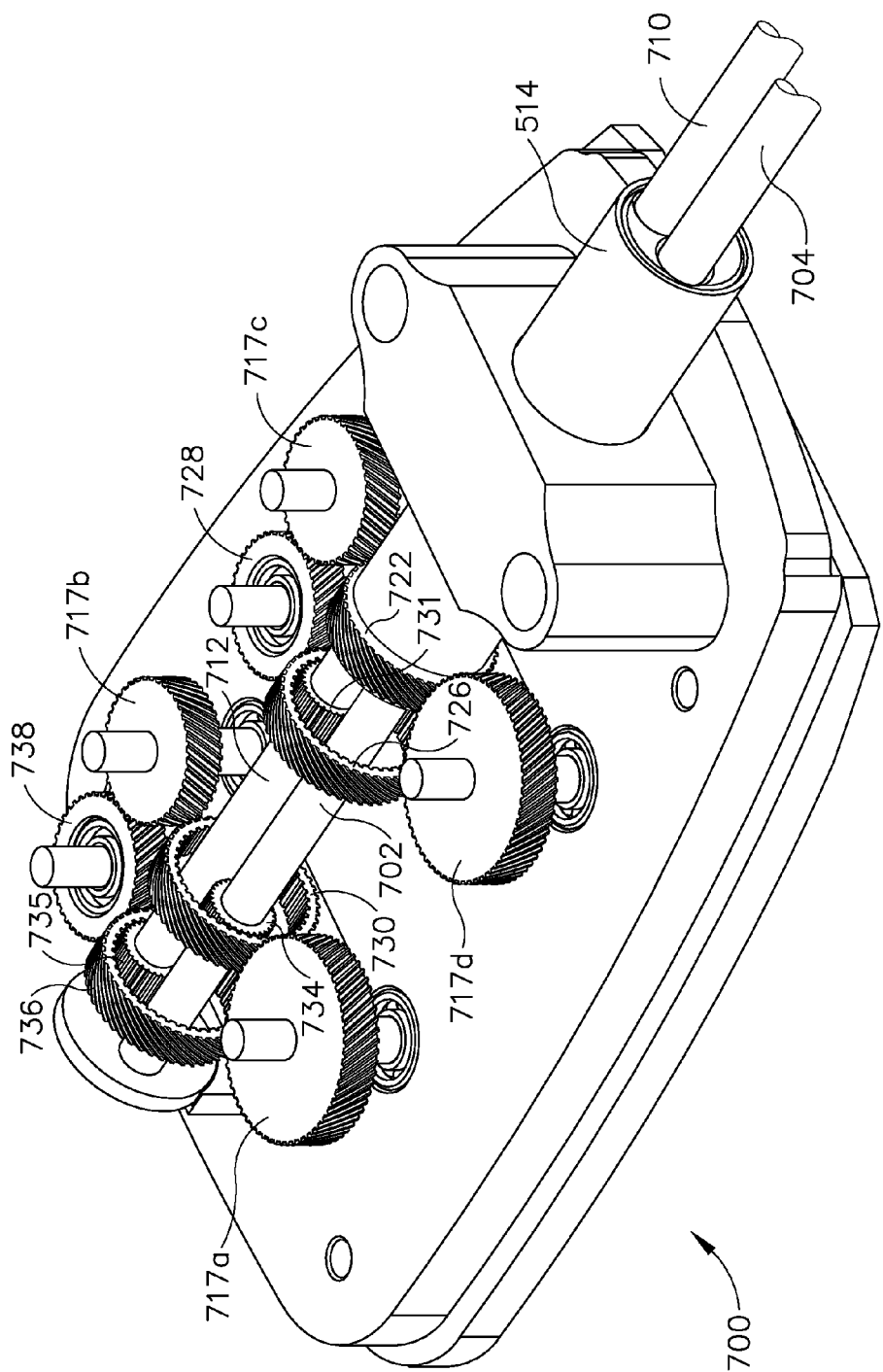
FIG. 13 depicts a perspective view of the drive assembly of FIG. 10.

In the present example, as best seen in FIG. 11, a gear (731) is unitarily secured to shaft (710). Gear (731) includes a plurality of longitudinally extending teeth angularly arrayed about its exterior. As best seen in FIGS. 12-13, a ring gear (726) is positioned about gear (731) and includes internal teeth (725) that mesh with the teeth of gear (731). Ring gear (726) is sized to further encompass shaft (702), though ring gear (726) does not contact or otherwise engage shaft (702). Ring gear (726) includes exterior helical teeth (723), which mesh with complementary helical teeth of helical gear (728). Helical gear (728) rotates about axis (729) and also meshes with a helical gear (717c) that is unitarily secured to drive shaft (512c). Thus, as drive shaft (512c) is driven to rotate about axis (513c), helical gear (728) is driven to rotate about axis (729), which in turn drives shaft (710) to rotate about axis (705) through engagement with ring gear (726) and gear (731). It should therefore be understood that drive shaft (512c) may be driven to selectively rotate sheath (280) via gears (717c, 726, 728, 731) and right shaft (710).

Referring back to FIG. 11, a gear (734) is unitarily secured to shaft (702). Gear (734) includes a plurality of longitudinally extending teeth angularly arrayed about its exterior. As best seen in FIG. 13, a ring gear (730) is positioned about gear (734) and includes internal teeth (725) that mesh with the teeth of gear (734). Ring gear (730) is sized to further encompass shaft (712), though ring gear (730) does not contact or otherwise engage shaft (712). Ring gear (730) includes exterior helical teeth (723), which mesh with complementary helical teeth of helical gear (717a), which is unitarily secured to drive shaft (512a). Thus, as drive shaft (512a) is driven to rotate about axis (513a), helical gear (717a) drives shaft (702) to rotate about axis (703) through engagement with ring gear (730) and gear (734). It should therefore be understood that drive shaft (512a) may be driven to selectively rotate drive shaft (244) via gears (717a, 730, 734) and left inner shaft (702).

Again referring to FIG. 11, a gear (735) is unitarily secured to shaft (712). Gear (735) includes a plurality of longitudinally extending teeth angularly arrayed about its exterior. As best seen in FIG. 13, a ring gear (736) is positioned about gear (735) and includes internal teeth (725) that mesh with the teeth of gear (735). Ring gear (736) includes exterior helical teeth (723), which mesh with complementary helical teeth of helical gear (738). Helical gear (738) rotates about axis (739) and also meshes with a helical gear (717b) that is unitarily secured to drive shaft (512b). Thus, as drive shaft (512b) is driven to rotate about axis (513b), helical gear (738) is driven to rotate about axis (739), which in turn drives shaft (712) to rotate about axis (705) through engagement with ring gear (736) and gear (735). It should therefore be understood that drive shaft (512b) may be driven to selectively rotate drive shaft (284) via gears (717b, 738, 736, 735) and right inner shaft (712).

An outer helical gear (722) is unitarily secured to outer shaft (514). The exterior helical teeth of gear (722) mesh with complementary helical teeth of helical gear (717d), which is unitarily secured to drive shaft (512d). Thus, as drive shaft (512d) is driven to rotate about axis (513d), helical gear (717d) is driven to rotate about axis (513d), which in turn drives shaft (514) to rotate about axis (515) through engagement with gear (722). As noted above, bushings within shaft (514) cause shafts (702, 704, 710, 712) to orbit about axis (515) when shaft (514) is rotated about axis (515).

An exemplary sequence of use will be described as it relates to FIGS. 5A-5H. Regarding FIGS. 5A-5B, drive shaft (512d) is driven to rotate shaft (514) in order to rotate end effector (200) about axis (130) as shown in FIGS. 5A-5B. Since this rotation will also result in orbit of shafts (702, 704, 710, 712) about axis (515, 130), it should be understood that drive shaft (512a) should also be activated during this stage to rotate ring gear (730) about axis (515) in synchronization with rotation of shaft (514) about axis (515). This will ensure that shaft (702) does not rotate relative to shaft (704), which will further ensure that grasping arm (210) maintains its firm grip on needle (50) during the transition from the position shown in FIG. 5A to the position shown in FIG. 5B. Drive shafts (512b, 512c) may also be activated at this stage or may remain idle, though it should be understood that the state of drive shafts (512b, 512c) may affect the state of jaws (260, 270) of grasping arm (250) during the transition from the position shown in FIG. 5A to the position shown in FIG. 5B.

During the transition shown in FIG. 5B-5C, drive shafts (512b, 512c) are simultaneously driven to rotate shafts (710, 712) together to rotate grasping arm (250) about axis (140). The rotational positions of drive shafts (512a, 512d) remain fixed relative to each other during this transition. After reaching the configuration shown in FIG. 5C, drive shaft (512b) is driven to rotate shaft (712) while drive shaft (512c) holds shaft (710) stationary, causing jaws (260, 270) of grasping arm (250) to grasp needle (50). Drive shaft (512a) is then driven to rotate shaft (702), causing jaws (220, 230) of grasping arm (210) to release needle (50). To then transition to the configuration shown in FIG. 5D, drive shafts (512b, 512c) are simultaneously driven to rotate shafts (710, 712) together to rotate grasping arm (250) about axis (140) while maintaining a grip on needle (50).

Once end effector (200) has been repositioned as shown in FIG. 5E, drive shafts (512b, 512c) are again simultaneously driven to rotate shafts (710, 712) together to rotate grasping arm (250) about axis (140) to the position shown in FIG. 5F, while maintaining a grip on needle (50). At this stage, drive shaft (512a) is driven to rotate shaft (702), causing jaws (220, 230) of grasping arm (210) to grasp needle (50). Drive shaft (512b) is then driven to rotate shaft (712) while drive shaft (512c) holds the rotational position of shaft (710), causing jaws (260, 270) of grasping arm (250) to release needle (50). Drive shafts (512b, 512c) are then simultaneously driven to rotate shafts (710, 712) together to rotate grasping arm (250) about axis (140) to the position shown in FIG. 5G.

After reaching the position shown in FIG. 5G, drive shaft (512d) is driven to rotate shaft (514) in order to rotate end effector (200) about axis (130) as shown in FIG. 5H. Since this rotation will also result in orbit of shafts (702, 704, 710, 712) about axis (515, 130), it should be understood that drive shaft (512a) should also be activated during this stage to rotate ring gear (730) about axis (515) in synchronization with rotation of shaft (514) about axis (515). This will ensure that shaft (702) does not rotate relative to shaft (704), which will further ensure that grasping arm (210) maintains its firm grip on needle (50) during the transition from the position shown in FIG. 5G to the position shown in FIG. 5H. Drive shafts (512b, 512c) may also be activated at this stage or may remain idle, though it should be understood that the state of drive shafts (512b, 512c) may affect the state of jaws (260, 270) of grasping arm (250) during the transition from the position shown in FIG. 5G to the position shown in FIG. 5H. The entire drive assembly (700) may then be moved to locate end effector (200) at a position similar the position shown in FIG. 5A to make another stitch in tissue (300, 302). The above process may be repeated until the desired number of stitches are placed in tissue (300, 302). Other suitable ways in which drive assembly (700) may be operated will be apparent to those of ordinary skill in the art in view of the teachings herein.

D. Exemplary Drive Assembly with Rack-Driven Clutch

Figure 14A:
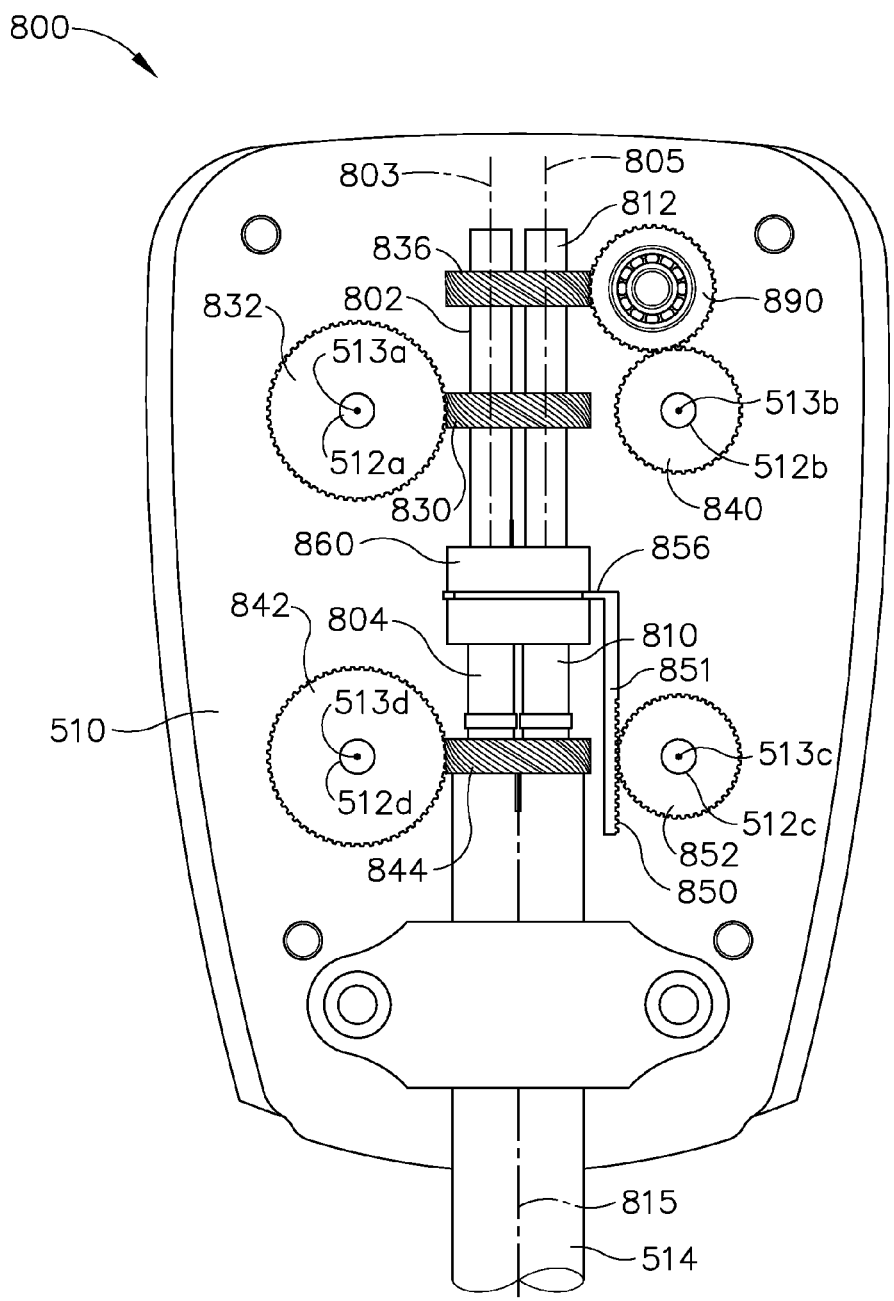
FIG. 14A depicts a top plan view of an exemplary alternative version of a drive assembly incorporating the base of FIG. 8 with a clutch mechanism.

FIG. 14A shows another exemplary version of a drive assembly (800) in communication with drive shafts (512a, 512b, 512c, 512d). Drive assembly (800) of this example comprises a left shaft (804), left inner shaft (802), right shaft (810), right inner shaft (812), and outer shaft (514). Left inner shaft (802) extends concentrically through left shaft (804) along axis (803); and right inner shaft (812) extends concentrically through right shaft (810). Shafts (810, 812) are concentrically aligned with an axis (805), which is further aligned with axis (140) described above. Shafts (802, 804, 810, 812) extend through outer shaft (514), which essentially serves as an equivalent to shaft (100) described above. A plurality of bushings (not shown) are spaced along the length of the interior of shaft (514). These bushings are configured to provide support and/or guidance for shafts (804, 810) along the length of shaft (514). Shaft (804) is fixedly secured to one or more of these bushings, such that shaft (804) is incapable of rotating relative to shaft (504) in the present example. In some other versions, shaft (804) is rotatable relative to shaft (504). Shaft (810) is able to freely rotate relative to shaft (514). Nevertheless, the bushings are configured to provide orbital motion of all shafts (802, 804, 810, 812) about axis (515) when shaft (514) is rotated about axis (515) as will be described in greater detail below. Axis (515) is aligned with axis (130) in this example.

Left shaft (804) is unitarily secured to sheath (240). Left inner shaft (802) is unitarily secured to drive shaft (244). Right shaft (810) is unitarily secured to sheath (280). Right inner shaft (812) is unitarily secured to drive shaft (284). In the present example, left inner shaft (802) and right inner shaft (812) are operable to rotate independently in relation to each other to drive end effector (200). Right shaft (810) rotates with right inner shaft (812) when a clutch mechanism is engaged as will be described in greater detail below. Outer shaft (514) is also operable to rotate about axis (515), which is aligned with axis (130) described above. An exemplary sequence of operation for rotatably driving sheath (280) and drive shafts (244, 284) via shafts (802, 810, 812) will be described in further detail below.

In the present example, a gear (not show) is unitarily secured to shaft (802). This gear is substantially identical to gear (734) described above, and includes a plurality of longitudinally extending teeth angularly arrayed about its exterior. A ring gear (830), similar to ring gear (730) described above, is positioned about this gear and includes internal teeth that mesh with the teeth of this gear. Ring gear (830) is sized to further encompass shaft (812), though ring gear (830) does not contact or otherwise engage shaft (812). Ring gear (830) includes exterior helical teeth, which mesh with threading of helical gear (832). Helical gear (832) is unitarily coupled with drive shaft (512a). Thus, as drive shaft (512a) is driven to rotate about axis (513a), helical gear (832) is driven to rotate about axis (513a), which in turn drives shaft (802) to rotate about axis (803) through engagement with ring gear (830). It should therefore be understood that drive shaft (512a) may be driven to selectively rotate drive shaft (244) via gears (830, 832) and left inner shaft (802).

A gear (not shown) is unitarily secured to shaft (812). This gear is substantially identical to gear (735) described above, and includes a plurality of longitudinally extending teeth angularly arrayed about its exterior. A ring gear (836), similar to ring gear (736) described above, is positioned about gear (838) and includes internal teeth that mesh with the teeth of this gear. Ring gear (836) is sized to further encompass shaft (802), though ring gear (836) does not contact or otherwise engage shaft (802). Ring gear (836)

includes exterior helical teeth, which mesh with threading of a helical gear (890). Helical gear (890) also meshes with another helical gear (840), which is unitarily secured to drive shaft (512*b*). Thus, as drive shaft (512*b*) is driven to rotate about axis (513*b*), helical gear (840) is driven to rotate about axis (513*b*), which in turn drives shaft (812) to rotate about axis (805) through engagement with ring gear (836). It should therefore be understood that drive shaft (512*b*) may be driven to selectively rotate drive shaft (284) via gears (836, 840, 890) and right inner shaft (812).

Drive assembly (800) of this example further comprises a rack (850) and pinion (852), which are operable to drive a clutch bushing (860). Pinion (852) is unitarily secured to drive shaft (512*c*). Thus, as drive shaft (512*c*) is driven to rotate about axis (513*c*), pinion (852) is driven to rotate about axis (513*c*), which in turn provides linear translation of rack (850). Rack (850) is an integral feature of a longitudinally extending arm (851), which is fixedly secured to a frame (856). Bushing (860) is secured to frame (856) in a manner that permits bushing (860) to rotate about axis (815) relative to frame (856), though bushing (860) translates longitudinally with frame (856) as will be described in greater detail below. It should therefore be understood that bushing (860) is translated longitudinally in response to rotation of drive shaft (512*c*). In particular, drive shaft (512*c*) is operable to cause bushing to translate between three longitudinal positions—a distal position, an intermediate position, and a proximal position. Exemplary consequences of these three positions will be described in greater detail below. Shafts (802, 812) pass through bushing (860), while the proximal ends of shafts (804, 810) are disposed in bushing (860). However, shafts (802, 804, 810, 812) do not translate when bushing (860) translates in response to activation of drive shaft (512*c*). When drive shaft (512*d*) is activated to rotate shaft (514) as will be described in greater detail below, shafts (802, 804, 810, 812) will orbit about axis (815) while bushing (862) rotates about axis (815).

Bushing (860) includes features (not shown) that selectively engage shafts (804, 810). In particular, when bushing (860) is in the proximal position, shafts (804, 810) are both rotatably secured to bushing (860). When bushing (860) is in the intermediate longitudinal position, bushing (860) is rotatably decoupled from shafts (804, 810), such that shafts (804, 810) may rotate freely relative to bushing (860). When bushing (860) is in the distal position, shafts (804, 810) are once again both rotatably secured to bushing (860). It should therefore be understood that shafts (804, 810) are coupled with bushing (860) when bushing (860) is in the proximal and distal positions; but not when bushing (860) is in the intermediate position. Various kinds of structures and features that may be used to provide the above-described selective engagement between bushing (860) and shafts (804, 810) will be apparent to those of ordinary skill in the art in view of the teachings herein.

Figure 14B:
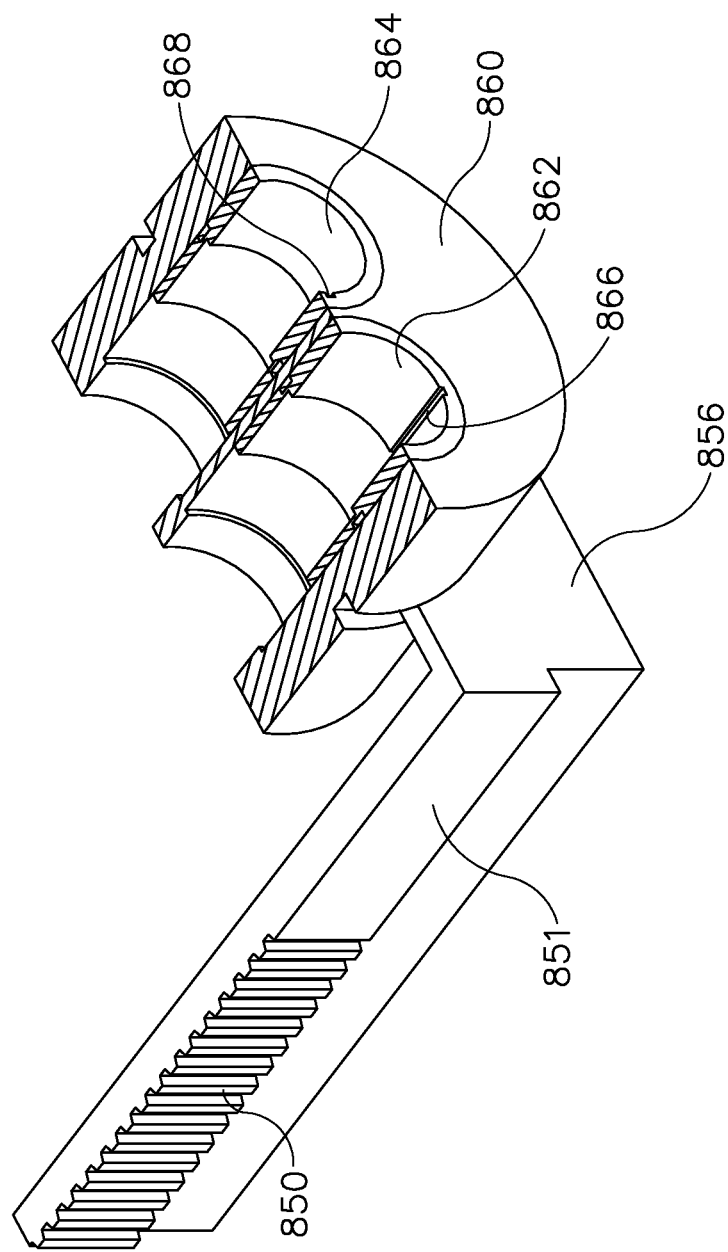
FIG. 14B depicts perspective view of the clutch of the drive assembly of FIG. 14A, with part of the clutch shown in cross-section.

As best seen in FIG. 14B, a pair of clutch cuffs (862, 864) are disposed in bushing (860). Each cuff (862, 864) is independently rotatable within bushing (860), though cuffs (862, 864) translate together with bushing (860). One cuff (862) is coaxially positioned about shaft (812). Cuff (862) defines a longitudinally extending keyway (866). Shaft (812) defines an outwardly extending key (not shown) that is disposed in keyway (866). Thus, shaft (812) and cuff (862) rotate together, while cuff (862) is configured to translate relative to shaft (812) as will be described in greater detail below. Shaft (810) also includes an outwardly extending key (not shown) that is selectively disposed in keyway (866). In particular, the key of shaft (810) is disposed in keyway (866) when bushing (860) and cuff (862) are advanced to the distal position and in the intermediate position; while the key of shaft (810) is not disposed in keyway (866) when bushing (860) and cuff (862) are retracted to the proximal position. It should therefore be understood that shaft (810) is rotationally coupled with shaft (812) via cuff (862) when bushing (860) and cuff (862) are in the distal and intermediate positions; while shaft (810) is rotationally decoupled from shaft (812) when bushing (860) and cuff (862) are in the proximal position.

The other cuff (864) is coaxially positioned about shaft (802). Cuff (864) defines a longitudinally extending keyway (868). Shaft (802) defines an outwardly extending key (not shown) that is disposed in keyway (868). Thus, shaft (802) and cuff (864) rotate together, while cuff (864) is configured to translate relative to shaft (802) as will be described in greater detail below. Shaft (804) also includes an outwardly extending key (not shown) that is selectively disposed in keyway (868). In particular, the key of shaft (804) is disposed in keyway (868) when bushing (860) and cuff (864) are advanced to the distal position and the intermediate position; while the key of shaft (804) is not disposed in keyway (868) when bushing (860) and cuff (864) are retracted to the proximal position. It should therefore be understood that shaft (804) is rotationally coupled with shaft (802) via cuff (864) when bushing (860) and cuff (864) are in the distal and intermediate positions; while shaft (804) is rotationally de-coupled from shaft (802) when bushing (860) and cuff (864) are in the proximal position.

An outer helical gear (844) is unitarily secured to outer shaft (514). The exterior helical teeth of gear (844) mesh with threading of helical gear (842), which is unitarily secured to drive shaft (512*d*). Thus, as drive shaft (512*d*) is driven to rotate about axis (513*d*), helical gear (842) is driven to rotate about axis (513*d*), which in turn drives shaft (514) to rotate about axis (515) through engagement with gear (844). As noted above, bushings within shaft (514) cause shafts (802, 804, 810, 812) to orbit about axis (515) when shaft (514) is rotated about axis (515).

An exemplary sequence of use will be described as it relates to FIGS. 5A-5H. Regarding FIGS. 5A-5B, drive shaft (512*d*) is activated to rotate shaft (514) in order to rotate end effector (200) about axis (130) as shown in FIGS. 5A-5B. Bushing (860) is at the distal position at this stage, such that shafts (802, 804) are rotatably secured together, shafts (810, 810) are rotatably secured together, shafts (804, 810) are rotatably secured to bushing (860), and bushing (860) rotates freely. Since the rotation of shaft (514) will also result in orbit of shafts (802, 804, 810, 812) about axis (815, 130), it should be understood that drive shafts (512*a*, 512*b*, 512*c*) may be de-activated or idle during this stage to enable gears (832, 840, 852, 890) to rotate freely. Since shafts (802, 804) remain rotatably secured to each other at this stage, grasping arm (210) maintains its firm grip on needle (50) during the transition from the position shown in FIG. 5A to the position shown in FIG. 5B.

After reaching the configuration shown in FIG. 5B, drive shaft (512*c*) is activated to retract bushing (860) proximally to the intermediate position. Thus, shafts (810, 812) remain coupled together while shaft (810) is de-coupled from bushing (860). During the transition shown in FIG. 5B-5C, drive shaft (512*b*) is activated to rotate shafts (810, 812) together to rotate grasping arm (250) about axis (140). The rotational positions of drive shafts (512*a*, 512*c*, 512*d*) remain fixed relative to each other during this transition.

After reaching the configuration shown in FIG. 5C, drive shaft (512*c*) is activated to drive rack (850) proximally to the proximal position, thereby disengaging cuff (866) from shaft (810) to de-couple shaft (810) from shaft (812). With cuff (866) (and therefore shaft (812)) disengaged from shaft (810), drive shaft (512b) is then activated to rotate shaft (812) while shaft (810) remains stationary, causing jaws (260, 270) of grasping arm (250) to grasp needle (50). Drive shaft (512a) is then activated to rotate shaft (802) while shaft (804) remains rotationally stationary, causing jaws (220, 230) of grasping arm (210) to release needle (50). Drive shaft (512c) is then activated to drive rack (850) distally to the intermediate position again, thereby driving cuff (866) back into engagement with shaft (810) to re-couple shaft (810) with shaft (812). To then transition to the configuration shown in FIG. 5D, drive shaft (512b) is activated to rotate shafts (810, 812) together to rotate grasping arm (250) about axis (140) while maintaining a grip on needle (50).

Once end effector (200) has been repositioned as shown in FIG. 5E, drive shaft (512b) is again activated to rotate shafts (810, 812) together to rotate grasping arm (250) about axis (140) to the position shown in FIG. 5F, while maintaining a grip on needle (50). At this stage, drive shaft (512a) is driven to rotate shaft (802), causing jaws (220, 230) of grasping arm (210) to grasp needle (50). Drive shaft (512c) is then activated to drive rack (850) proximally to the proximal position again, thereby disengaging cuff (866) from shaft (810) to de-couple shaft (810) from shaft (812). Drive shaft (512b) is then activated to rotate shaft (812) while shaft (810) remains stationary, causing jaws (260, 270) of grasping arm (250) to release needle (50). Drive shaft (512c) is then activated to drive rack (850) distally again to the intermediate position, thereby driving cuff (866) back into engagement with shaft (810) to re-couple shaft (810) with shaft (812). Drive shaft (512b) is then activated to rotate shafts (810, 812) together to rotate grasping arm (250) about axis (140) to the position shown in FIG. 5G.

After reaching the position shown in FIG. 5G, drive shaft (512c) is activated to drive rack (850) distally to the distal position, thereby coupling bushing (860) with shafts (804, 810). Drive shaft (512d) is then driven to rotate shaft (514) in order to rotate end effector (200) about axis (130) as shown in FIG. 5H. Since this rotation will also result in orbit of shafts (802, 804, 810, 812) about axis (815, 130), it should be understood that drive shafts (512a, 512b, 512c) may be de-activated or idle during this stage to enable gears (832, 840, 852, 890) to rotate freely. Since shafts (802, 804) remain rotatably secured to each other at this stage, grasping arm (210) maintains its firm grip on needle (50) during the transition from the position shown in FIG. 5G to the position shown in FIG. 5H. The entire drive assembly (800) may then be moved to locate end effector (200) at a position similar the position shown in FIG. 5A to make another stitch in tissue (300, 302). The above process may be repeated until the desired number of stitches are placed in tissue (300, 302). Other suitable ways in which drive assembly (800) may be operated will be apparent to those of ordinary skill in the art in view of the teachings herein.

E. Exemplary Drive Assembly for Linearly Driven Suturing Device

Figure 15A:
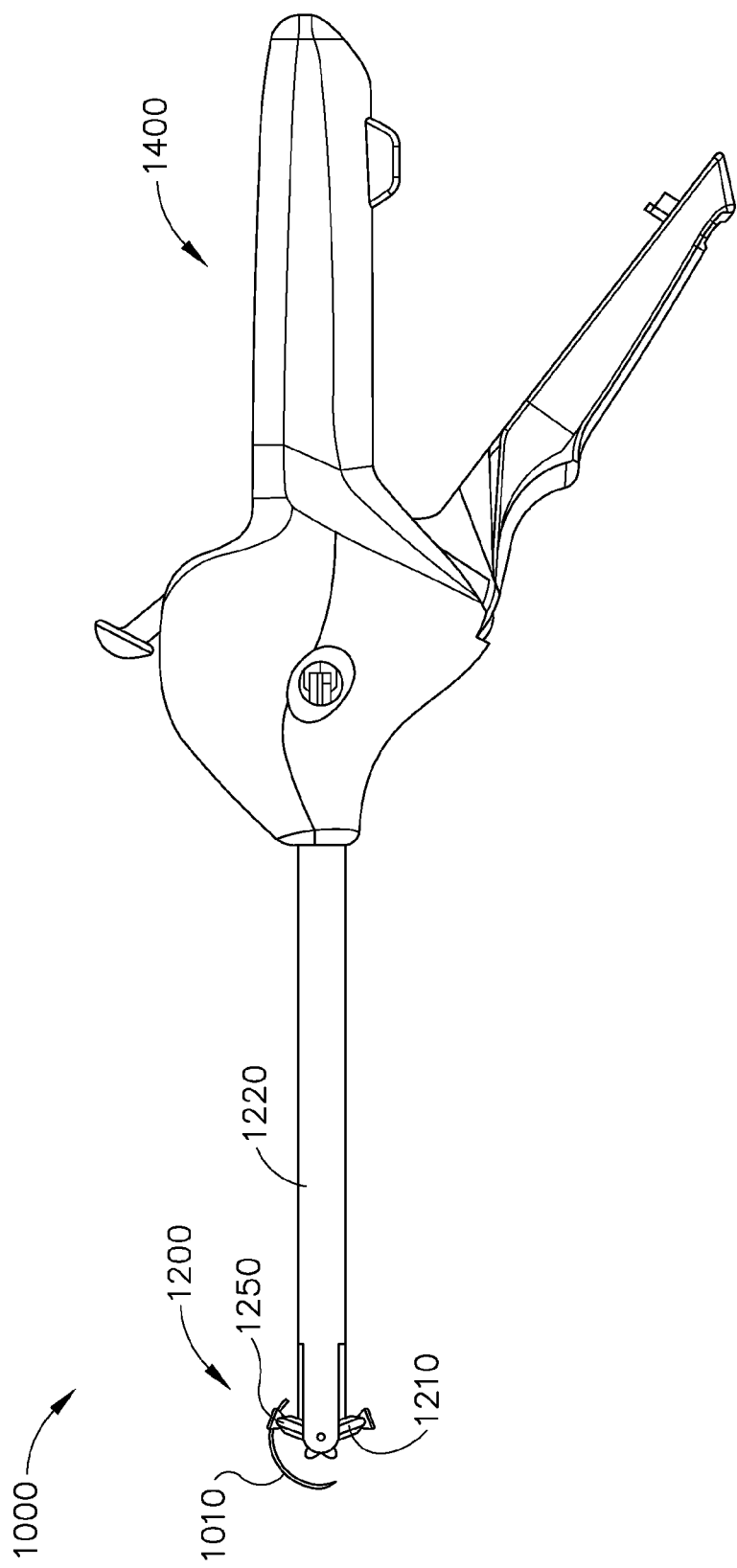
FIG. 15A depicts a side elevational view of an exemplary alternative version of a surgical instrument in an unactuated configuration.
Figure 15B:
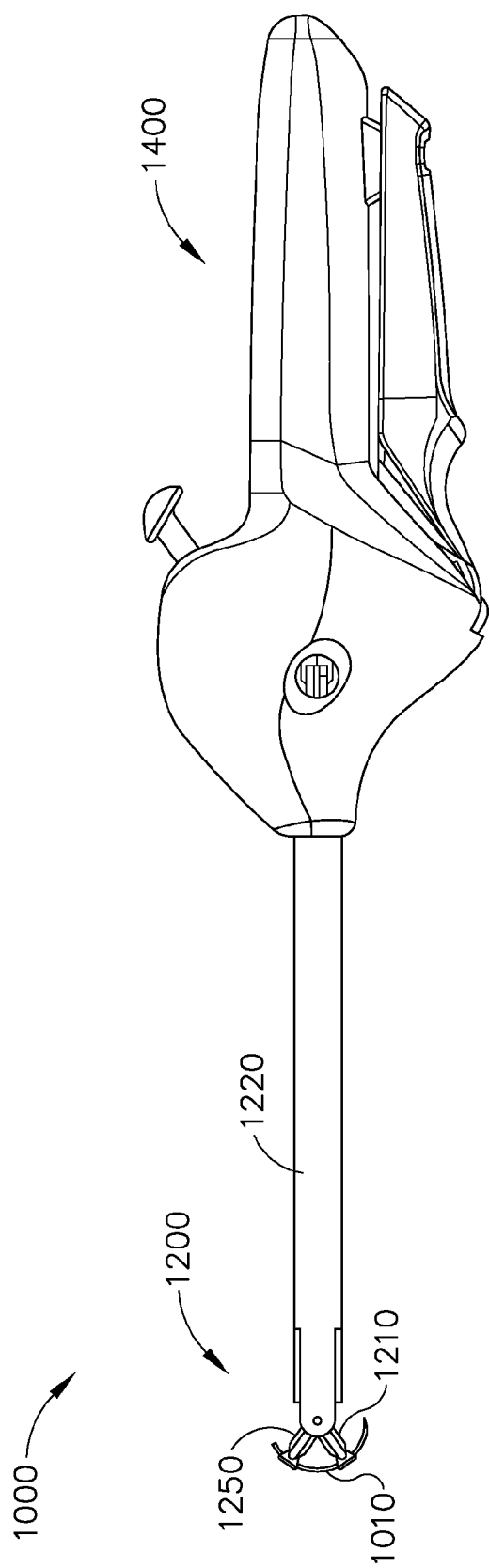
FIG. 15B depicts a side elevational view of the surgical instrument of FIG. 15A in an actuated configuration.

FIGS. 15A-15B show an alternative version of surgical instrument (1000) for suturing that uses linear motion of components within shaft (1220) in order to pass a needle (1010) between two grasping arms (1250, 1210) positioned on an end effector (1200) at the end of shaft (1220). It will be appreciated that actuation of a handle assembly (1400) via squeezing handle assembly (1400) is operable to move linear rods, push-pull cables, and/or other linear actuating components contained within shaft (1220) in order to move grasping arms (1210, 1250). FIG. 15A shows surgical instrument (1000) is in one position without handle assembly (1400) being actuated while FIG. 15B shows handle assembly (1400) being actuated and grasping arms (1210, 1250) being moved to pass needle (1010) therebetween. By way of example only, surgical instrument (1000) may be constructed in accordance with at least some of the teachings of U.S. Patent Pub. No. 2011/0313433, now U.S. Pat. No. 9,168,037, issued on Oct. 27, 2015, and/or Provisional Application No. 61/355,832, the disclosures of which have already been incorporated by reference herein. As another merely illustrative example, surgical instrument (1000) may be constructed in accordance with at least some of the teachings of U.S. Pat. No. 5,674,230, entitled "Surgical Suturing Apparatus with Locking Mechanisms," issued Oct. 7, 1997, the disclosure of which is incorporated by reference herein. Other suitable types of instruments that may incorporate at least some of the following teachings will be apparent to those of ordinary skill in the art in view of the teachings herein.

Figure 16A:
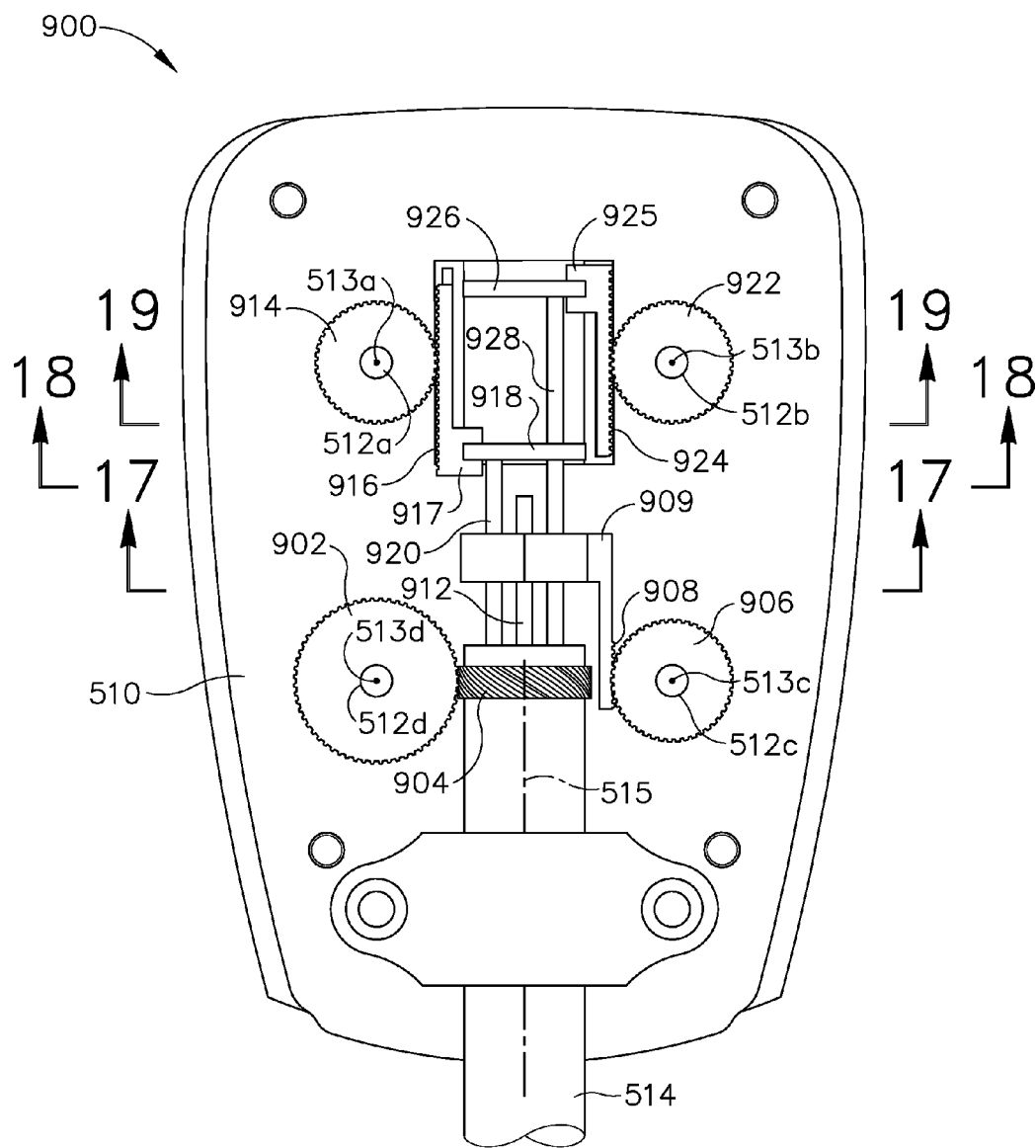
FIG. 16A depicts a top plan view of an exemplary alternative version of a drive assembly incorporating the base of FIG. 8, in a first operational configuration.

FIGS. 16A-16D show a version of drive assembly (900) operable for use in situations where an end effector controlled by linear actuators is used such as end effector (1200) shown in FIGS. 15A-15B and/or other variations of surgical instruments (1000) described above. In other words, drive assembly (900) may be used as a substitute for handle assembly (1400) in numerous variations of surgical instrument (1000) described above. As shown in FIG. 16A, an outer helical gear (904) is unitarily secured to outer shaft (514), which represents an equivalent of the proximal end of shaft (1220). The exterior helical teeth of gear (904) mesh with complementary helical teeth of helical gear (902). Helical gear (902) is unitarily secured to drive shaft (512d). Thus, as drive shaft (512d) is driven to rotate about axis (513d), helical gear (902) is driven to rotate about axis (513d), which in turn drives shaft (514) to rotate about axis (515) through engagement with gear (904). Bushings within shaft (514) cause rods (920, 928) to orbit about axis (515) when shaft (514) is rotated about axis (515), as will be described in greater detail below. It should be understood that rotation of shaft (514) provides rotation of end effector (1200). Another rod (912), which will also be described in greater detail below, may be configured to rotate with shaft (514), such as through a keyed relationship with one or more of the bushings referred to above.

Figure 17:
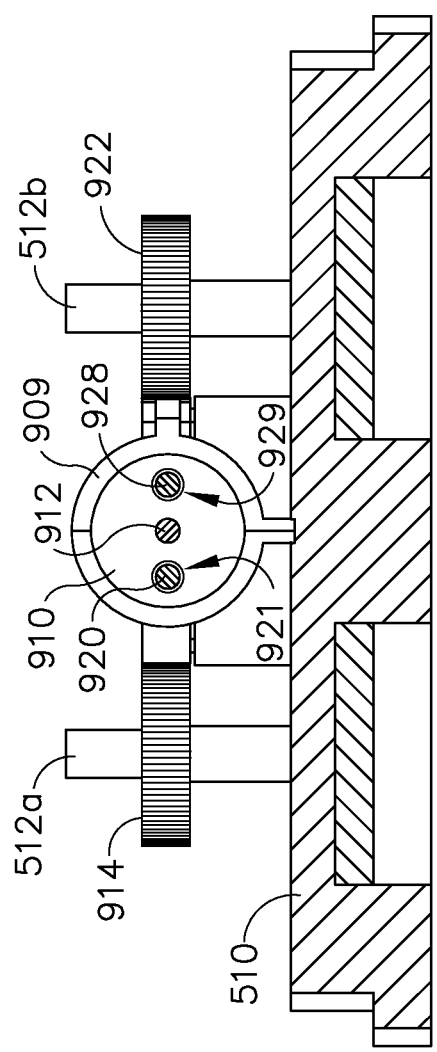
FIG. 17 depicts a partially cross sectional view taken along line 17-17 of FIG. 16A.

Drive assembly (900) further comprises a first pinion (906) and first rack (908). First pinion (906) is unitarily secured to drive shaft (512c). Thus, as drive shaft (512c) is driven to rotate about axis (513c), pinion (906) is driven to rotate about axis (513c), which in turn provides linear translation of rack (908). Rack (908) is an integral feature of a yoke (909), which is coupled with a drive disc (910) as best seen in FIG. 17. Drive disc (910) is secured to yoke (909) in a manner that permits disc (910) to rotate about axis (515) within yoke (909), though disc (910) translates longitudinally with yoke (909) as will be described in greater detail below. A middle rod (912) is unitarily secured to disc (910). As best seen in FIG. 17, disc (910) includes a pair of openings (921, 929). A left rod (920) passes through opening (921) while a right rod (928) passes through opening (929). Rods (920, 928) thus translate freely relative to disc (910); and disc (910) translates freely relative to rods (920, 928). When drive shaft (512d) is activated to rotate shaft (514), rods (920, 928) will orbit about axis (515) while disc (910) and rod (912) rotate about axis (515).

Figure 16B:
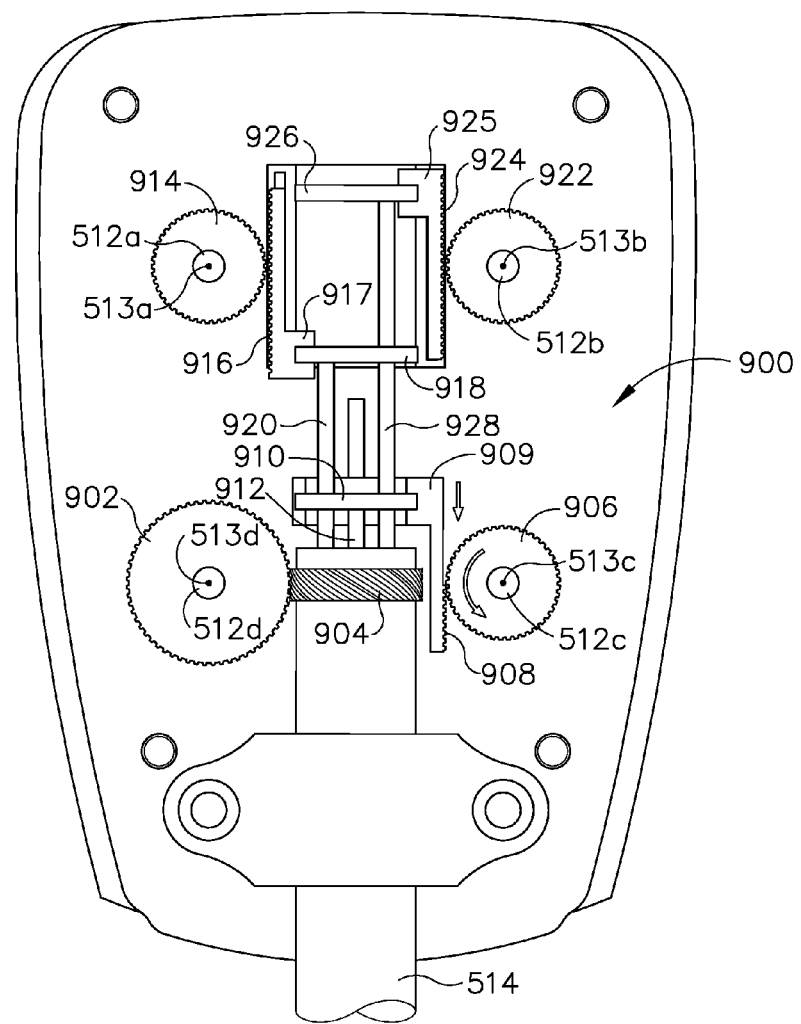
FIG. 16B depicts a top plan view of the drive assembly shown in FIG. 16A in a second operational configuration.

FIG. 16B shows first pinion (906) rotated and first rack (908) advanced such that first yoke (909), first disc (910), and middle rod (912) are advanced distally. Middle rod (912) is in communication with end effector (1200) such that longitudinal translation of middle rod (912) pivots grasping arms (1210, 1250) toward or away from each other based on the longitudinal position of middle rod (912). In some versions, grasping arms (1210, 1250) are pivoted toward each other to the position shown in FIG. 15B when rod (912) is advanced to the distal position shown in FIG. 16B; then away from each other to the position shown in FIG. 15A when rod (912) is retracted back to the proximal position shown in FIG. 16A. Alternatively, these relationships could be reversed.

Figure 18:
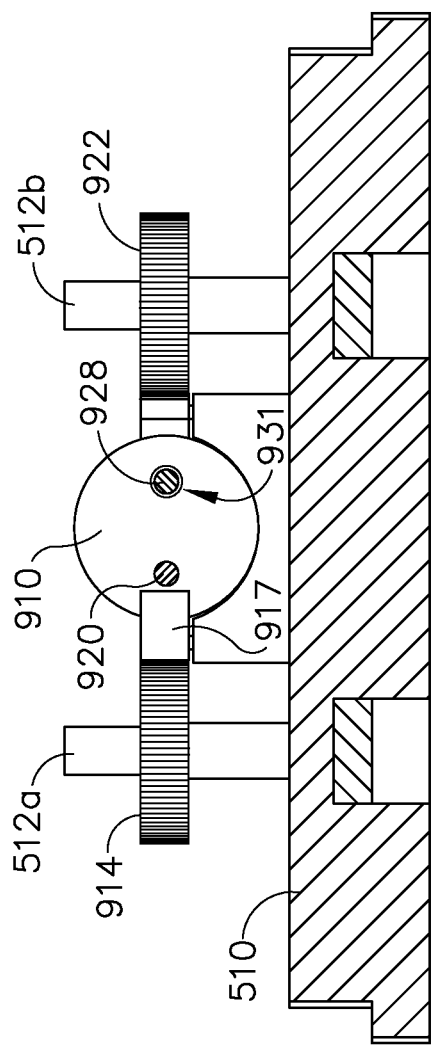
FIG. 18 depicts a partially cross sectional view taken along line 18-18 of FIG. 16A.

A second pinion (914) is unitarily secured to drive shaft (512a), and meshes with a rack (916). Thus, as drive shaft (512a) is driven to rotate about axis (513a), pinion (914) is driven to rotate about axis (513a), which in turn provides linear translation of rack (916). Rack (916) is an integral feature of a yoke (917), which is coupled with a drive disc (918). Drive disc (918) is secured to yoke (917) in a manner that permits disc (918) to rotate about axis (515) within yoke (917), though disc (918) translates longitudinally with yoke (917) as will be described in greater detail below. Left rod (920) is unitarily secured to disc (918). As best seen in FIG. 18, disc (918) includes an opening (931), through which right rod (928) passes. Rod (928) thus translates freely relative to disc (918); and disc (918) translates freely relative to rod (928). When drive shaft (512d) is activated to rotate shaft (514), rods (920, 928) will orbit about axis (515) while disc (918) rotates about axis (515).

Figure 16C:
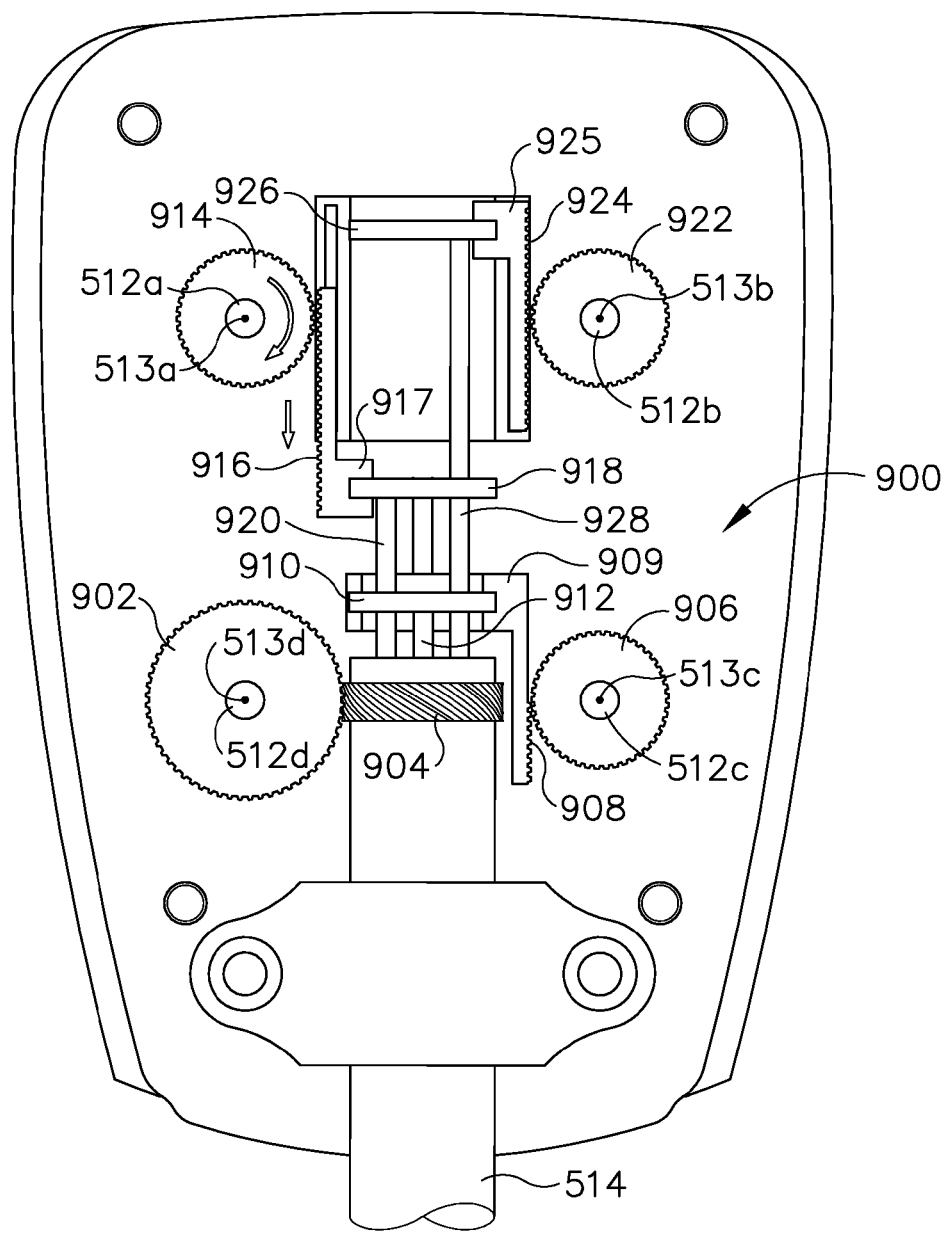
FIG. 16C depicts a top plan view of the drive assembly shown in FIG. 16A in a third operational configuration.

FIG. 16C shows second pinion (914) rotated and second rack (916) advanced such that second yoke (917), second disc (910), and left rod (920) are advanced distally. Left rod (920) is in communication with end effector (1200) such that longitudinal translation of left rod (920) causes grasping arm (1210) to selectively grasp or release needle (1010) based on the longitudinal position of left rod (920). In some versions, grasping arm (1210) is actuated to firmly grasp needle (1010) when rod (920) is advanced to the distal position shown in FIG. 16C; then release needle (1010) when rod (920) is retracted back to the proximal position shown in FIG. 16A. Alternatively, these relationships could be reversed.

Figure 19:
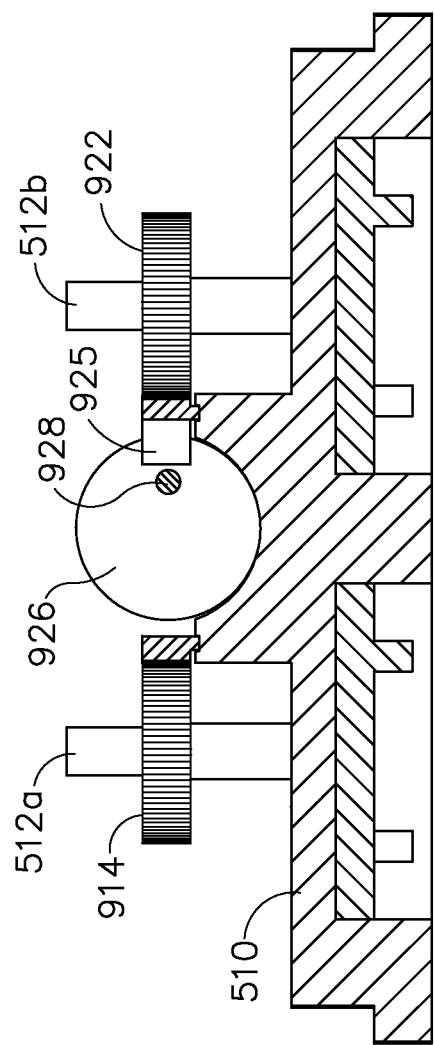
FIG. 19 depicts a partially cross sectional view taken along line 19-19 of FIG. 16A.

A third pinion (922) is unitarily secured to drive shaft (512b), and meshes with a rack (924). Thus, as drive shaft (512b) is driven to rotate about axis (513b), pinion (922) is driven to rotate about axis (513b), which in turn provides linear translation of rack (924). Rack (924) is an integral feature of a yoke (925), which is coupled with a drive disc (926). Drive disc (926) is secured to yoke (925) in a manner that permits disc (926) to rotate about axis (515) within yoke (925), though disc (926) translates longitudinally with yoke (925) as will be described in greater detail below. Right rod (928) is unitarily secured to disc (926), as can also be seen in FIG. 19. When drive shaft (512d) is activated to rotate shaft (514), rods (928) will orbit about axis (515) while disc (926) rotates about axis (515).

Figure 16D:
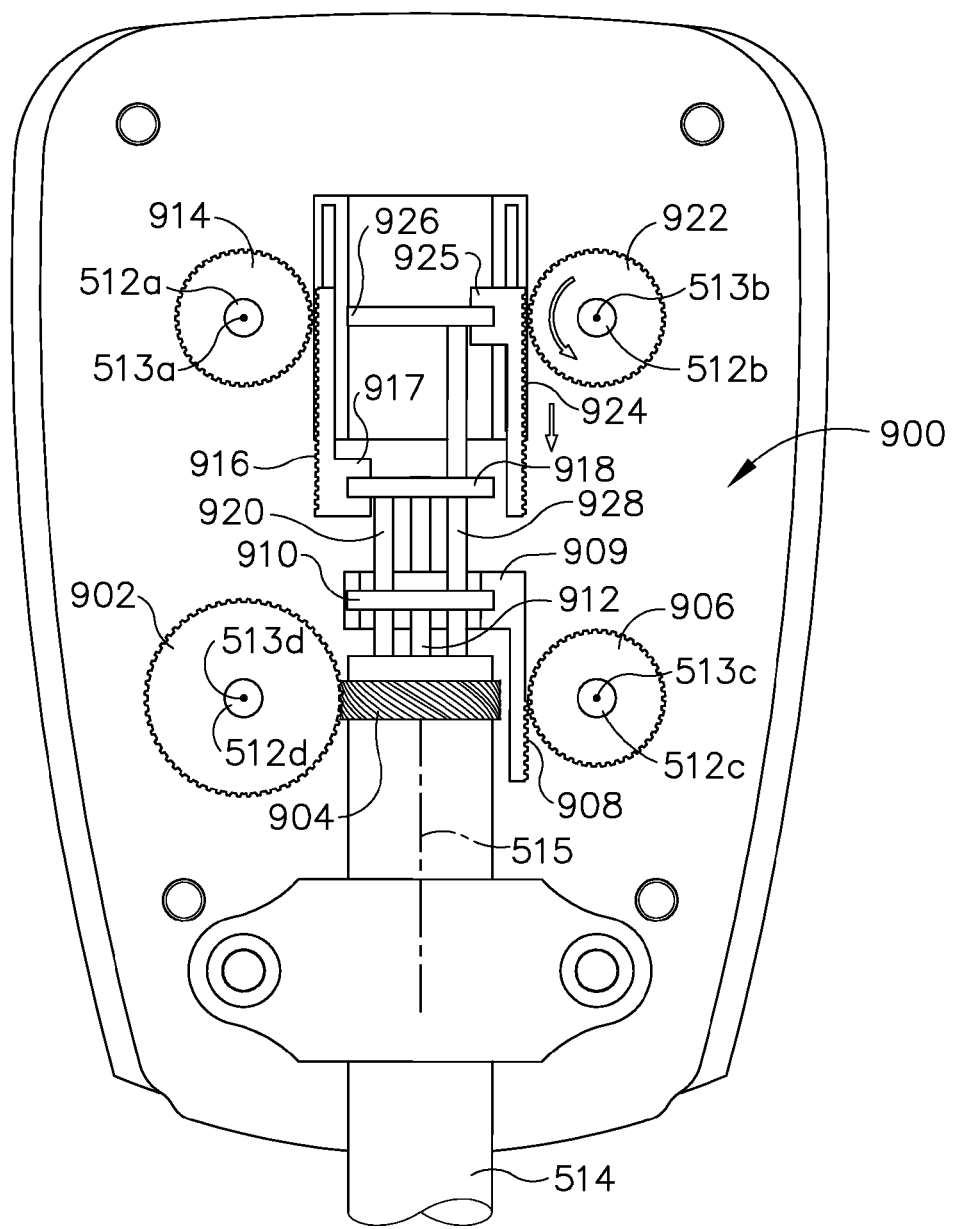
FIG. 16D depicts a top plan view of the drive assembly shown in FIG. 16A in a fourth operational configuration.

FIG. 16D shows third pinion (922) rotated and third rack (924) advanced such that third yoke (925), third disc (926), and right rod (928) are advanced distally. Right rod (928) is in communication with end effector (1200) such that longitudinal translation of right rod (928) causes grasping arm (1250) to selectively grasp or release needle (1010) based on the longitudinal position of right rod (928). In some versions, grasping arm (1250) is actuated to firmly grasp needle (1010) when rod (928) is advanced to the distal position shown in FIG. 16D; then release needle (1010) when rod (928) is retracted back to the proximal position shown in FIG. 16A. Alternatively, these relationships could be reversed.

One exemplary sequence of operation of surgical instrument (1000) by drive assembly (900) is shown with respect to FIGS. 16B-16D. In this example, grasping arm (1210) grasps needle (1010), such that left rod (920) is advanced distally to the position shown in FIG. 16C. Then, middle rod (912) is advanced distally by activating drive shaft (512c) as shown in FIG. 16B, to pivot grasping arms (1210, 1250) toward each other. This action may be used to drive needle (1010) through tissue. Next, right rod (928) is advanced distally by activating drive shaft (512b) as shown in FIG. 16D, to grasp needle (1010) with grasping arm (1250). Middle rod (912) remains advanced distally at this stage, holding grasping arms (1210, 1250) at the forward pivoted position shown in FIG. 15B. Once grasping arm (1250) has grasped needle (1010), drive shaft (512a) is activated to retract left arm (920) proximally, to release needle (1010) from grasping arm (1210). Drive shaft (512c) is then activated to retract middle rod (912) proximally to pivot grasping arms (1210, 1250) back to the open position shown in FIG. 15A. This action may be used to pull needle (1010) and an attached suture through tissue. In versions where both ends of needle (1010) are sharp and the suture is secured to the middle of needle (1010), end effector (1200) may be repositioned to use grasping arm (1250) to drive the opposite end of needle (1010) through tissue to make another stitch, using a reversal of the motions described above. In versions where just one end of needle (1010) is sharp and the suture is attached to the blunt end of needle (1010), the above motions may be reversed away from the tissue to pass control of needle (1010) back to grasping arm (1210) before making another stitch in the tissue. It should also be understood that drive shaft (512d) may be activated at any suitable time to rotate shaft (514) and end effector (1200) about axis (515) to reposition end effector (1200) about axis. Alternatively, the rotational position of shaft (514) and end effector (1200) about axis (515) may be substantially fixed. Still other suitable ways in which drive assembly (900) may be used to drive end effector (1200) will be apparent to those of ordinary skill in the art in view of the teachings herein.

VI. Miscellaneous

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) an end effector, comprising:
      (i) a first needle receiving arm, wherein the first needle receiving arm is operable to selectively engage and disengage a needle, wherein at least part of the first needle receiving arm extends along a first arm axis, wherein the first needle receiving arm is operable to rotate about the first arm axis, and
      (ii) a second needle receiving arm, wherein the second needle receiving arm is operable to selectively engage and disengage a needle, wherein at least part of the second needle receiving arm extends along a second arm axis;
   (b) a shaft assembly, wherein the shaft assembly has a distal end and a proximal end, wherein the end effector is located at the distal end of the shaft assembly, wherein the shaft assembly defines a shaft axis, wherein the first arm axis and the second arm axis extend parallel to the shaft axis, wherein the shaft assembly comprises:
      (i) a first shaft associated with the first needle receiving arm, wherein the first shaft is rotatable about the first arm axis to cause the first needle receiving arm to selectively engage and disengage a needle, and
      (ii) a second shaft associated with the second needle receiving arm, wherein the second shaft is rotatable about the second arm axis to cause the second needle receiving arm to selectively engage and disengage a needle; and
   (c) a drive assembly, wherein the drive assembly is located at the proximal end of the shaft assembly, wherein the drive assembly comprises:
      (i) a first rotary drive shaft operable to drive the first needle receiving arm to selectively engage and disengage a needle, wherein the first rotary drive shaft is rotatable about a first drive axis that is perpendicular to the shaft axis,
      (ii) a second rotary drive shaft operable to drive the second needle receiving arm to selectively engage and disengage a needle, wherein the second rotary drive shaft is rotatable about a second drive axis that is perpendicular to the shaft axis,
      (iii) a third rotary drive shaft operable to rotate the first needle receiving arm about the first arm axis, wherein the third rotary drive shaft is rotatable about a third drive axis,
      (iv) a base, wherein the first drive axis, the second drive axis, and the third drive axis extend through the base at respective fixed positions relative to the base,
      (v) a first ring gear operable to rotate in response to rotation of the first rotary drive shaft about the first drive axis, wherein the first ring gear encompasses a proximal portion of the first shaft and engages the first shaft to drive the first shaft, wherein the first ring gear is rotatable about the shaft axis, and
      (vi) a second ring gear operable to rotate in response to rotation of the second rotary drive shaft about the second drive axis, wherein the second ring gear encompasses a proximal portion of the first shaft and the second shaft, wherein the second ring gear engages the second shaft to drive the second shaft, wherein the first shaft is freely rotatable relative to the second ring gear.

2. The apparatus of claim 1, wherein the first arm axis is parallel to the shaft axis.

3. The apparatus of claim 1, wherein the third rotary drive shaft is perpendicular to the shaft axis.

4. The apparatus of claim 1, wherein the shaft assembly further comprises a third shaft associated with the first needle receiving arm, wherein the third shaft is operable to rotate the first needle receiving arm about the first arm axis.

5. The apparatus of claim 4, wherein the drive assembly further comprises a gear secured to a proximal portion of the third shaft, wherein the drive assembly is operable to convert rotation of the third rotary drive shaft about the third drive axis into rotation of the gear about the first arm axis.

6. The apparatus of claim 4, wherein the first shaft is coaxially positioned within the third shaft.

7. The apparatus of claim 1, wherein the first shaft and the second shaft are parallel to each other.

8. An apparatus comprising:
   (a) a shaft, wherein the shaft has a distal end and a proximal end;
   (b) an end effector located at the distal end of the shaft;
   (c) a shaft assembly coupled to the end effector and extending through the shaft to the proximal end of the shaft, wherein the shaft assembly comprises:
      (i) an inner drive shaft,
      (ii) an outer drive shaft, and
      (iii) an adjacent drive shaft, wherein the inner drive shaft is disposed within an interior of the outer drive shaft, wherein the inner drive shaft and the outer drive shaft are each independently movable relative to one another and to the shaft, wherein the adjacent drive shaft is parallel to the outer drive shaft; and
   (d) a drive assembly, wherein the drive assembly is located at the proximal end of the shaft assembly, wherein the adjacent drive shaft, the inner drive shaft, and the outer drive shaft extend from the drive assembly to the end effector, wherein the drive assembly comprises:

(i) a first rotary drive shaft operable to drive the inner drive shaft, wherein the first rotary drive shaft is rotatable about a first drive axis that is perpendicular to the shaft axis, (ii) a second rotary drive shaft operable to drive the adjacent shaft, wherein the second rotary drive shaft is rotatable about a second drive axis that is perpendicular to the shaft axis, and (iii) a clutch assembly housing a proximal end of the outer shaft, wherein the clutch assembly is operable to selectively couple the inner drive shaft with the outer drive shaft, such that the inner drive shaft is rotatable relative to the outer drive shaft when the clutch assembly is in a decoupled configuration and such that the inner drive shaft is operable to drive the outer drive shaft when the clutch assembly is in a coupled configuration, wherein the first rotary drive shaft and the second rotary drive shaft are in fixed positions such that the first drive axis and the second drive axis are separated from each other by a fixed distance.

\* \* \* \* \*